United States Patent
Eda et al.

(10) Patent No.: US 8,367,695 B2
(45) Date of Patent: Feb. 5, 2013

(54) CONDENSED TETRAHYDROQUINOLINE DERIVATIVE AND USE THEREOF FOR MEDICAL PURPOSES

(75) Inventors: Masahiro Eda, Osaka (JP); Tomoko Kuroda, Osaka (JP); Keiichi Aritomo, Osaka (JP); Yoshiyuki Aoki, Osaka (JP); Satoshi Kaneko, Osaka (JP)

(73) Assignee: Mitsubishi Tanabe Pharma Corporation, Osaka-shi (JP)

( * ) Notice: Subject to any disclaimer, the term of this patent is extended or adjusted under 35 U.S.C. 154(b) by 564 days.

(21) Appl. No.: 12/523,031

(22) PCT Filed: Jan. 15, 2008

(86) PCT No.: PCT/JP2008/050349
§ 371 (c)(1),
(2), (4) Date: Sep. 23, 2009

(87) PCT Pub. No.: WO2008/087936
PCT Pub. Date: Jul. 24, 2008

(65) Prior Publication Data
US 2010/0063055 A1      Mar. 11, 2010

(30) Foreign Application Priority Data
Jan. 15, 2007   (JP) ................. 2007-005472

(51) Int. Cl.
*A61K 31/435* (2006.01)
*A61K 31/4355* (2006.01)
(52) U.S. Cl. .............. 514/290; 546/80; 546/81; 546/82
(58) Field of Classification Search .......... 546/80, 546/81, 82; 514/290
See application file for complete search history.

(56) References Cited

U.S. PATENT DOCUMENTS

| | | | |
|---|---|---|---|
| 5,688,808 A | 11/1997 | Jones et al. | |
| 5,688,810 A | 11/1997 | Jones et al. | |
| 5,693,646 A | 12/1997 | Jones et al. | |
| 5,693,647 A | 12/1997 | Jones et al. | |
| 5,696,127 A | 12/1997 | Jones et al. | |
| 5,696,130 A | 12/1997 | Jones et al. | |
| 5,696,133 A | 12/1997 | Jones et al. | |
| 5,994,544 A | 11/1999 | Jones et al. | |
| 6,093,821 A | 7/2000 | Jones et al. | |
| 6,121,450 A | 9/2000 | Jones et al. | |
| 6,448,405 B1 | 9/2002 | Jones et al. | |
| 6,583,180 B2 | 6/2003 | Link et al. | |
| 6,696,459 B1 | 2/2004 | Jones et al. | |
| 6,852,719 B2 | 2/2005 | Liu et al. | |
| 6,858,627 B2 | 2/2005 | Bekkali et al. | |
| 7,235,662 B2 | 6/2007 | Hadida-Ruah et al. | |
| 7,576,076 B2 | 8/2009 | Clark et al. | |
| 2004/0186132 A1 | 9/2004 | Jones et al. | |
| 2004/0236109 A1 | 11/2004 | Van Straten et al. | |
| 2007/0254917 A1 | 11/2007 | Higuchi et al. | |
| 2007/0281928 A1 | 12/2007 | Clark et al. | |

FOREIGN PATENT DOCUMENTS

| | | |
|---|---|---|
| JP | 10-510840 T2 | 10/1998 |
| WO | WO 96/19458 A2 | 6/1996 |
| WO | WO 00/06137 A2 | 2/2000 |
| WO | WO 02/064550 A1 | 8/2002 |
| WO | WO 03/004028 A1 | 1/2003 |
| WO | WO 2004/018429 A2 | 3/2004 |
| WO | WO 2004/110385 A2 | 12/2004 |
| WO | WO 2005/087769 A1 | 9/2005 |
| WO | WO 2006/014394 A1 | 2/2006 |
| WO | WO 2006/019716 A1 | 2/2006 |

OTHER PUBLICATIONS

Alnemri et al., *Journal of Biological Chemistry*, 266(27): 18072-18081 (1991).
Belanoff et al., *Society of Biological Psychiatry*, 52(5): 386-392 (2002).
Binart et al., *Proc. Natl. Acad. Sci. USA*, 88: 10681-10685 (Dec. 1991).
Clark et al., *Investigative Ophthalmology and Visual Science*, 37(5): 805-813 (Apr. 1996).
Invitrogen, "Bac-to-Bac® Baculovirus Expression System" User Manual, pp. i-viii and 65-70 (Jan. 19, 2009).
Mikuni, *Shinkei Kenkyu no Shinpo* (*Advances in Neurological Sciences*), 42(4): 656-665 (1998).
Murphy et al., *J. Psychiatry Neuroscience*, 18(5): 209-213 (Nov. 1993).
Murray et al., *Journal of the American Chemical Society*, 55: 2805-2806 (Jul. 1933).
Smith et al., *Neuroimmunomodulation*, 1: 66-73 (1994).
Suzuki et al., Organic Synthesis Via Boranes, vol. 3, pp. x-xv (Aldrich Chemical Company, Inc., 2003).
Theoclitou et al., *Tetrahedron Letters*, 43: 3907-3910 (2002).
Belanoff et al., *Biological Psychiatry*, 52(5): 386-392 (2002).

*Primary Examiner* — Rita Desai
(74) *Attorney, Agent, or Firm* — Leydig, Voit & Mayer, Ltd.

(57) ABSTRACT

The problem of the present invention is to provide a compound having a GR selective binding activity, which shows less action on other nuclear receptors such as progesterone receptor (PR), mineralocorticoid receptor (MR) and the like. The present invention provides a condensed tetrahydroquinoline compound represented by the following formula (I)

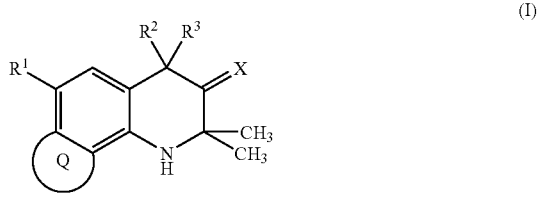

(I)

wherein each symbol is as defined in the present specification, or a pharmaceutically acceptable salt thereof or a hydrate thereof.

12 Claims, No Drawings

CONDENSED TETRAHYDROQUINOLINE DERIVATIVE AND USE THEREOF FOR MEDICAL PURPOSES

TECHNICAL FIELD

The present invention relates to a condensed tetrahydroquinoline compound having a glucocorticoid receptor antagonist action or a pharmaceutically acceptable salt thereof, and a hydrate thereof, and a therapeutic agent for a disease involving intracerebral glucocorticoid receptor in a mammal inclusive of human, particularly, use of the aforementioned condensed tetrahydroquinoline compound for the treatment of central nervous system diseases such as depression, psychotic major depression, bipolar affective disorder, posttraumatic stress disorder, anxiety disorder, schizophrenia, Alzheimer's disease and the like.

BACKGROUND ART

Physiological and psychological stress promotes hypothalamus-pituitary-adrenal axis (HPA axis) to cause secretion of glucocorticoid (cortisol etc.) from the adrenal cortex. Glucocorticoid is known to bind to a glucocorticoid receptor (hereinafter sometimes to be referred to as "GR") in the brain, and cause various symptoms (lowering of motivation, suppression of food ingestion, neuronal loss in the hippocampus, reduction in noradrenaline neural activity, increase of serotonin 2A receptor function, steroidal hallucination etc.) leading to the etiology of depression and the like (see non-patent document 1).

As an example of use of a compound (GR antagonist) inhibiting a bond between glucocorticoid and GR for the treatment of central nervous system diseases, mifepristone has been reported to improve the symptoms of depression (see non-patent document 2). However, mifepristone is known to show a strong progesterone receptor (hereinafter sometimes to be referred to as "PR") antagonist action, and is feared to influence emmenia and the like.

In fact, mifepristone has been reported to show side effects in the reproductive system such as uterus convulsion and the like (see non-patent document 3).

To use GR antagonist for the treatment of central nervous system diseases such as depression and the like, the antagonist is desired to selectively act on GR and not act on other receptors.

Examples of the GR antagonist include modified pyrimidine derivative (see patent document 1), condensed azadecalin derivative (see patent document 2), triphenyl derivative (see patent document 3), phenanthrenol derivative (see patent document 4), tertiary amine derivative (see patent document 5), dihydroquinoline derivative (see patent document 6), 6-oxa-2,4-diazachrysene derivative (see patent document 7), and the like. However, there is no report relating to a GR antagonist of condensed tetrahydroquinoline compound.

On the other hand, a tetrahydroquinoline derivative having a chemical structure similar to that of a condensed tetrahydroquinoline compound has been reported (see patent document 8). However, it is not described or suggested that the derivative is effective for the treatment of central nervous system diseases.

In addition, there is a report on the binding action of a dihydroquinoline or tetrahydroquinoline derivative to GR or mineralocorticoid receptor (hereinafter sometimes to be referred to as "MR") (see patent document 9).

However, this report does not describe at all the selectivity between such different receptors, and a tetrahydroquinoline compound wherein cyclopentyl or 5-membered heteroaryl is condensed is not described or even suggested.

Furthermore, a compound encompassing enormous combinations of structures is disclosed as a steroid receptor modulation drug (see patent document 10). However, a compound disclosed as a concrete example thereof is solely a derivative having a tetrahydroquinoline skeleton, and a tetrahydroquinoline compound wherein cyclopentyl or 5-membered heteroaryl is condensed is not described or even suggested.

patent document 1: WO2006/014394
patent document 2: WO2005/087769
patent document 3: WO2000/06137
patent document 4: U.S. Pat. No. 6,852,719
patent document 5: WO2002/064550
patent document 6: WO2004/018429
patent document 7: WO2004/110385
patent document 8: WO2003/004028
patent document 9: WO2006/19716
patent document 10: WO1996/019458
non-patent document 1: Masahiko Mikuni, Shinkei Shinpo (Advances in neurological sciences), 1998, 42(4), 656-65.
non-patent document 2: Murphy, J Psychiatry Neurosci., 1993, November; 18(5): 209-213.
non-patent document 3: Belanof, Biological Psychiatry., 2002, 52(5), 386-92.

DISCLOSURE OF THE INVENTION

Problems to be Solved by the Invention

An object of the present invention is to provide a compound having a GR selective binding activity, which shows less action on other nuclear receptors such as PR, MR and the like.

Means of Solving the Problems

The present inventors have found that a novel condensed tetrahydroquinoline compound has a strong GR antagonist action but shows an attenuated action on PR and MR, and studied the pharmacological action of the compound from various aspects, which resulted in the completion of the present invention.

Furthermore, they have conducted various studies of the pharmacological action of the compound, and found that the compound has a strong GR binding inhibitory effect but shows an attenuated action on PR and MR, and that the compound is useful as a therapeutic drug for the treatment of diseases relating to a phenomenon that steroid pharmaceutical products such as endogenous cortisol, dexamethasone and the like bind with glucocorticoid receptor, particularly central nervous system diseases such as depression, psychotic major depression, bipolar affective disorder, posttraumatic stress disorder, anxiety disorder, schizophrenia and Alzheimer's disease, which resulted in the completion of the present invention.

Accordingly, the gist of the present invention exists in the following (1) to (13).

(1) A condensed tetrahydroquinoline compound represented by the following formula (I)

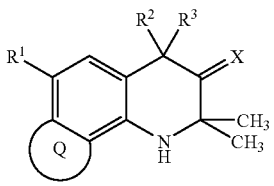
(I)

wherein $R^1$ is optionally substituted $C_6$-$C_{10}$ aryl, optionally substituted 5- or 6-membered heterocyclic aryl or optionally substituted bicyclic heteroaryl, $R^2$ and $R^3$ are the same or different and each independently is a hydrogen atom, $C_1$-$C_6$ alkyl, $C_1$-$C_6$ alkyl optionally substituted by 1 to 3 halogens, $C_2$-$C_6$ alkenyl or $C_2$-$C_6$ alkynyl, ring Q is the following formula (II-a), (II-b) or (II-c),

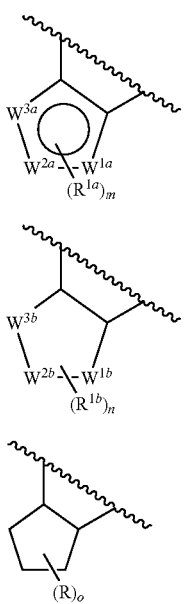

II-a

II-b

II-c wherein m, n and o are each independently 0, 1 or 2, R, $R^{1a}$ and $R^{1b}$ may be the same or different and each independently is a hydrogen atom, a halogen atom, optionally substituted $C_1$-$C_6$ alkyl, optionally substituted $C_1$-$C_{10}$ aryl or optionally substituted aryl-$C_1$-$C_6$ alkyl (provided that when o is 2, R may be =O), $W^{1a}$, $W^{2a}$ and $W^{3a}$ are the same or different and each independently is —$CR^{1a}$=, a nitrogen atom, a sulfur atom or an oxygen atom, $W^{1b}$ and $W^{2b}$ are the same or different and each independently is —$CHR^{1b}$—, —$C(R^{1b})_2$—, —CO—, a nitrogen atom or an oxygen atom, $W^{3b}$ is —$CHR^{1b}$—, —CO—, a nitrogen atom, a sulfur atom or an oxygen atom (provided that at least one of $W^{1a}$, $W^{2a}$ and $W^{3a}$, or $W^{1b}$, $W^{2b}$ and $W^{3b}$, is —$CHR^{1b}$, and at least one of them is a group other than a carbon atom, and when $W^{1a}$, $W^{2a}$ and $W^{3a}$, or $W^{1b}$, $W^{2b}$ and $W^{3b}$ are plural nitrogen atoms, sulfur atoms or oxygen atoms, then the atoms are not sequentially bonded), and X is =$CH_2$ or an oxygen atom, or a pharmaceutically acceptable salt thereof, or a hydrate thereof, (2) the condensed tetrahydroquinoline compound of the aforementioned (1), wherein $R^1$ is the formula (III-a)

III-a wherein $R^a$ is $C_1$-$C_6$ alkyl or a halogen atom, $A^{1a}$ and $A^{2a}$ are the same or different and each independently is —N= or —CH=, and $A^{3a}$ is —NH— or —O—, the formula (III-b)

III-b wherein $A^{1b}$ and $A^{2b}$ are the same or different and each independently is —NH—, —N= or —CH=, $A^{3b}$ is a nitrogen atom or a carbon atom, $A^{4b}$ and $A^{5b}$ are the same or different and each independently is a nitrogen atom or —$CR^b$=, and $R^b$ is a hydrogen atom, $C_1$-$C_6$ alkyl or a halogen atom, provided that at least two of $A^{1b}$, $A^{2b}$, $A^{3b}$, $A^{4b}$ and $A^{5b}$ are a carbon atom, —CH= or —$CR^b$=, the formula (III-c)

III-c

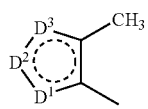

wherein $A^{1c}$ and $A^{4c}$ are the same or different and each independently is a nitrogen atom or a carbon atom, $A^{2c}$ is —NH—, —N= or —CH=, and $A^{3c}$ is —N= or —CH=, provided that $A^{1c}$ and $A^{4c}$ are not simultaneously nitrogen atoms, the formula (III-d)

III-d wherein $D^1$ is —S—, —$C(R^{d1})$= or —$N(R^{d2})$—, $D^2$ is —S—, —$C(R^{d2})$= or —N=, $D^3$ is —O—, —S—, —$C(R^{d2})$= or —N=, $R^{d1}$ is a hydrogen atom, $C_1$-$C_6$ alkyl, $C_1$-$C_6$ alkoxy, amino, $C_1$-$C_6$ alkylamino, di($C_1$-$C_6$ alkyl)amino, cyano or hydroxyiminomethyl, and $R^{d2}$ is a hydrogen atom, cyano or $C_1$-$C_6$ alkyl, provided that when any of $D^1$, $D^2$ and $D^3$ is —S— or —O—, the other two are not —O— and —S—, the formula (III-e)

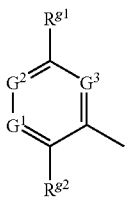

wherein G¹ is —N'— or —C(R^{g3})=, G² and G³ are the same or different and each independently is —N= or —CH=, R^{g1} is a hydrogen atom, a halogen atom or $C_1$-$C_6$ alkyl, R^{g2} is a halogen atom, $C_1$-$C_6$ alkyl or $C_1$-$C_6$ alkoxy, and R^{g3} is a hydrogen atom or a halogen atom, wherein one of G¹-G³ is —N=, and the other two are —C(R^{g3})= or —CH=, naphthyridine, thienopyridine, phthalazine, quinoline, benzoxazole, dioxoindoline, hydroxynaphthalene, 3,5-dimethylpyrazole, or phenyl optionally substituted by 1 or 2 groups selected from the group consisting of a hydroxyl group, a halogen atom, $C_1$-$C_6$ alkyl and $C_1$-$C_6$ alkoxy, or a pharmaceutically acceptable salt thereof, or a hydrate thereof, (3) the condensed tetrahydroquinoline compound of the aforementioned (1), wherein R¹ is the formula (III-d), naphthyridine, thienopyridine or phthalazine, and ring Q is the formula (II-b), or a pharmaceutically acceptable salt thereof, or a hydrate thereof, (4) the condensed tetrahydroquinoline compound of the aforementioned (1), which is 6-(2-chloro-4-hydroxyphenyl)-2,2,4,4-tetramethyl-2,3,4,7,8,9-hexahydro-1H-cyclopenta[h]quinolin-3-one,
6-(3,5-dimethylisoxazol-4-yl)-2,2,4,4-tetramethyl-2,3,4,7,8,9-hexahydro-1H-cyclopenta[h]quinolin-3-one,
6-(3,5-dimethyl-3H-imidazol-4-yl)-2,2,4,4-tetramethyl-2,3,4,7,8,9-hexahydro-1H-cyclopenta[h]quinolin-3-one,
6-(3,5-dimethyl-3H-[1,2,3]triazol-4-yl)-2,2,4,4-tetramethyl-2,3,4,7,8,9-hexahydro-1H-cyclopenta[h]quinolin-3-one,
6-(2-cyano-3-methylthiophen-4-yl)-2,2,4,4-tetramethyl-2,3,4,7,8,9-hexahydro-1H-cyclopenta[h]quinolin-3-one,
2,2,4,4-tetramethyl-6-(3-methylpyridin-4-yl)-2,3,4,7,8,9-hexahydro-1H-cyclopenta[h]quinolin-3-one,
6-(2-chloropyridin-3-yl)-2,2,4,4-tetramethyl-2,3,4,7,8,9-hexahydro-1H-cyclopenta[h]quinolin-3-one,
6-(5-fluoro-2-methoxypyridin-3-yl)-2,2,4,4-tetramethyl-2,3,4,7,8,9-hexahydro-1H-cyclopenta[h]quinolin-3-one,
6-(2,5-dimethylpyridin-4-yl)-2,2,4,4-tetramethyl-2,3,4,7,8,9-hexahydro-1H-cyclopenta[h]quinolin-3-one,
6-(1H-indol-7-yl)-2,2,4,4-tetramethyl-2,3,4,7,8,9-hexahydro-1H-cyclopenta[h]quinolin-3-one,
6-(5-fluoro-1H-indol-7-yl)-2,2,4,4-tetramethyl-2,3,4,7,8,9-hexahydro-1H-cyclopenta[h]quinolin-3-one,
6-(1H-benzimidazol-4-yl)-2,2,4,4-tetramethyl-2,3,4,7,8,9-hexahydro-1H-cyclopenta[h]quinolin-3-one,
2,2,4,4-tetramethyl-6-(1H-pyrrolo[3,2-b]pyridin-7-yl)-2,3,4,7,8,9-hexahydro-1H-cyclopenta[h]quinolin-3-one,
6-(imidazo[1,2-a]pyridin-5-yl)-2,2,4,4-tetramethyl-2,3,4,7,8,9-hexahydro-1H-cyclopenta[h]quinolin-3-one,
6-(1H-indazol-4-yl)-2,2,4,4-tetramethyl-2,3,4,7,8,9-hexahydro-1H-cyclopenta[h]quinolin-3-one,
2,2,4,4-tetramethyl-6-(pyrazolo[1,5-a]pyridin-4-yl)-2,3,4,7,8,9-hexahydro-1H-cyclopenta[h]quinolin-3-one,
2,2,4,4-tetramethyl-6-([1,2,4]triazolo[4,3-a]pyridin-5-yl)-2,3,4,7,8,9-hexahydro-1H-cyclopenta[h]quinolin-3-one,
6-(imidazo[1,2-a]pyrazin-5-yl)-2,2,4,4-tetramethyl-2,3,4,7,8,9-hexahydro-1H-cyclopenta[h]quinolin-3-one,
2,2,4,4-tetramethyl-6-(thieno[2,3-b]pyridin-3-yl)-2,3,4,7,8,9-hexahydro-1H-cyclopenta[h]quinolin-3-one,
2,2,4,4-tetramethyl-6-(quinolin-5-yl)-2,3,4,7,8,9-hexahydro-1H-cyclopenta[h]quinolin-3-one,
2,2,4,4-tetramethyl-6-([1,8]naphthyridin-4-yl)-2,3,4,7,8,9-hexahydro-1H-cyclopenta[h]quinolin-3-one,
2,2,4,4-tetramethyl-6-(phthalazin-5-yl)-2,3,4,7,8,9-hexahydro-1H-cyclopenta[h]quinolin-3-one,
6-(3,5-dimethylisoxazol-4-yl)-2,2,4,4-tetramethyl-3-methylene-2,3,4,7,8,9-hexahydro-1H-cyclopenta[h]quinoline,
6-(imidazo[1,2-a]pyridin-5-yl)-2,2,4,4-tetramethyl-3-methylene-2,3,4,7,8,9-hexahydro-1H-cyclopenta[h]quinoline,
2,2,4,4-tetramethyl-3-methylene-6-([1,8]naphthyridin-4-yl)-2,3,4,7,8,9-hexahydro-1H-cyclopenta[h]quinoline,
2,2,4,4-tetramethyl-3-methylene-6-([1,2,4]triazolo[4,3-a]pyridin-5-yl)-2,3,4,7,8,9-hexahydro-1H-cyclopenta[h]quinoline,
6-(imidazo[1,2-a]pyrazin-5-yl)-2,2,4,4-tetramethyl-3-methylene-2,3,4,7,8,9-hexahydro-1H-cyclopenta[h]quinoline,
6-(3,5-dimethyl-3H-[1,2,3]triazol-4-yl)-2,2,4,4-tetramethyl-3-methylene-2,3,4,7,8,9-hexahydro-1H-cyclopenta[h]quinoline,
6-(3,5-dimethyl-3H-imidazol-4-yl)-2,2,4,4-tetramethyl-3-methylene-2,3,4,7,8,9-hexahydro-1H-cyclopenta[h]quinoline,
2,2,4,4-tetramethyl-6-([1,8]naphthyridin-4-yl)-1,2,3,4,8,9-hexahydro-furo[2,3-h]quinolin-3-one or
2,2,4,4-tetramethyl-6-([1,8]naphthyridin-4-yl)-1,2,3,4-tetrahydro-furo[2,3-h]quinolin-3-one, or a pharmaceutically acceptable salt thereof, or a hydrate thereof, (5) the condensed tetrahydroquinoline compound of the aforementioned (1), which is 6-(3,5-dimethylisoxazol-4-yl)-2,2,4,4-tetramethyl-2,3,4,7,8,9-hexahydro-1H-cyclopenta[h]quinolin-3-one,
6-(3,5-dimethyl-3H-[1,2,3]triazol-4-yl)-2,2,4,4-tetramethyl-2,3,4,7,8,9-hexahydro-1H-cyclopenta[h]quinolin-3-one,
2,2,4,4-tetramethyl-6-(3-methylpyridin-4-yl)-2,3,4,7,8,9-hexahydro-1H-cyclopenta[h]quinolin-3-one,
6-(5-fluoro-2-methoxypyridin-3-yl)-2,2,4,4-tetramethyl-2,3,4,7,8,9-hexahydro-1H-cyclopenta[h]quinolin-3-one,
6-(2,5-dimethylpyridin-4-yl)-2,2,4,4-tetramethyl-2,3,4,7,8,9-hexahydro-1H-cyclopenta[h]quinolin-3-one,
6-(1H-indol-7-yl)-2,2,4,4-tetramethyl-2,3,4,7,8,9-hexahydro-1H-cyclopenta[h]quinolin-3-one,
2,2,4,4-tetramethyl-6-(1H-pyrrolo[3,2-b]pyridin-7-yl)-2,3,4,7,8,9-hexahydro-1H-cyclopenta[h]quinolin-3-one,
6-(imidazo[1,2-a]pyridin-5-yl)-2,2,4,4-tetramethyl-2,3,4,7,8,9-hexahydro-1H-cyclopenta[h]quinolin-3-one,
6-(1H-indazol-4-yl)-2,2,4,4-tetramethyl-2,3,4,7,8,9-hexahydro-1H-cyclopenta[h]quinolin-3-one,
2,2,4,4-tetramethyl-6-(pyrazolo[1,5-a]pyridin-4-yl)-2,3,4,7,8,9-hexahydro-1H-cyclopenta[h]quinolin-3-one,
2,2,4,4-tetramethyl-6-([1,2,4]triazolo[4,3-a]pyridin-5-yl)-2,3,4,7,8,9-hexahydro-1H-cyclopenta[h]quinolin-3-one,
6-(imidazo[1,2-a]pyrazin-5-yl)-2,2,4,4-tetramethyl-2,3,4,7,8,9-hexahydro-1H-cyclopenta[h]quinolin-3-one,
2,2,4,4-tetramethyl-6-(thieno[2,3-b]pyridin-3-yl)-2,3,4,7,8,9-hexahydro-1H-cyclopenta[h]quinolin-3-one,
2,2,4,4-tetramethyl-6-(quinolin-5-yl)-2,3,4,7,8,9-hexahydro-1H-cyclopenta[h]quinolin-3-one,
2,2,4,4-tetramethyl-6-([1,8]naphthyridin-4-yl)-2,3,4,7,8,9-hexahydro-1H-cyclopenta[h]quinolin-3-one,
6-(3,5-dimethylisoxazol-4-yl)-2,2,4,4-tetramethyl-3-methylene-2,3,4,7,8,9-hexahydro-1H-cyclopenta[h]quinoline,
6-(imidazo[1,2-a]pyridin-5-yl)-2,2,4,4-tetramethyl-3-methylene-2,3,4,7,8,9-hexahydro-1H-cyclopenta[h]quinoline, 2,2,4,4-tetramethyl-3-methylene-6-([1,8]naphthyridin-4-yl)-2,3,4,7,8,9-hexahydro-1H-cyclopenta[h]quinoline, 2,2,4,4-tetramethyl-3-methylene-6-([1,2,4]triazolo[4,3-a]pyridin-5-yl)-2,3,4,7,8,9-hexahydro-1H-yclopenta[h]quinoline, 6-(3,5-dimethyl-3H-imidazol-4-yl)-2,2,4,4-tetramethyl-3-methylene-2,3,4,7,8,9-hexahydro-1H-cyclopenta[h]quinoline, 2,2,4,4-tetramethyl-6-([1,8]naphthyridin-4-yl)-1,2,3,4,8,9-hexahydro-furo[2,3-h]quinolin-3-one or 2,2,4,4-tetramethyl-6-([1,8]naphthyridin-4-yl)-1,2,3,4-tetrahydro-furo[2,3-h]quinolin-3-one, or a pharmaceutically acceptable salt thereof, or a hydrate thereof, (6) a condensed tetrahydroquinoline compound represented by the following formula (I)

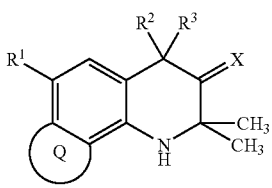

(I)

wherein $R^1$ is optionally substituted $C_6$-$C_{10}$ aryl, optionally substituted 5- or 6-membered heterocyclic aryl or optionally substituted bicyclic heteroaryl, $R^2$, and $R^3$ may be the same or different and each independently is a hydrogen atom or $C_1$-$C_6$ alkyl, ring Q is the following formula (II-a), (II-b) or (II-c),

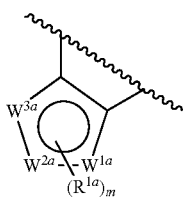

II-a

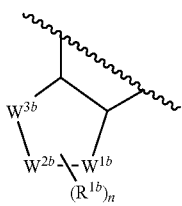

II-b

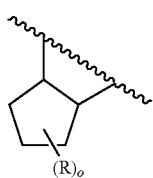

II-c wherein, m, n and o may be the same or different and each independently is 0 or 1, R, $R^{1a}$, and $R^{1b}$ may be the same or different and each independently is a hydrogen atom, optionally substituted $C_1$-$C_6$ alkyl, optionally substituted $C_1$-$C_{10}$ aryl or optionally substituted aryl-$C_1$-$C_6$ alkyl, $W^{1a}$, $W^{2a}$ and $W^{3a}$ are the same or different and each independently is —$CR^{1a}$—, a nitrogen atom, a sulfur atom or an oxygen atom, $W^{1b}$ and Web are the same or different and each independently is —$CHR^{1b}$—, —CO—, a nitrogen atom or an oxygen atom, $W^{3b}$ is —$CHR^{1b}$—, —CO—, a nitrogen atom, a sulfur atom or an oxygen atom, wherein at least one of $W^{1a}$, $W^{2a}$ and $W^{3a}$, or $W^{1b}$, $W^b$ and $W^{3b}$ is =$CH_2$—, and X is =$CH_2$ or an oxygen atom, or a pharmaceutically acceptable salt thereof, or a hydrate thereof, (7) the condensed tetrahydroquinoline compound of the aforementioned (6), wherein $R^1$ is the formula (III-a)

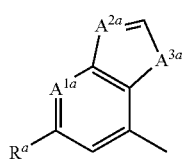

III-a wherein $R^a$ is $C_1$-$C_6$ alkyl or a halogen atom, $A^{1a}$ and $A^{2a}$ are the same or different and each independently is —N= or —CH=, $A^{3a}$ is —NH— or —O—, the formula (III-b)

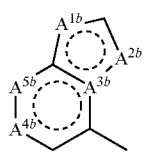

III-b wherein $A^{1b}$ and $A^{2b}$ are the same or different and each independently is —NH—, —N= or —CH=, $A^{3b}$ is a nitrogen atom or a carbon atom, $A^{4b}$ and $A^{5b}$ are the same or different and each independently is a nitrogen atom or —$CR^b$=, $R^b$ is a hydrogen atom, $C_1$-$C_6$ alkyl or a halogen atom, wherein at least two of $A^{1b}$, $A^{2b}$, $A^{3b}$, $A^{4b}$ and $A^{5b}$ are a carbon atom, —CH= or —$CR^b$=, the formula (III-c)

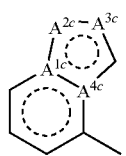

III-c wherein $A^{1c}$ and $A^{4c}$ are the same or different and each independently is a nitrogen atom or a carbon atom, $A^{2c}$ is —NH—, —N= or —CH=, $A^c$ is —N= or —CH=, wherein $A^{1c}$ and $A^{4c}$ are not simultaneously nitrogen atoms, the formula (III-d)

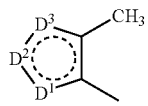

III-d wherein $D^1$ is —S—, —$C(R^{d1})$= or —$N(R^{d2})$—, $D^2$ is —S—, —$C(R^{d2})$= or —N=, $D^3$ is —O—, —S—, —C(R$^{d2}$)= or —N=, R$^{d1}$ is a hydrogen atom or C$_1$-C$_6$ alkoxy, R$^{d2}$ is a hydrogen atom, cyano or C$_1$-C$_6$ alkyl, provided that when any of D$^1$, D$^2$ and D$^3$ is —S— or —O—, the other two are not —O— or —S—,
the formula (III-e)

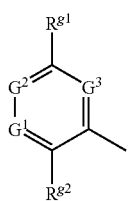

wherein G$^1$ is —N= or —C(R$^{g3}$)=, G$^2$ and G$^3$ are the same or different and each independently is —N= or —CH=, R$^{g1}$ is a hydrogen atom, a halogen atom or C$_1$-C$_6$ alkyl, R$^{g2}$ is a halogen atom, C$_1$-C$_6$ alkyl or C$_1$-C$_6$ alkoxy, R$^{g3}$ is a hydrogen atom or a halogen atom, wherein two of G$^1$-G$^3$ are —C(R$^{g3}$)=, naphthyridine, thienopyridine, phthalazine, or phenyl optionally substituted by 1 or 2 groups selected from the group consisting of a hydroxyl group, a halogen atom, C$_1$-C$_6$ alkyl and C$_1$-C$_6$ alkoxy, or a pharmaceutically acceptable salt thereof, or a hydrate thereof, (8) the condensed tetrahydroquinoline compound of the aforementioned (6), wherein R$^1$ is the formula (III-d), naphthyridine, thienopyridine or phthalazine, and ring Q is the formula (II-b), or a pharmaceutically acceptable salt thereof, or a hydrate thereof, (9) the condensed tetrahydroquinoline compound of the aforementioned (6), which is
6-(2-chloro-4-hydroxyphenyl)-2,2,4,4-tetramethyl-2,3,4,7,8,9-hexahydro-1H-cyclopenta[h]quinolin-3-one,
6-(3,5-dimethylisoxazol-4-yl)-2,2,4,4-tetramethyl-2,3,4,7,8,9,-hexahydro-1H-cyclopenta[h]quinolin-3-one,
6-(3,5-dimethyl-3H-imidazol-4-yl)-2,2,4,4-tetramethyl-2,3,4,7,8,9-hexahydro-1H-cyclopenta[h]quinolin-3-one,
6-(3,5-dimethyl-3H-[1,2,3]triazol-4-yl)-2,2,4,4-tetramethyl-2,3,4,7,8,9-hexahydro-1H-cyclopenta[h]quinolin-3-one,
6-(2-cyano-3-methylthiophen-4-yl)-2,2,4,4-tetramethyl-2,3,4,7,8,9-hexahydro-1H-cyclopenta[h]quinolin-3-one,
2,2,4,4-tetramethyl-6-(3-methylpyridin-4-yl)-2,3,4,7,8,9-hexahydro-1H-cyclopenta[h]quinolin-3-one,
6-(2-chloropyridin-3-yl)-2,2,4,4-tetramethyl-2,3,4,7,8,9-hexahydro-1H-cyclopenta[h]quinolin-3-one,
6-(5-fluoro-2-methoxypyridin-3-yl)-2,2,4,4-tetramethyl-2,3,4,7,8,9-hexahydro-1H-cyclopenta[h]quinolin-3-one,
6-(2,5-dimethylpyridin-4-yl)-2,2,4,4-tetramethyl-2,3,4,7,8,9-hexahydro-1H-cyclopenta[h]quinolin-3-one,
6-(1H-indol-7-yl)-2,2,4,4-tetramethyl-2,3,4,7,8,9-hexahydro-1H-cyclopenta[h]quinolin-3-one,
6-(5-fluoro-1H-indol-7-yl)-2,2,4,4-tetramethyl-2,3,4,7,8,9-hexahydro-1H-cyclopenta[h]quinolin-3-one,
6-(1H-benzimidazol-4-yl)-2,2,4,4-tetramethyl-2,3,4,7,8,9-hexahydro-1H-cyclopenta[h]quinolin-3-one,
2,2,4,4-tetramethyl-6-(1H-pyrrolo[3,2-b]pyridin-7-yl)-2,3,4,7,8,9-hexahydro-1H-cyclopenta[h]quinolin-3-one,
6-(imidazo[1,2-a]pyridin-5-yl)-2,2,4,4-tetramethyl-2,3,4,7,8,9-hexahydro-1H-cyclopenta[h]quinolin-3-one,
6-(1H-indazol-4-yl)-2,2,4,4-tetramethyl-2,3,4,7,8,9-hexahydro-1H-cyclopenta[h]quinolin-3-one,
2,2,4,4-tetramethyl-6-(pyrazolo[1,5-a]pyridin-4-yl)-2,3,4,7,8,9-hexahydro-1H-cyclopenta[h]quinolin-3-one,
2,2,4,4-tetramethyl-6-([1,2,4]triazolo[4,3-a]pyridin-5-yl)-2,3,4,7,8,9-hexahydro-1H-cyclopenta[h]quinolin-3-one,
6-(imidazo[1,2-a]pyrazin-5-yl)-2,2,4,4-tetramethyl-2,3,4,7,8,9-hexahydro-1H-cyclopenta[h]quinolin-3-one,
2,2,4,4-tetramethyl-6-(thieno[2,3-b]pyridin-3-yl)-2,3,4,7,8,9-hexahydro-1H-cyclopenta[h]quinolin-3-one,
2,2,4,4-tetramethyl-6-(quinolin-5-yl)-2,3,4,7,8,9-hexahydro-1H-cyclopenta[h]quinolin-3-one,
2,2,4,4-tetramethyl-6-([1,8]naphthyridin-4-yl)-2,3,4,7,8,9-hexahydro-1H-cyclopenta[h]quinolin-3-one,
2,2,4,4-tetramethyl-6-(phthalazin-5-yl)-2,3,4,7,8,9-hexahydro-1H-cyclopenta[h]quinolin-3-one,
6-(3,5-dimethylisoxazol-4-yl)-2,2,4,4-tetramethyl-3-methylene-2,3,4,7,8,9-hexahydro-1H-cyclopenta[h]quinoline,
6-(imidazo[1,2-a]pyridin-5-yl)-2,2,4,4-tetramethyl-3-methylene-2,3,4,7,8,9-hexahydro-1H-cyclopenta[h]quinoline,
2,2,4,4-tetramethyl-3-methylene-6-([1,8]naphthyridin-4-yl)-2,3,4,7,8,9-hexahydro-1H-cyclopenta[h]quinoline,
2,2,4,4-tetramethyl-3-methylene-6-([1,2,4]triazolo[4,3-a]pyridin-5-yl)-2,3,4,7,8,9-hexahydro-1H-cyclopenta[h]quinoline,
6-(imidazo[1,2-a]pyrazin-5-yl)-2,2,4,4-tetramethyl-3-methylene-2,3,4,7,8,9-hexahydro-1H-cyclopenta[h]quinoline,
6-(3,5-dimethyl-3H-[1,2,3]triazol-4-yl)-2,2,4,4-tetramethyl-3-methylene-2,3,4,7,8,9-hexahydro-1H-cyclopenta[h]quinoline or
6-(3,5-dimethyl-3H-imidazol-4-yl)-2,2,4,4-tetramethyl-3-methylene-2,3,4,7,8,9-hexahydro-1H-cyclopenta[h]quinoline,
or a pharmaceutically acceptable salt thereof, or a hydrate thereof,

(10) the condensed tetrahydroquinoline compound of the aforementioned (6), which is
6-(3,5-dimethylisoxazol-4-yl)-2,2,4,4-tetramethyl-2,3,4,7,8,9,-hexahydro-1H-cyclopenta[h]quinolin-3-one,
6-(3,5-dimethyl-3H-[1,2,3]triazol-4-yl)-2,2,4,4-tetramethyl-2,3,4,7,8,9-hexahydro-1H-cyclopenta[h]quinolin-3-one,
2,2,4,4-tetramethyl-6-(3-methylpyridin-4-yl)-2,3,4,7,8,9-hexahydro-1H-cyclopenta[h]quinolin-3-one,
6-(5-fluoro-2-methoxypyridin-3-yl)-2,2,4,4-tetramethyl-2,3,4,7,8,9-hexahydro-1H-cyclopenta[h]quinolin-3-one,
6-(2,5-dimethylpyridin-4-yl)-2,2,4,4-tetramethyl-2,3,4,7,8,9-hexahydro-1H-cyclopenta[h]quinolin-3-one,
6-(1H-indol-7-yl)-2,2,4,4-tetramethyl-2,3,4,7,8,9-hexahydro-1H-cyclopenta[h]quinolin-3-one,
2,2,4,4-tetramethyl-6-(1H-pyrrolo[3,2-b]pyridin-7-yl)-2,3,4,7,8,9-hexahydro-1H-cyclopenta[h]quinolin-3-one,
6-(imidazo[1,2-a]pyridin-5-yl)-2,2,4,4-tetramethyl-2,3,4,7,8,9-hexahydro-1H-cyclopenta[h]quinolin-3-one,
6-(1H-indazol-4-yl)-2,2,4,4-tetramethyl-2,3,4,7,8,9-hexahydro-1H-cyclopenta[h]quinolin-3-one,
2,2,4,4-tetramethyl-6-(pyrazolo[1,5-a]pyridin-4-yl)-2,3,4,7,8,9-hexahydro-1H-cyclopenta[h]quinolin-3-one,
2,2,4,4-tetramethyl-6-([1,2,4]triazolo[4,3-a]pyridin-5-yl)-2,3,4,7,8,9-hexahydro-1H-cyclopenta[h]quinolin-3-one,
6-(imidazo[1,2-a]pyrazin-5-yl)-2,2,4,4-tetramethyl-2,3,4,7,8,9-hexahydro-1H-cyclopenta[h]quinolin-3-one,
2,2,4,4-tetramethyl-6-(thieno[2,3-b]pyridin-3-yl)-2,3,4,7,8,9-hexahydro-1H-cyclopenta[h]quinolin-3-one,
2,2,4,4-tetramethyl-6-(quinolin-5-yl)-2,3,4,7,8,9-hexahydro-1H-cyclopenta[h]quinolin-3-one,
2,2,4,4-tetramethyl-6-([1,8]naphthyridin-4-yl)-2,3,4,7,8,9-hexahydro-1H-cyclopenta[h]quinolin-3-one,
6-(3,5-dimethylisoxazol-4-yl)-2,2,4,4-tetramethyl-3-methylene-2,3,4,7,8,9-hexahydro-1H-cyclopenta[h]quinoline,
6-(imidazo[1,2-a]pyridin-5-yl)-2,2,4,4-tetramethyl-3-methylene-2,3,4,7,8,9-hexahydro-1H-cyclopenta[h]quinoline, 2,2,4,4-tetramethyl-3-methylene-6-([1,8]naphthyridin-4-yl)-2,3,4,7,8,9-hexahydro-1H-cyclopenta[h]quinoline,
2,2,4,4-tetramethyl-3-methylene-6-([1,2,4]triazolo[4,3-a]pyridin-5-yl)-2,3,4,7,8,9-hexahydro-1H-cyclopenta[h]quinoline or
6-(3,5-dimethyl-3H-imidazol-4-yl)-2,2,4,4-tetramethyl-3-methylene-2,3,4,7,8,9-hexahydro-1H-cyclopenta[h]quinoline,
or a pharmaceutically acceptable salt thereof, or a hydrate thereof,
(11) a pharmaceutical composition comprising the condensed tetrahydroquinoline compound of the aforementioned (1) or (6) or a pharmaceutically acceptable salt thereof, or a hydrate thereof, and a pharmaceutically acceptable carrier,
(12) a therapeutic drug for a central nervous system-related disease, comprising the condensed tetrahydroquinoline compound of the aforementioned (1) or (6) or a pharmaceutically acceptable salt thereof, or a hydrate thereof as an active ingredient,
(13) the therapeutic drug of the aforementioned (12), wherein the central nervous system-related disease is an anxiety disorder, depression, psychotic major depression or a post-traumatic stress disorder.

Effect of the Invention

The condensed tetrahydroquinoline compound of the present invention, a pharmaceutically acceptable salt thereof, and a hydrate thereof (hereinafter sometimes to be referred to as the compound of the present invention) have a superior GR antagonist action, useful as therapeutic drugs for the diseases relating to GR, for example, depression, psychotic major depression, bipolar affective disorder, posttraumatic stress disorder, anxiety disorder, schizophrenia, Alzheimer's disease and the like, and promotes development as a pharmaceutical product of the compound.

BEST MODE FOR CARRYING OUT THE INVENTION

Next, the production methods of the compound of the present invention are explained.
The condensed tetrahydroquinoline compound represented by the formula (I) can be produced according to various methods such as the methods shown by the following production methods 1-7.
Production Method 1
In the formula (I), a compound wherein $R^2$ is methyl can be produced according to a method shown below.

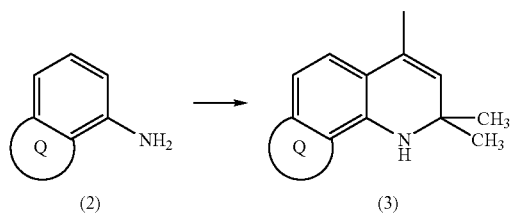

wherein Q is as defined above.
An aniline compound of the formula (2) can be led to a condensed dihydroquinoline compound represented by the formula (3) by the Scraup reaction. In the presence of a catalyst such as iodine, scandium trifluoromethanesulfonate, indium trifluoromethanesulfonate, ytterbium trifluoromethanesulfonate, indium chloride and the like, an additive such as hydrochloric acid, catechol and the like is added as necessary, and the mixture is stirred with heating with acetone or methyloxide in a reaction solvent (Tetrahedron Lett., 3907, 43, 2002, J. Am. Chem. Soc., 2805, 55, 1933 etc.).

The reaction solvent may be any as long as it does not inhibit the reaction and examples thereof include acetone, N,N-dimethylformamide (hereinafter to be referred to as DMF), N,N-dimethylacetamide (hereinafter to be referred to as DMA), dimethyl sulfoxide (hereinafter to be referred to as DMSO), dioxane, tetrahydrofuran (hereinafter to be referred to as THF), acetonitrile, chloroform (hereinafter to be referred to as $CHCl_3$), methylene chloride (hereinafter to be referred to as $CH_2Cl_2$), dichloroethane, ethyl acetate, dimethoxyethane and the like. In addition, a mixed solvent thereof may be used.

The kind and amount of use of the catalyst and additive can be appropriately determined according to the compound of the formula (2) to be subjected to the reaction.

The reaction temperature and reaction time may be appropriately determined according to the compound to be subjected to the reaction and reaction solvent. Generally, the reaction can be performed at about −78° C. to 100° C. for several dozen minutes to 5 days.

After completion of the reaction, general work-up is performed to give a compound represented by the formula (3). After the completion of any or all of the aforementioned reactions, the object compound can be recovered from the reaction mixture by a conventional method. For example, one appropriate method includes the following steps: the reaction mixture is poured into water, and the mixture is extracted with an organic solvent. The organic layer is washed with water and dried over a desiccant such as anhydrous magnesium sulfate, and the solvent is evaporated. The thus-obtained object compound can be further purified where necessary by a conventional method such as recrystallization, reprecipitation, various chromatography methods (particularly, column chromatography) and the like.

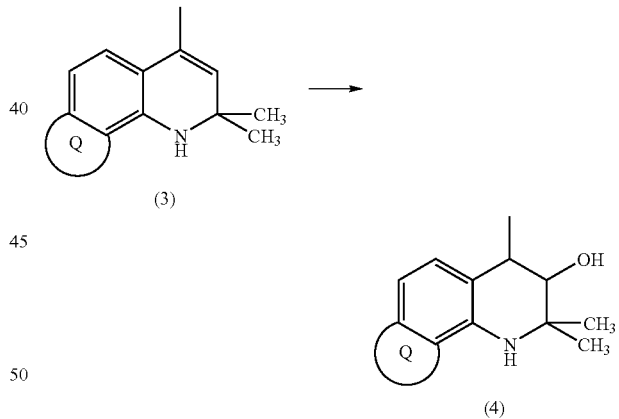

wherein Q is as defined above.
Condensed dihydroquinoline compound (3) is once led to a boron compound with a borohydride reagent, and oxidized with an oxidation reagent such as hydrogen peroxide and the like in the presence of a base, whereby a condensed tetrahydroquinolinol compound represented by the formula (4) can be obtained.

Examples of the borohydride reagent include borane, borabicyclo[3.3.1]nonane, catecholborane, thexylborane and the like.

Examples of the base include inorganic bases such as NaOH, KOH and the like.

The kind and amount of use of the borohydride reagent and base can be appropriately determined according to the compound of the formula (3) to be subjected to the reaction.

The reaction solvent in each step may be any as long as it does not inhibit the reaction and examples thereof include dioxane, THF, 1,2-dichloroethane, benzene, toluene, diethyl ether and the like.

The reaction temperature and reaction time in each step can be appropriately determined according to the compound to be subjected to the reaction and reaction solvent. Generally, the reaction can be performed at about 0° C.—refluxing temperature of the solvent for several dozen minutes to 48 hr.

After completion of the reaction, general work-up is performed to give a compound represented by the formula (4).

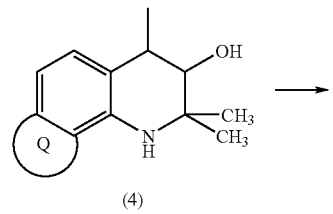

(4)

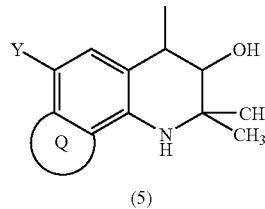

(5)

wherein Q is as defined above, and Y is a halogen substituent such as bromine, iodine and the like.

The method for obtaining formula (5) includes reacting a halogenation reagent such as bromine, iodine, pyridinium hydrobromide perbromide and the like in a reaction solvent.

The kind and amount of use of the halogenation reagent can be appropriately determined according to the compound of the formula (4) to be subjected to the reaction.

The reaction solvent may be any as long as it does not inhibit the reaction and examples thereof include DMF, DMA, DMSO, pyridine, dioxane, THF, acetonitrile, $CHCl_3$, $CH_2Cl_2$, dichloroethane, benzene, ethyl acetate, diethyl ether, dimethoxyethane and the like. In addition, a mixed solvent thereof may be used.

The reaction temperature and reaction time can be appropriately determined according to the compound to be subjected to the reaction and reaction solvent. Generally, the reaction can be performed at about −78° C. to 100° C. for several dozen minutes to 5 days.

After completion of the reaction, general work-up is performed to give a compound represented by the formula (5).

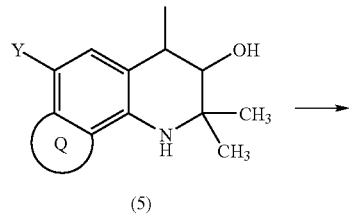

(5)

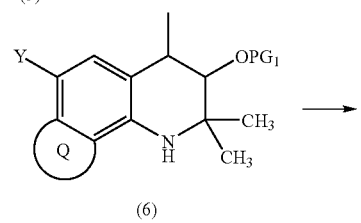

(6)

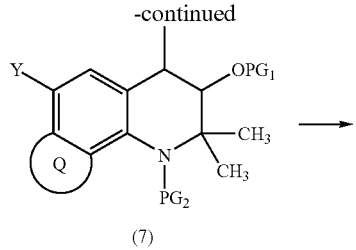

(7)

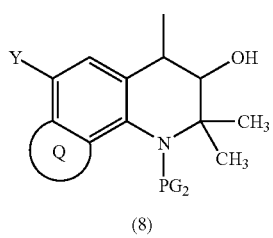

(8)

wherein each symbol is as defined above, and PG1 and PG2 are protecting groups.

To synthesize, under the following reaction conditions, a compound represented by the formula (8) wherein an appropriate protecting group (PG2) is introduced into the nitrogen atom, compound (6) wherein the hydroxyl group of compound (5) is protected by protecting group (PG1) was once synthesized, then compound (7) wherein a protecting group (PG2) is introduced into the nitrogen atom was obtained, and then PG1 was removed to give compound (8).

Examples of the protecting group (PG2) include substituted benzyl such as benzyl, p-chlorobenzyl, m-trifluoromethylbenzyl, α-phenylethyl, benzhydryl, trityl and the like; aliphatic acyl such as formyl, acetyl, propionyl, butyryl, valeryl, hexanoyl, pivaloyl and the like; halogen-substituted aliphatic acyl such as chloroacetyl, trifluoroacetyl and the like; aromatic acyl optionally having substituent(s) such as benzoyl, toluoyl, xyloyl, naphthoyl, phthaloyl and the like; aralkylacyl optionally having substituent(s) such as phenylacetyl, 3-phenylpropionyl, 3-(p-methoxyphenyl)propionyl, 3-(p-chlorophenyl)propionyl and the like; aromatic hetero ring-aliphatic acyl optionally having substituent(s) such as thienylacetyl, imidazolylacetyl, furylacetyl, triazolylacetyl, thiadiazolylpropionyl and the like; aryloxy aliphatic acyl optionally having substituent(s) such as phenoxyacetyl, phenoxypropionyl, and the like; $C_1$-$C_6$ alkoxycarbonyl such as methoxycarbonyl, ethoxycarbonyl, tert-butoxycarbonyl, hexyloxycarbonyl and the like; halogen-substituted $C_1$-$C_6$ alkoxycarbonyl such as chloromethoxycarbonyl, trichloroethoxycarbonyl and the like; aliphatic acyloxymethoxycarbonyl such as acetoxymethoxycarbonyl, (1-acetoxyethyl)oxycarbonyl, propionyloxymethoxycarbonyl, pivaloyloxymethoxycarbonyl, butyryloxymethoxycarbonyl and the like; alkenyloxycarbonyl such as allyloxycarbonyl and the like; aryloxycarbonyl optionally having substituent(s) such as phenoxycarbonyl, naphthyloxycarbonyl and the like; arylglyoxyloyl optionally having substituent(s) such as phenoxyglyoxyloyl, naphthylglyoxyloyl and the like; substituted benzyloxycarbonyl such as benzyloxycarbonyl, phenethyloxycarbonyl, p-nitrobenzyloxycarbonyl, p-methoxybenzyloxycarbonyl and the like; $C_1$-$C_6$ alkylsulfonyl such as methylsulfonyl, ethylsulfonyl, propylsulfonyl, pentylsulfonyl and the like; halogen-substituted $C_1$-$C_6$ alkylsulfonyl such as trifluoromethylsulfonyl and the like; aralkylsulfonyl optionally having substituent(s) such as benzylsulfonyl, p-chlorobenzylsulfonyl, phenethylsulfonyl and the like; arylsulfonyl optionally having substituent(s)

such as phenylsulfonyl, p-chlorophenylsulfonyl, tolylsulfonyl, naphthylsulfonyl, etc. and the like.

Examples of the protecting group (PG1) include silyl such as tert-butyldimethylsilyl, tert-butyldiphenylsilyl and the like; tetrahydropyranyl, trimethylsilylethoxymethyl and the like.

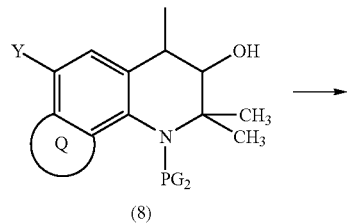

(8)

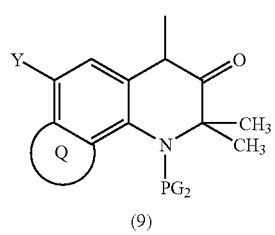

(9)

wherein each symbol is as defined above.

The condensed tetrahydroquinolinone compound represented by the formula (9) is obtained by oxidizing compound (8) with an oxidant in a reaction solvent.

As the oxidant, pyridinium chlorochromate, Dess-Martin reagent, 2-iodoxybenzoic acid and the like can be used. The kind and amount of use of the oxidant can be appropriately determined according to the compound of the formula (8) to be subjected to the reaction.

The reaction solvent may be any as long as it does not inhibit the reaction and examples thereof include DMF, DMA, DMSO, dioxane, THF, acetonitrile, $CHCl_3$, $CH_2Cl_2$, dichloroethane, benzene, ethyl acetate, diethyl ether, dimethoxyethane and the like. In addition, a mixed solvent thereof may be used.

The reaction temperature and reaction time can be appropriately determined according to the compound to be subjected to the reaction and reaction solvent. Generally, the reaction can be performed at about −78° C. to 100° C. for several dozen minutes to 5 days.

After completion of the reaction, general work-up is performed to give a compound represented by the formula (9).

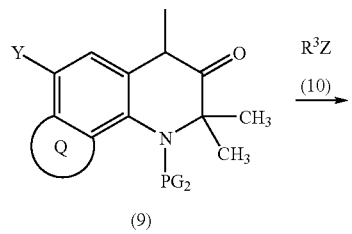

(9)

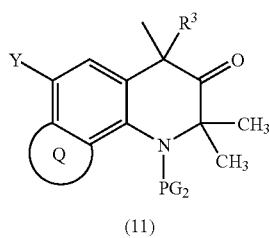

(11)

wherein each symbol is as defined above, and Z is a leaving group.

The compound represented by the formula (11) can be produced by reacting a compound of the formula (9) with a compound of the formula (10) preferably in the presence of a base.

Examples of Z include a chlorine atom, a bromine atom or an iodine atom; methanesulfonyl, ethanesulfonyl, benzenesulfonyl and the like; organic sulfonyloxy such as methanesulfonyloxy, trifluoromethanesulfonyloxy, p-toluenesulfonyloxy and the like; 1-imidazolyl and the like.

Examples of the base include organic metal bases such as lithiumbis(trimethylsilyl)amide, butyllithium and the like; inorganic bases such as potassium carbonate, sodium carbonate, sodium hydrogen carbonate, potassium hydroxide and the like.

Hexamethylphosphoramide, crown ether and the like may be added as additives.

The kind and amount of use of the base and additive can be appropriately determined according to the compounds of the formula (9) and the formula (10) to be subjected to the reaction. The base is generally used in an amount of 1 mol to molar excess, preferably 1 to 10 mol, per 1 mol of the compound of the formula (9).

The reaction solvent may be any as long as it does not inhibit the reaction and examples thereof include hexane, petroleum ether, cyclohexane, dioxane, THF, diethyl ether and the like. In addition, a mixed solvent thereof may be used.

The reaction temperature and reaction time can be appropriately determined according to the compound to be subjected to the reaction and reaction solvent. Generally, the reaction can be performed at about −78° C. to 100° C. for several dozen minutes to 24 hr.

After completion of the reaction, general work-up is performed to give a compound represented by the formula (11).

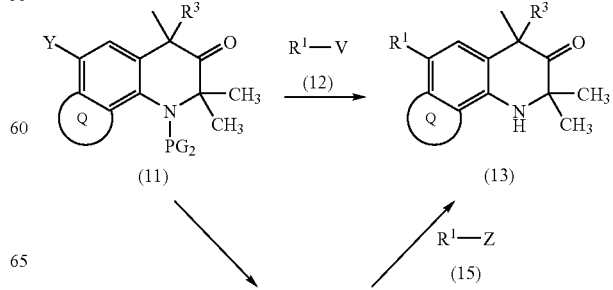

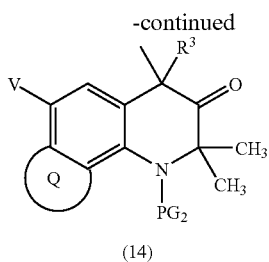

(14)

wherein each symbol is as defined above, Z is a leaving group, and V is boryl.

The compound represented by the formula (13) can be produced by reacting compound (11) with compound (12) according to general conditions for Suzuki reaction (in the presence of base and palladium catalyst) and removing the protecting group PG2.

Examples of the palladium catalyst include Pd(PPh$_3$)$_4$, PdCl$_2$(PPh$_3$)$_2$, PdCl$_2$(OAc)$_2$, Pd$_2$(dba)$_3$ (tris(dibenzylideneacetone)dipalladium), PdCl$_2$(dppf) [1,1'-bis(diphenylphosphino)ferrocene]dichloropalladium and the like.

The kind and amount of use of the catalyst can be appropriately determined according to the compound of the formula (11) or (12) to be subjected to the reaction. Depending on the compound to be reacted, a ligand, for example, additives such as 2-dicyclohexylphosphino-2',4',6'-triisopropylbiphenyl, 2-(dicyclohexylphosphino)biphenyl and the like, lithium chloride and the like can be added. The kind and amount of use of the ligand and additive can be appropriately determined according to the compound of the formula (11) or (12) to be subjected to the reaction.

Examples of the base include K$_3$PO$_4$, NaHCO$_3$, NaOEt, Na$_3$CO$_3$, K$_2$CO$_3$, Ba(OH)$_3$, Cs$_2$CO$_3$, CsF, NaOH, Ag$_2$CO$_3$ and the like. The reaction solvent may be any as long as it does not inhibit the reaction and examples thereof include DMF, DMA, DMSO, pyridine, dioxane, THF, acetonitrile, CHCl$_3$, CH$_2$Cl$_2$, dichloroethane, benzene, ethyl acetate, methanol, ethanol, isopropanol, diethyl ether and the like. In addition, a mixed solvent thereof or a mixed system with water may be used. The reaction temperature and reaction time can be appropriately determined according to the compound to be subjected to the reaction and reaction solvent. Generally, the reaction can be performed at about 0° C.—refluxing temperature of the solvent for several dozen minutes to 48 hr.

After completion of the reaction, general work-up is performed to give a compound represented by the formula (13).

Substituent V may be any as long as it is boryl applicable to Suzuki reaction and the like (Suzuki et al., Organic Synthesis via Boranes, Volume 3, Aldrich Chemical Company), preferably pinacol boryl and dihydroxy boryl.

It is also possible to convert compound (11) to a boryl derivative to give compound (14), and react compound (14) with compound (15).

The method for producing compound (14) includes reacting, in the presence of the aforementioned palladium catalyst and base, pinacol boryl such as bis(pinacolato)diboron, bis(neopentylglycolato)diboron, bis(hexyleneglycolato)diboron and the like with compound (11) in the aforementioned reaction solvent. Compound (13) can be obtained by reacting the obtained compound (14) with compound (15) under the aforementioned Suzuki reaction conditions and removing the protecting group PG2.

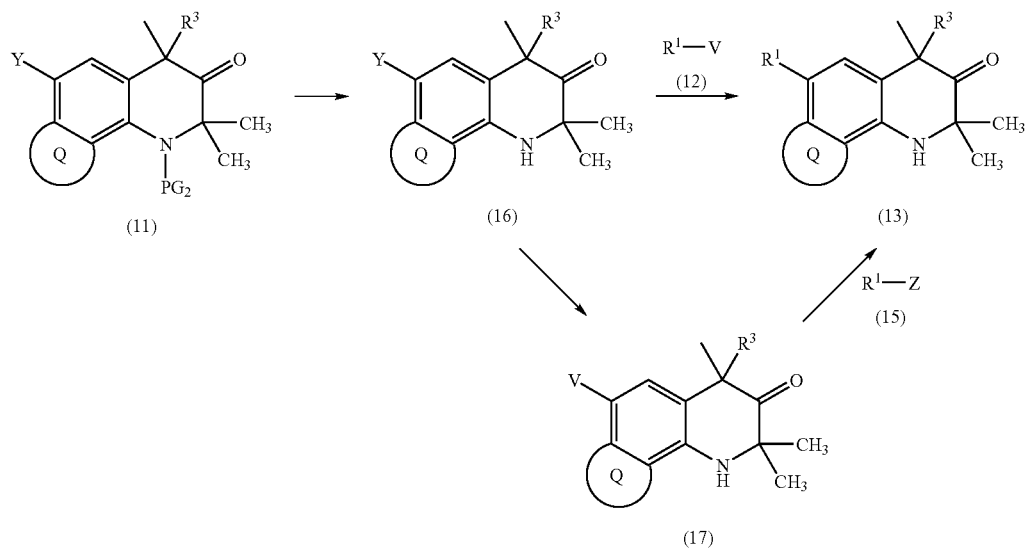

wherein each symbol is as defined above.

Compound (13) can also be obtained by first removing the protecting group PG2 of compound (11) to give compound (16), and subjecting the compound to the above-mentioned reaction. The reaction reagent, reaction conditions and reaction solvent can be selected from the above-mentioned respective reaction conditions.

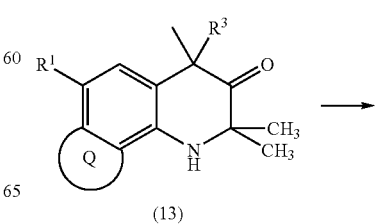

(13)

-continued

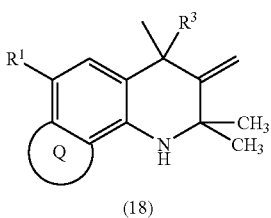

(18)

wherein each symbol is as defined above.

Compound (18) can be obtained by performing a Wittig reaction of compound (13) with methyltriphenylbromide in the presence of a base.

Examples of the base include organic metal bases such as potassium tert-butoxide, sodium tert-butoxide, potassium ethoxide, sodium ethoxide and the like.

The kind and amount of use of methyltriphenylbromide and base can be appropriately determined according to the compound of the formula (13) to be subjected to the reaction. The base is generally used in an amount of 1 mol to molar excess, preferably 1 to 10 mol, per 1 mol of the compound of the formula (2).

The reaction solvent may be any as long as it does not inhibit the reaction and examples thereof include DMF, DMA, DMSO, pyridine, dioxane, THF, acetonitrile, $CHCl_3$, $CH_2Cl_2$, dichloroethane, benzene, toluene, diethyl ether, dimethoxyethane and the like. In addition, a mixed solvent thereof may be used. The reaction temperature and reaction time can be appropriately determined according to the compound to be subjected to the reaction and reaction solvent. Generally, the reaction can be performed at about room temperature to 200° C. for several dozen minutes to 5 days.

After completion of the reaction, general work-up is performed to give a compound represented by the formula (18).

A compound of the formula (1) wherein $R^2$ is methyl can be produced according to a method including constructing a tetrahydroquinolinone skeleton shown below and thereafter constructing a new hetero ring.

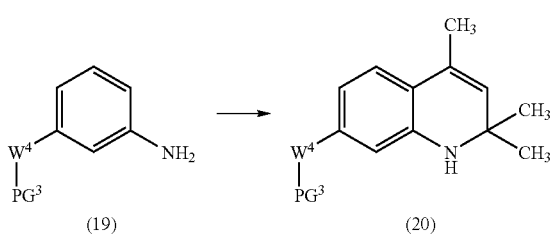

(19)  (20)

wherein $W^4$ is a nitrogen atom, a sulfur atom or an oxygen atom, and PG3 is a protecting group.

An aniline compound of the formula (19) can be led to a dihydroquinoline compound represented by the formula (20) by a Scraup reaction.

The kind of PG3 can be appropriately determined according to $W^4$. In the presence of a catalyst such as iodine, scandium trifluoromethanesulfonate, indium trifluoromethanesulfonate, ytterbium trifluoromethanesulfonate, indium chloride and the like, an additive such as hydrochloric acid, catechol and the like is added as necessary, and the mixture is stirred with heating with acetone or methyloxide in a reaction solvent. The reaction solvent may be any as long as it does not inhibit the reaction and examples thereof include acetone, DMF, DMA, DMSO, dioxane, THF, acetonitrile, $CHCl_3$, $CH_2Cl_2$, dichloroethane, ethyl acetate, dimethoxyethane and the like. In addition, a mixed solvent thereof may be used. The kind and amount of use of the catalyst and additive can be appropriately determined according to the compound of the formula (19) to be subjected to the reaction. The reaction temperature and reaction time can be appropriately determined according to the compound to be subjected to the reaction and reaction solvent. Generally, the reaction can be performed at about −78° C. to 100° C. for several dozen minutes to 5 days.

After completion of the reaction, general work-up is performed to give a compound represented by the formula (20).

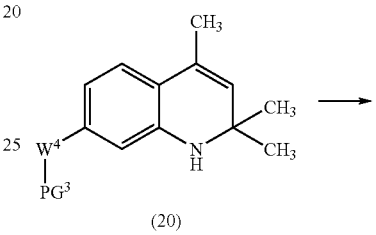

(20)

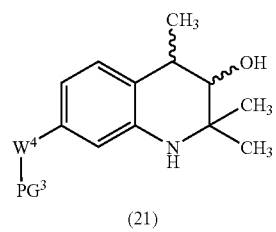

(21)

wherein each symbol is as defined above.

Dihydroquinoline compound (20) is once led to a boron compound with a borohydride reagent, and oxidized with an oxidation reagent such as hydrogen peroxide and the like in the presence of a base, whereby a tetrahydroquinolinol compound represented by the formula (21) can be obtained.

Examples of the borohydride reagent include borane, borabicyclo[3.3.1]nonane, catecholborane, thexylborane and the like. Examples of the base include inorganic bases such as sodium hydroxide, potassium hydroxide and the like. The kind and amount of use of the borohydride reagent and base can be appropriately determined according to the compound of the formula (20) to be subjected to the reaction. The reaction solution in each step may be any as long as it does not inhibit the reaction and examples thereof include dioxane, THF, 1,2-dichloroethane, benzene, toluene, diethyl ether and the like. The reaction temperature and reaction time in each step can be appropriately determined according to the compound to be subjected to the reaction and reaction solvent. Generally, the reaction can be performed at about 0° C.—refluxing temperature of the solvent for several dozen minutes to 48 hr.

After completion of the reaction, general work-up is performed to give a compound represented by the formula (21).

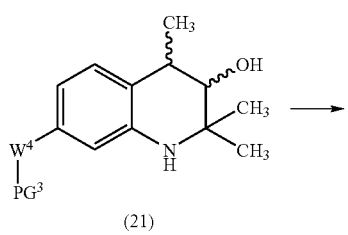

(21)

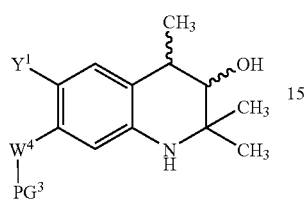

(22)

wherein $PG^3$ and $W^4$ are as defined above, and $Y^1$ is a halogen substituent such as bromine, iodine and the like.

The compound represented by the formula (22) is obtained by reacting a compound of the formula (21) with a halogenation reagent such as bromine, iodine, pyridinium hydrobromide perbromide and the like in a reaction solvent.

The kind and amount of use of the halogenation reagent can be appropriately determined according to the compound of the formula (21) to be subjected to the reaction. The reaction solvent may be any as long as it does not inhibit the reaction and examples thereof include DMF, DMA, DMSO, pyridine, dioxane, THF, acetonitrile, CHCl₃, CH₂Cl₂, dichloroethane, benzene, ethyl acetate, diethyl ether, dimethoxyethane and the like. In addition, a mixed solvent thereof may be used. The reaction temperature and reaction time can be appropriately determined according to the compound to be subjected to the reaction and reaction solvent. Generally, the reaction can be performed at about −78° C. to 100° C. for several dozen minutes to 5 days.

After completion of the reaction, general work-up is performed to give a compound represented by the formula (22).

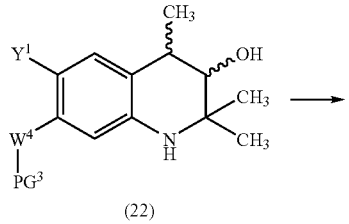

(22)

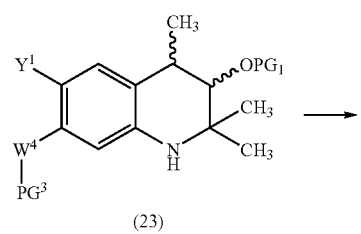

(23)

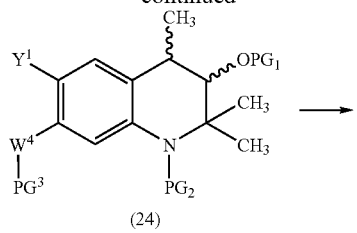

(24)

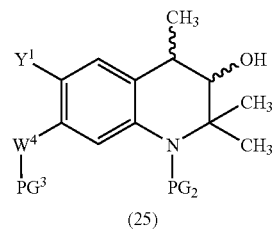

(25)

wherein each symbol is as defined above.

To synthesize a compound represented by the formula (25) wherein an appropriate protecting group PG2 is introduced into the nitrogen atom, compound (23) wherein the hydroxyl group of compound (22) is protected by protecting group PG1 is once synthesized, then compound (24) wherein a protecting group PG2 is introduced into the nitrogen atom is obtained, and then protecting group PG1 is removed to give compound (25).

The reaction solvent may be any as long as it does not inhibit the reaction and examples thereof include hexane, petroleum ether, cyclohexane, dioxane, THF, benzene, toluene, CH₂Cl₂, CHCl₃, dichloroethane, methanol, ethanol, DMF, DMA, DMSO, acetonitrile, ethyl acetate, diethyl ether, dimethoxyethane and the like. The reaction temperature and reaction time in each step can be appropriately determined according to the compound to be subjected to the reaction and reaction solvent. Generally, the reaction can be performed at −78° C. to 100° C. for several dozen minutes to 24 hr.

After completion of the reaction, general work-up is performed to give the object product.

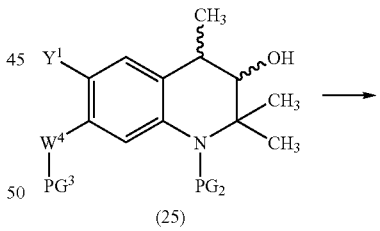

(25)

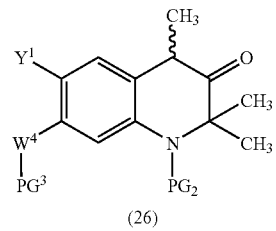

(26)

wherein each symbol is as defined above.

A tetrahydroquinoline compound represented by the formula (26) is obtained by oxidizing compound (25) with an oxidant in a reaction solution.

As the oxidant, pyridinium chlorochromate, Dess-Martin reagent, o-iodoxybenzoic acid and the like can be used. The kind and amount of use of the oxidant can be appropriately determined according to the compound of the formula (25) to be subjected to the reaction. The reaction solvent may be any as long as it does not inhibit the reaction and examples thereof include DMF, DMA, DMSO, dioxane, THF, acetonitrile, CH$_2$Cl$_2$, CHCl$_3$, dichloroethane, benzene, toluene, ethyl acetate, diethyl ether, dimethoxyethane and the like. In addition, a mixed solvent thereof may be used. The reaction temperature and reaction time can be appropriately determined according to the compound to be subjected to the reaction and reaction solvent. Generally, the reaction can be performed at about −78° C. to 100° C. for several dozen minutes to 5 days.

After completion of the reaction, general work-up is performed to give a compound represented by the formula (26).

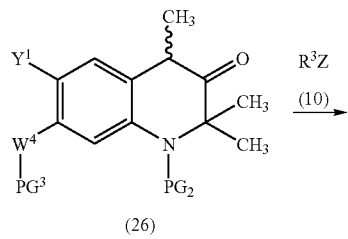

(26)

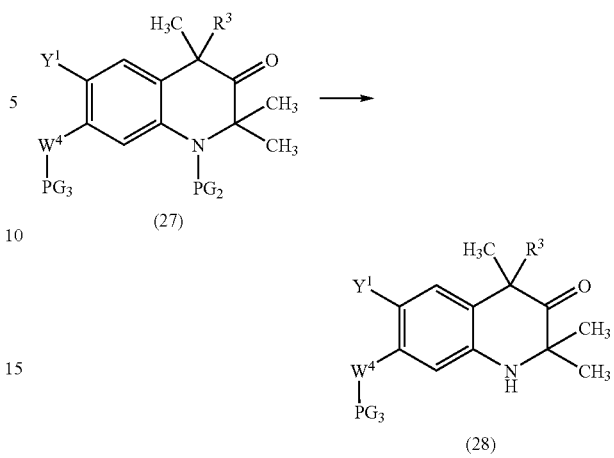

(27)

(28)

wherein each symbol is as defined above.

The compound represented by the formula (27) can be produced by reacting a compound of the formula (26) with a compound of the formula (10) preferably in the presence of a base.

Examples of the base include organic metal bases such as lithiumbis(trimethylsilyl)amide, butyllithium and the like; inorganic metal bases such as potassium carbonate, sodium carbonate, sodium hydroxide, potassium hydroxide and the like. Hexamethylphosphoramide, crown ether and the like may be added as additives. The kind and amount of use of the base and additive can be appropriately determined according to the compounds of the formulas (26) and (10) to be subjected to the reaction. The base is generally used in an amount of 1 mol to molar excess, preferably 1 mol to 10 mol, per 1 mol of the compound of the formula (26). The reaction solvent may be any as long as it does not inhibit the reaction and examples thereof include hexane, petroleum ether, cyclohexane, dioxane, THF, diethyl ether and the like. The reaction temperature and reaction time can be appropriately determined according to the compound to be subjected to the reaction and reaction solvent. Generally, the reaction can be performed at −78° C. to 100° C. for several dozen minutes to 24 hr.

After completion of the reaction, general work-up is performed to give a compound represented by the formula (27).

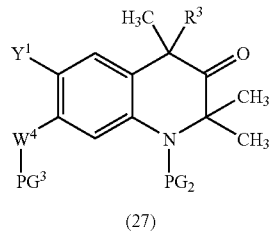

(27)

wherein each symbol is as defined above.

The compound represented by the formula (28) can be obtained by removing protecting groups (PG2 and PG3) of a compound of the formula (27).

The reaction solvent may be any as long as it does not inhibit the reaction and examples thereof include hexane, petroleum ether, cyclohexane, dioxane, THF, benzene, toluene, CH$_2$Cl$_2$, CHCl$_3$, dichloroethane, methanol, ethanol, DMF, DMA, DMSO, acetonitrile, ethyl acetate, diethyl ether, dimethoxyethane and the like. The reaction temperature and reaction time in each step can be appropriately determined according to the compound to be subjected to the reaction and reaction solvent. Generally, the reaction can be performed at −78° C. to 100° C. for several dozen minutes to 24 hr.

After completion of the reaction, general work-up is performed to give the object compound.

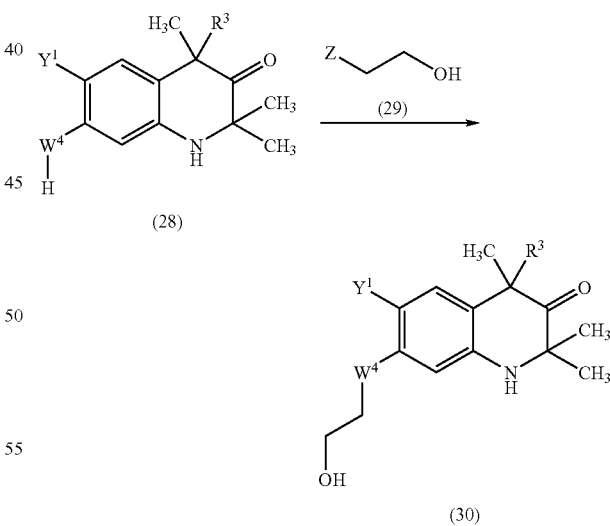

(28)

(30)

wherein each symbol is as defined above.

A compound represented by the formula (30) can be is obtained by reacting a compound of the formula (28) with a compound of the formula (29) preferably in the presence of a base.

Examples of the base include organic metal bases such as lithiumbis(trimethylsilyl)amide, butyllithium and the like; inorganic metal bases such as potassium carbonate, sodium carbonate, sodium hydroxide, potassium hydroxide and the like. Hexamethylphosphoramide, crown ether and the like may be added as additives. The kind and amount of use of the base and additive can be appropriately determined according to the compounds of the formulas (28) and (29) to be subjected to the reaction. The base is generally used in an amount of 1 mol to molar excess, preferably 1 mol to 10 mol, per 1 mol of the compound of the formula (28). The reaction solvent may be any as long as it does not inhibit the reaction and examples thereof include hexane, petroleum ether, cyclohexane, dioxane, THF, diethyl ether and the like. The reaction temperature and reaction time can be appropriately determined according to the compound to be subjected to the reaction and reaction solvent. Generally, the reaction can be performed at −78° C. to 100° C. for several dozen minutes to 24 hr.

After completion of the reaction, general work-up is performed to give a compound represented by the formula (30).

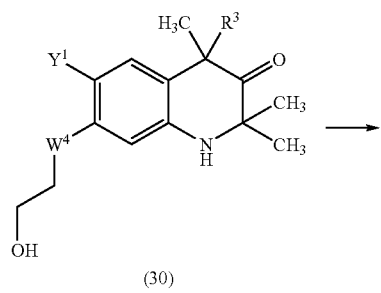

(30)

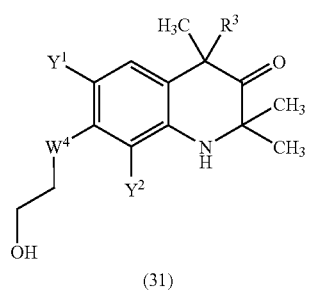

(31)

wherein $R^3$, $W^4$ and $Y^1$ are as defined above, and $Y^2$ is a halogen substituent such as bromine, iodine and the like.

The compound represented by the formula (31) is obtained by reacting a compound of the formula (30) with a halogenation reagent such as bromine, iodine, pyridinium hydrobromide perbromide and the like in a reaction solvent.

The kind and amount of use of the halogenation reagent can be appropriately determined according to the compound of the formula (30) to be subjected to the reaction. The reaction solvent may be any as long as it does not inhibit the reaction and examples thereof include DMF, DMA, DMSO, pyridine, dioxane, THF, acetonitrile, $CHCl_3$, $CH_2Cl_2$, dichloroethane, benzene, ethyl acetate, diethyl ether, dimethoxyethane and the like. In addition, a mixed solvent thereof may be used. The reaction temperature and reaction time can be appropriately determined according to the compound to be subjected to the reaction and reaction solvent. Generally, the reaction can be performed at about −78° C. to 100° C. for several dozen minutes to 5 days.

After completion of the reaction, general work-up is performed to give a compound represented by the formula (31).

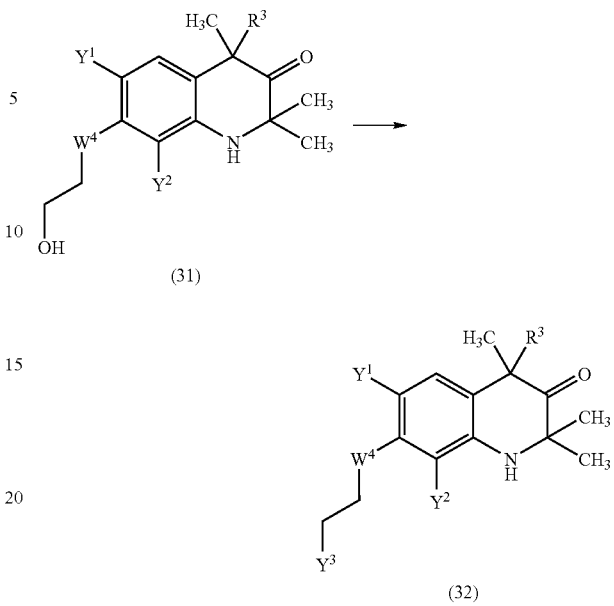

wherein $R^3$, $W^4$, $Y^1$ and $Y^2$ are as defined above, and $Y^3$ is a halogen substituent such as bromine, iodine and the like.

The compound represented by the formula (32) is obtained by halogenating a compound of the formula (31) with a halogenation reagent in a reaction solution.

Examples of the halogenation reagent include halogenated hydrogen such as hydrochloric acid, hydrobromic acid, hydroiodic acid and the like; halogenated phosphorus such as phosphorus trichloride, phosphorus pentachloride, phosphorus oxychloride and the like; halogen such as chlorine, bromine, iodine and the like; halogenated metal salt such as sodium bromide, sodium iodide, potassium iodide and the like; thionyl chloride, carbon tetrachloride-triphenylphosphine, carbon tetrabromide-triphenylphosphine, N-chlorosuccinic acid imide, N-bromosuccinic acid imide and the like. Furthermore, the halogenation reaction can be performed by converting the hydroxyl group to the corresponding methanesulfonyloxy group with methanesulfonyl chloride and the like, and then reacting the compound with a halogenation reagent such as sodium iodide and the like. The kind and amount of use of the halogenation reagent can be appropriately determined according to the compound of the formula (31) to be subjected to the reaction. The reaction solvent may be any as long as it does not inhibit the reaction and examples thereof include water, diethyl ether, THF, ethylene glycol dimethyl ether, DMF, DMA, DMSO, $CHCl_3$, $CH_2Cl_2$, dichloroethane, acetonitrile, benzene, toluene, xylene, acetone, 2-butanone and the like. In addition, a mixed solvent thereof may be used. The reaction temperature and reaction time can be appropriately determined according to the compound to be subjected to the reaction and reaction solvent. Generally, the reaction can be performed at about −78° C. to 100° C. for several dozen minutes to 24 hr.

After completion of the reaction, general work-up is performed to give a compound represented by the formula (32).

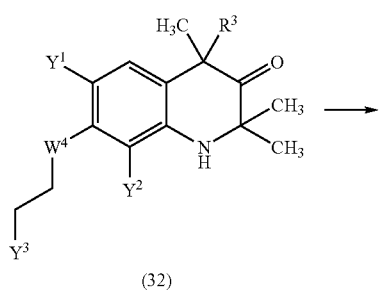

(32)

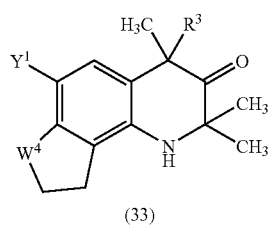

(33)

wherein each symbol is as defined above.

A condensed tetrahydroquinoline compound represented by the formula (33) can be obtained by intramolecular alkylation of a compound of the formula (32) with an organic metal reagent in a reaction solution.

Examples of the organic metal reagent include magnesium, isopropylmagnesium chloride, butyllithium and the like. 1,2-Dibromoethane, ethylmagnesium bromide, copper cyanide-lithium chloride and the like may be added as additives. The kind and amount of use of the organic metal reagent and additive can be appropriately determined according to the compound of the formula (32) to be subjected to the reaction. The organic metal reagent is generally used in an amount of 1 mol to molar excess, preferably 1 mol to 10 mol, per 1 mol of the compound of the formula (32). The reaction solvent may be any as long as it does not inhibit the reaction and examples thereof include hexane, pentane, petroleum ether, cyclohexane, dioxane, THF, diethyl ether and the like. In addition, a mixed solvent thereof may be used. The reaction temperature and reaction time can be appropriately determined according to the compound to be subjected to the reaction and reaction solvent. Generally, the reaction can be performed at −78° C. to 100° C. for several dozen minutes to 24 hr.

After completion of the reaction, general work-up is performed to give a compound represented by the formula (33).

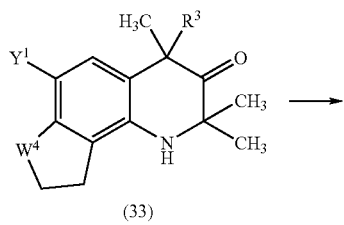

(33)

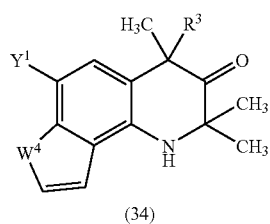

(34)

wherein each symbol is as defined above.

The compound represented by the formula (34) can be obtained by oxidizing a compound of the formula (33) with an oxidant.

Examples of the oxidant include 2,3-dichloro-5,6-dicyano-1,4-benzoquinone, tetrachloro-1,4-benzoquinone, nickel dioxide, manganese dioxide, palladium and the like. The kind and amount of use of the oxidant can be appropriately determined according to the compound of the formula (33) to be subjected to the reaction. The reaction solvent may be any as long as it does not inhibit the reaction and examples thereof include DMF, DMA, DMSO, dioxane, THF, acetonitrile, $CH_2Cl_2$, $CHCl_3$, dichloroethane, benzene, toluene, ethyl acetate, diethyl ether, dimethoxyethane and the like. The reaction temperature and reaction time can be appropriately determined according to the compound to be subjected to the reaction and reaction solvent. Generally, the reaction can be performed at about −78° C.—refluxing temperature of the solvent for several dozen minutes to 5 days.

After completion of the reaction, general work-up is performed to give a compound represented by the formula (26).

Compounds of the formulas (33) and (34) can be lead to a compound represented by the formula (13) by a method similar to that of the compound of the formula (11).

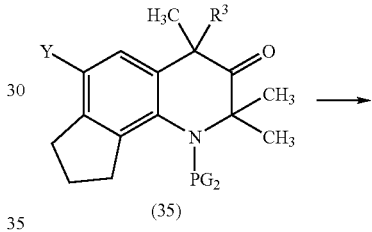

(35)

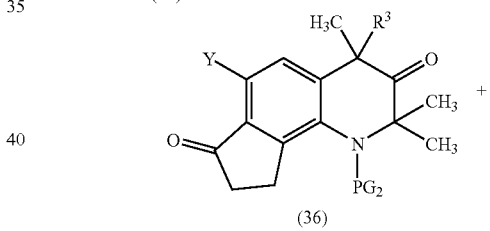

(36)

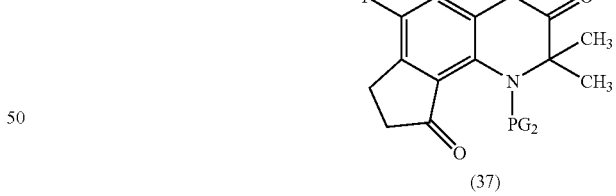

(37)

wherein each symbol is as defined above.

Compounds represented by the formulas (36) and (37) can be obtained by oxidizing a compound of the formula (35) with potassium permanganate in the presence of iron chloride.

The kind and amount of use of the reagent can be appropriately determined according to the compound of the formula (33) to be subjected to the reaction. The reaction solvent may be any as long as it does not inhibit the reaction and examples thereof include DMF, DMA, DMSO, dioxane, THF, acetonitrile, $CH_2Cl_2$, $CHCl_3$, dichloroethane, benzene, toluene, ethyl acetate, diethyl ether, dimethoxyethane and the like. The reaction temperature and reaction time can be appropriately determined according to the compound to be subjected to the reaction and reaction solvent. Generally, the reaction can be performed at about −78° C.—refluxing temperature of the solvent for several dozen minutes to 5 days.

After completion of the reaction, general work-up is performed to give the compounds represented by the formulas (36) and (37).

The compounds of the formulas (36) and (37) can be lead to a compound represented by the formula (13) by a method similar to that of the compound of the formula (11).

The condensed tetrahydroquinoline compound represented by the formula (I) and produced according to the aforementioned methods can be purified to a desired purity by a conventional purification means, for example, means such as concentration, extraction, chromatography, reprecipitation, recrystallization and the like. Moreover, a conventional salt-forming means can be applied as necessary to produce a pharmaceutically acceptable salt.

A pharmaceutical composition containing a condensed tetrahydroquinoline compound or a pharmaceutically acceptable salt thereof can be produced by adding a pharmaceutically acceptable carrier and additive to the condensed tetrahydroquinoline compound relating to the present invention or a pharmaceutically acceptable salt thereof, and formulating a preparation known to those of ordinary skill in the art, such as tablet, capsule, granule, fine granule, powder, injection and the like.

While various terms used alone or in combination in the present specification are explained below, the following explanation does not at all limit the present invention.

The "optionally substituted" means optionally having, as substituent(s), one or plural groups selected from a halogen atom, hydroxy, $C_1$-$C_6$ alkoxy, $C_1$-$C_6$ alkoxy substituted by a halogen atom, $C_2$-$C_6$ alkenyl, $C_6$-$C_{10}$ aryloxy, $C_1$-$C_6$ alkyl, $C_1$-$C_6$ alkyl substituted by a halogen atom, $C_3$-$C_7$ cycloalkyl, $C_6$-$C_{10}$ aryl, amino, $C_1$-$C_6$ alkylamino, $C_6$-$C_{10}$ arylamino, thiol, $C_1$-$C_6$ alkylthio, $C_6$-$C_{10}$ arylthio, carboxy or ester thereof or amide thereof, formyl, $C_1$-$C_6$ alkylcarbonyl, $C_6$-$C_{10}$ arylcarbonyl, cyano and nitro.

The above-mentioned "plural groups" may be the same or different.

The "$C_6$-$C_{10}$ aryl" means monocyclic aromatic hydrocarbon or condensed bicyclic aromatic hydrocarbon having 6-10 carbon atoms. In addition, condensed bicyclic hydrocarbon formed by condensation thereof with cycloalkane can also be encompassed in the "aryl" in the present invention. Specific example of the monocyclic aromatic hydrocarbon includes phenyl, and specific examples of the condensed bicyclic aromatic hydrocarbon include naphthyl and the like.

Specific examples of the condensed bicyclic hydrocarbon include indanyl, tetrahydronaphthyl and the like.

The "5- or 6-membered heterocyclic aryl" means a monocyclic aromatic 5-membered heterocycle or monocyclic aromatic 6-membered heterocycle having one or plural hetero atoms selected from a nitrogen atom, an oxygen atom and a sulfur atom in the ring. Specific examples of the "5-membered heteroaryl" include pyrrole, pyrazole, imidazole or [1,2,3]triazole having a nitrogen atom in the ring, furan having an oxygen atom in the ring, thiophene having a sulfur atom in the ring, oxazole or isoxazole having a nitrogen atom and an oxygen atom in the ring, and thiazole or isothiazole having a nitrogen atom and a sulfur atom in the ring, preferably pyrazole, isoxazole or thiophene, particularly preferably isoxazole. Specific examples of the "6-membered heteroaryl" include pyridine, pyridazine, pyrimidine, pyrazine, [1,2,3]triazine, [1,2,4,]triazine and [1,2,3,4]tetrazine, preferably pyridine or pyrazine, particularly preferably pyridine.

The "bicyclic heteroaryl" means a bicyclic aromatic heterocycle having one or plural hetero atoms selected from a nitrogen atom, an oxygen atom and a sulfur atom in the ring.

The "$C_1$-$C_6$ alkyl" means straight chain or branched alkyl having 1-6 carbon atoms. Specific examples thereof include methyl, ethyl, n-propyl, n-butyl, n-pentyl, n-hexyl, isopropyl, isobutyl, sec-butyl, tert-butyl, isopentyl and the like.

The "aryl-$C_1$-$C_6$ alkyl" means straight chain or branched alkyl having 1-6 carbon atoms, which is substituted by one or plural monocyclic aromatic hydrocarbons or condensed bicyclic aromatic hydrocarbons. Specific examples thereof include benzyl, phenethyl, phenylpropyl, naphthylmethyl and the like.

The "condensed tetrahydroquinoline" means a compound having a structure wherein saturated or unsaturated 5-membered hydrocarbon ring or 5-membered heterocyclic ring is condensed at the 7-position and the 8-position of tetrahydroquinoline.

The "halogen atom" means a fluorine atom, a chlorine atom, a bromine atom or an iodine atom.

The "$C_1$-$C_6$ alkoxy" means alkoxy comprising straight chain or branched alkyl having 1-6 carbon atoms and an oxygen atom. Specific examples thereof include methoxy, ethoxy, n-propoxy, n-butoxy, n-pentoxy, n-hexyloxy, isopropoxy, isobutoxy, sec-butoxy, tert-butoxy, isopentoxy and the like.

The "pharmaceutically acceptable" in the present specification means being generally safe and harmless, potentially biologically undesirable but preferable in other aspects, and useful for the preparation of a pharmaceutical composition containing a component not only useful as a medicament for human but also as an animal medicine.

The "pharmaceutically acceptable salt" is not particularly limited as long as it is acceptable salt as medicament and examples thereof include salts with inorganic acids such as hydrochloric acid, hydrobromic acid, hydroiodic acid, nitric acid, sulfuric acid, phosphoric acid and the like, salts with organic acids such as acetic acid, fumaric acid, maleic acid, succinic acid, citric acid, tartaric acid, adipic acid, lactic acid, methanesulfonic acid, trifluoromethanesulfonic acid, p-toluenesulfonic acid and the like, salts with alkali metals such as lithium, sodium, potassium and the like, salts with alkaline earth metals such as calcium, magnesium and the like, quaternary salts with ammonia, methyl iodide, etc. and the like.

The "pharmaceutically acceptable carrier" means a general excipient and the like widely used when preparing a composition for medicament, and the carrier is technically well known.

The "composition for medicament" means a composition containing, as an active ingredient, at least one compound of the present invention in the state of being dissolved or dispersed in a "pharmaceutically acceptable carrier", and optionally containing, where necessary, a small amount of additive, for example, lubricant, emulsifier, pH buffer and the like, which enhances the effectiveness of the active ingredient.

The "central nervous system disease" is a disease developed due to a disorder in the central nerve function.

The "depression" is one kind of a mood disorder, which is a mental disease characterized by mental symptoms of depressed mood, loss of interest and pleasure, restlessness, impaired mental activity and the like, physical symptoms such as anorexia and sleep disorder, and the like.

The "psychotic major depression" is a mental disease showing, in addition to the symptom of major depression, mental disease symptoms of delusion, hallucination and the like.

The "major depression" is a depression that shows at least one symptom of the two major items, and five or more out of the total 9 items, of the diagnostic criteria of depression in, for example, the diagnostic criteria DMS-IV formed by the American Psychiatric Association.

The "post-traumatic stress disorder" (PTSD) is a disease caused by a shocking mental trauma, which later develops various stress disorders.

The "anxiety disorder" is a generic term of symptoms associated with strong anxiety and behavioral and psychological disorders, which is represented by generalized anxiety disorder, panic disorder, phobic disorder, obsessive disorder and the like.

When the compound of the present invention contains a geometric isomer or optical isomer, such isomer is also encompassed in the scope of the present invention. In addition, the compound of the present invention may take the form of hydrate or solvate.

Moreover, when the compound of the present invention contains a proton tautomer, a tautomer thereof is also encompassed in the scope of the present invention.

The "GR selective" used in the present specification means that the Ki value for GR shows 10 times or more selectivity as compared to the Ki value for PR, MR, and preferably 30 times or more selectivity for PR, MR.

EXAMPLES

The present invention is explained in more detail in the following by referring to Reference Examples and Examples, which are not to be construed as limitative.

Unless particularly indicated, organic solution used for extraction was dried over anhydrous sodium sulfate or anhydrous magnesium sulfate. For column chromatography, normal phase chromatography using silica gel or high performance liquid chromatography (HPLC) using ODS silica gel was performed.

$^1$H-NMR was measured by 300 or 400 MHz nuclear magnetic resonance spectrometer. The chemical shift of $^1$H-NMR is expressed in relative delta (δ) value in parts per million (ppm) using tetramethylsilane (TMS) as an internal standard. The coupling constant shows obvious multiplicity in hertz (Hz) using s (singlet), d (doublet), t (triplet), m (multiplet), br (broad) and the like.

While the title compounds of the following Reference Examples and Examples are indicated as non-solvates, each salt may also take the form of a solvate (particularly hydrate) depending on the conditions and the like during preparation.

Example 1

1) 2,2,4-trimethyl-2,7,8,9-tetrahydro-1H-cyclopenta[h]quinoline

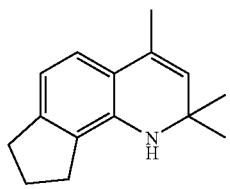 [SMILES: CC1=CC(C)(C)Nc2c1ccc1c2CCC1]

To a solution of 4-aminoindane (50 g) in acetone (500 ml) was added scandium(III) trifluoromethanesulfonate (10 g), and the mixture was stirred at room temperature for 5 days.

The reaction mixture was filtered through celite. The solvent was evaporated under reduced pressure and the residue was subjected to normal phase chromatography (elution solvent hexane-ethyl acetate=20:1) to give the title compound (59 g, 73%) as a brown oil.

NMR (400 MHz, CDCl$_3$) δ: 1.29 (6H, s), 1.98 (3H, s), 2.06-2.13 (2H, m), 2.63 (2H, t, J=7.4 Hz), 2.86 (2H, t, J=7.4 Hz), 5.24 (1H, s), 6.55 (1H, d, J=7.6 Hz), 6.92 (1H, d, J=7.6 Hz).

2) 2,2,4-trimethyl-2,3,4,7,8,9-hexahydro-1H-cyclopenta[h]quinolin-3-ol

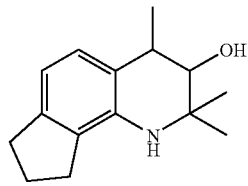 [SMILES: CC1c2ccc3c(c2NC(C)(C)C1O)CCC3]

To a solution of the compound of the previous step (59 g) in THF (600 ml) was added dropwise 1M borane/THF solution (500 ml) under ice-cooling over 2 hr, and the mixture was stirred at 10° C. for 1.5 hr, and at room temperature for 16 hr.

THF/water (1:1, 60 ml) was added dropwise to the reaction solution over 1 hr, a solution of sodium hydroxide (58 g) in water (240 ml) was added over 1 hr, and successively, 30% aqueous hydrogen peroxide (230 ml) was added dropwise over 20 min. The mixture was stirred at room temperature for 1 hr.

The reaction solution was poured into water, and the mixture was extracted with toluene. The organic layer was washed with saturated aqueous sodium hydrogen carbonate and saturated brine, and dried over sodium sulfate. The solvent was evaporated under reduced pressure, and the residue was subjected to normal phase chromatography (elution solvent hexane-ethyl acetate=20:1→5:1) to give the title compound (49 g, 77%) as a brown oil.

NMR (400 MHz, CDCl$_3$) δ: 1.10 (3H, s), 1.32 (3H, s), 1.43 (3H, d, J=6.8 Hz), 2.06-2.13 (2H, m), 2.64 (2H, t, J=7.4 Hz), 2.70-2.74 (1H, m), 2.87 (2H, t, J=7.4 Hz), 3.34 (1H, d, J=9.4 Hz), 6.64 (1H, d, J=7.7 Hz), 7.01 (1H, d, J=7.7 Hz).

3) 6-bromo-2,2,4-trimethyl-2,3,4,7,8,9-hexahydro-1H-cyclopenta[h]quinolin-3-ol

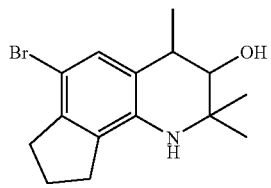 [SMILES: CC1c2cc(Br)c3c(c2NC(C)(C)C1O)CCC3]

To a solution of the compound of the previous step (49 g) in CHCl$_3$ (500 ml) was added dropwise a solution of bromine (34 g) in CHCl$_3$ (70 ml) under ice-cooling over 1 hr, and the mixture was stirred at room temperature for 3 hr. The reaction solution was adjusted to pH 12 with 10% aqueous sodium hydroxide solution (500 ml), poured into water and extracted with CHCl$_3$. The organic layer was washed with water and saturated brine, and dried over sodium sulfate. The solvent was evaporated under reduced pressure, and the residue was subjected to normal phase chromatography (elution solvent hexane-ethyl acetate=20:1→5:1) to give the title compound (49 g, 74%) as a brown oil.

NMR (400 MHz, CDCl₃) δ: 1.08 (3H, s), 1.31 (3H, s), 1.41 (3H, d, J=6.5 Hz), 1.71 (1H, d, J=6.1 Hz), 2.07-2.15 (2H, m), 2.68-2.74 (1H, m), 2.72 (2H, t, J=7.5 Hz), 2.90 (2H, t, J=7.5 Hz), 3.31 (1H, dd, J=9.4, 6.1 Hz), 3.36 (1H, s), 7.13 (1H, s).

4) 6-bromo-3-(tert-butyldimethylsilyloxy)-2,2,4-trimethyl-2,3,4,7,8,9-hexahydro-1H-cyclopenta[h]quinoline

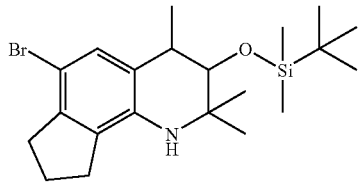 [SMILES: CC1c2cc(Br)c3c(c2NC(C)(C)C1O[Si](C)(C)C(C)(C)C)CCC3]

To a solution of the compound of the previous step (49 g) in DMF (200 ml) were added imidazole (43 g) and tert-butyldimethylchlorosilane (47 g), and the mixture was stirred at 100° C. for 16 hr.

The reaction solution was diluted with ice water, adjusted to pH 10 with saturated aqueous sodium hydrogen carbonate, and extracted with ethyl acetate. The organic layer was washed with water and saturated brine, and dried over sodium sulfate. The solvent was evaporated under reduced pressure, and the residue was subjected to normal phase chromatography (elution solvent hexane-ethyl acetate=20:1) to give the title compound (64 g, 95%) as a brown oil.

NMR (300 MHz, CDCl₃) δ:0.12 (3H, s), 0.14 (3H, s), 0.96 (9H, s), 1.06 (3H, s), 1.25 (3H, s), 1.33 (3H, d, J=5.2 Hz), 2.11 (2H, m), 2.73 (2H, brt), 2.90 (2H, t, J=5.8 Hz), 3.37 (1H, t, J=6.9 Hz), 7.12 (1H, s).

5) tert-butyl 6-bromo-3-(tert-butyldimethylsilyloxy)-2,2,4-trimethyl-2,3,4,7,8,9-hexahydro-1H-cyclopenta[h]quinoline-1-carboxylate

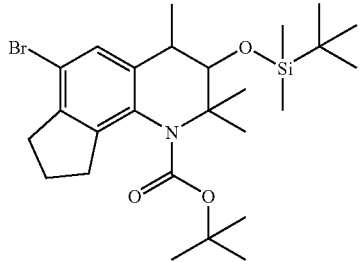 [SMILES: CC1c2cc(Br)c3c(c2N(C(=O)OC(C)(C)C)C(C)(C)C1O[Si](C)(C)C(C)(C)C)CCC3]

A solution of the compound of the previous step (46 g) in THF (260 ml) was cooled to −78° C., 1.6M n-butyllithium-hexane solution (72 ml) was added dropwise over 1 hr, and the mixture was stirred at room temperature for 2 hr. This solution was cooled to 0° C., di-tert-butyl (35 g) was added, and the mixture was stirred at room temperature for 5 hr.

The reaction solution was poured into ice water, and the mixture was extracted with ethyl acetate. The organic layer was washed with saturated brine, and dried over sodium sulfate. The solvent was evaporated under reduced pressure, and the residue was subjected to normal phase chromatography (elution solvent hexane→hexane-ethyl acetate=9:1) to give the title compound (47 g, 84%) as a colorless oil.

NMR (300 MHz, CDCl₃) δ:0.11 (3H, s), 0.13 (3H, s), 0.92 (9H, s), 1.27 (3H, d, J=5.3 Hz), 1.30 (3H, s), 1.46 (9H, s), 1.50 (3H, s), 1.93-2.20 (2H, m), 2.74 (2H, m), 2.91 (2H, m), 3.22 (1H, d, J=5.8 Hz), 7.05 (1H, s).

6) tert-butyl 6-bromo-3-hydroxy-2,2,4-trimethyl-2,3,4,7,8,9-hexahydro-1H-cyclopenta[h]quinoline-1-carboxylate

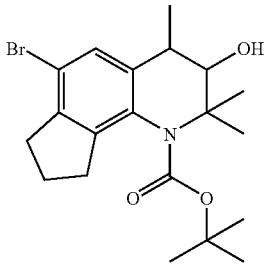 [SMILES: CC1c2cc(Br)c3c(c2N(C(=O)OC(C)(C)C)C(C)(C)C1O)CCC3]

To a solution of the compound of the previous step (47 g) in THF (180 ml) was added 1.0M tetrabutylammonium fluoride-THF solution (170 ml), and the mixture was stirred at 60° C. for 3 hr. The reaction solution was diluted with ice water, and the mixture was extracted with ethyl acetate. The organic layer was washed with saturated brine, and dried over sodium sulfate. The solvent was evaporated under reduced pressure, and the residue was subjected to normal phase chromatography (elution solvent hexane-ethyl acetate=20:1→5:1) to give the title compound (31 g, 83%) as a colorless powder.

NMR (300 MHz, CDCl₃) δ: 1.37 (3H, d, J=4.7 Hz), 1.38 (3H, s), 1.47 (9H, s), 1.50 (3H, s), 1.91 (1H, d, J=4.7 Hz), 1.93-2.20 (2H, m), 2.74 (2H, m), 2.90 (2H, m), 3.16 (1H, t, J=4.7 Hz), 7.10 (1H, s).

7) tert-butyl 6-bromo-2,2,4-trimethyl-2,3,4,7,8,9-hexahydro-1H-cyclopenta[h]quinolin-3-one-1-carboxylate

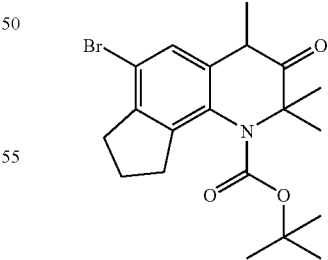

To a solution of the compound of the previous step (15 g) in CH₂Cl₂ (150 ml) were added 4 A molecular sieves (15 g) and pyridinium chlorochromate (12 g), and the mixture was stirred at room temperature for 3 hr.

The reaction mixture was filtered through celite and the solvent was evaporated under reduced pressure. The residue was subjected to normal phase chromatography (elution solvent hexane-ethyl acetate=10:1→5:1) to give the title compound (12 g, 80%) as colorless crystals.

NMR (400 MHz, CDCl$_3$) δ: 1.31 (3H, br), 1.44 (3H, d, J=6.7 Hz), 1.52 (9H, s), 1.71 (3H, br), 1.93-2.03 (1H, m), 2.16 (1H, br), 2.63-2.68 (1H, m), 2.93-2.96 (2H, m), 3.00-3.06 (1H, m), 3.88 (1H, br), 7.08 (1H, s).

8) tert-butyl 6-bromo-2,2,4,4-tetramethyl-2,3,4,7,8,9-hexahydro-1H-cyclopenta[h]quinolin-3-one-1-carboxylate

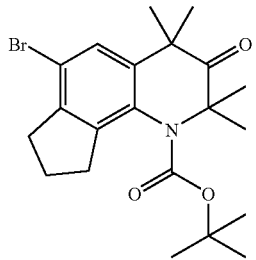

A solution of the compound of the previous step (12 g) in THF (200 ml) was cooled to −50° C., 1.6M lithiumbis(trimethylsilyl)amide/THF solution (117 ml) was added dropwise over 45 min and the mixture was heated to −20° C. A solution of iodomethane (53 g) in THF (10 ml) was added, and the mixture was stirred at room temperature for 2 hr. The reaction mixture was poured into ice water, and the mixture was extracted with ethyl acetate. The organic layer was washed with saturated brine, and dried over sodium sulfate. The solvent was evaporated under reduced pressure, and the residue was subjected to normal phase chromatography (elution solvent hexane-ethyl acetate=20:1→4:1) to give the title compound (11 g, 85%) as a colorless powder.

NMR (400 MHz, CDCl$_3$) δ: 1.41 (6H, br), 1.47 (6H, s), 1.50 (9H, s), 2.07 (2H, br), 2.84 (2H, br), 2.94 (2H, t, J=7.5 Hz), 7.18 (1H, s).

9) tert-butyl 2,2,4,4-tetramethyl-6-(4,4,5,5-tetramethyl-[1,3,2]dioxaborolan-2-yl)-2,3,4,7,8,9-hexahydro-1H-cyclopenta[h]quinolin-3-one-1-carboxylate

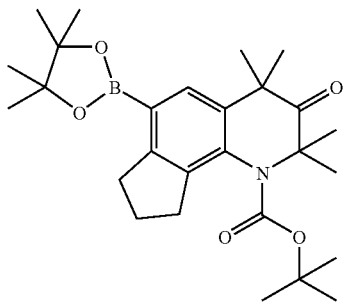 [SMILES: CC(C)(C)OC(=O)N1c2c(cc(B3OC(C)(C)C(C)(C)O3)c3c2CCC3)C(C)(C)C(=O)C1(C)C]

To a solution of the compound of the previous step (3.0 g) in isopropanol (42 ml) were added bis(pinacolato)diboron (3.6 g), potassium acetate (2.1 g) and [1,1'-bis(diphenylphosphino)ferrocene]palladium(II) dichloride (260 mg), and the mixture was stirred at 80° C. for 6 hr. The reaction solution was diluted with ethyl acetate, and the precipitate was filtered off. The solvent was evaporated under reduced pressure, and the residue was subjected to normal phase chromatography (elution solvent hexane-ethyl acetate=20:1) to give the title compound (3.3 g, 100%) as a brown powder.

NMR (400 MHz, CDCl$_3$) δ: 1.29 (12H, s), 1.49 (9H, s), 1.49 (6H, br), 1.55 (6H, s), 2.01 (2H, br), 2.73 (2H, br), 3.12 (2H, br), 7.45 (1H, s).

10) 6-(2-chloro-4-hydroxyphenyl)-2,2,4,4-tetramethyl-2,3,4,7,8,9-hexahydro-1H-cyclopenta[h]quinolin-3-one

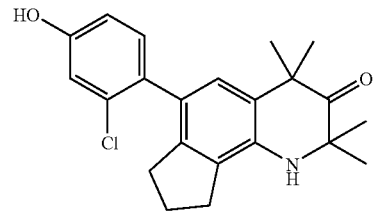 [SMILES: CC1(C)Nc2c(cc(-c3ccc(O)cc3Cl)c3c2CCC3)C(C)(C)C1=O]

To a solution of the compound of the previous step (40 mg) in isopropanol (1 ml) were added 4-bromo-3-chlorophenol (18 mg), 2.0M aqueous potassium carbonate solution (85 μl) and tetrakis(triphenylphosphine)palladium(0) (3.0 mg), and the mixture was stirred at 80° for 16 hr. The reaction solution was diluted with water and ethyl acetate, and the mixture was filtered through a sellite column, and the solvent was evaporated to give a residue. To the residue was added trifluoroacetic acid (1 ml), and the mixture was stood at room temperature for 30 min. Trifluoroacetic acid was evaporated, and the residue was subjected to high performance liquid chromatography to give the title compound (13 mg, 40%).

NMR (300 MHz, DMSO) δ: 1.27 (6H, s), 1.33 (6H, s), 1.97-2.04 (2H, m), 2.64 (2H, t, J=7.4 Hz), 2.80 (2H, t, J=7.4 Hz), 5.17 (1H, s).

6.75 (1H, dd, J=8.3, 2.4 Hz), 6.79 (1H, s), 6.88 (1H, d, J=2.4 Hz). 7.11 (1H, d, J=8.3 Hz), 9.82 (1H, s). MS: 370 (M$^+$+1).

Example 2

6-(3,5-dimethylisoxazol-4-yl)-2,2,4,4-tetramethyl-2,3,4,7,8,9-hexahydro-1H-cyclopenta[h]quinolin-3-one

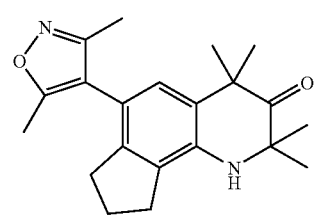 [SMILES: Cc1noc(C)c1-c1cc2c(c3c1CCC3)NC(C)(C)C(=O)C2(C)C]

Using 4-iodo-3,5-dimethylisoxazole instead of 4-bromo-3-chlorophenol of Example 1, 10) and according to a similar method, the title compound (17 mg, 43%) was obtained.

NMR (300 MHz, CDCl$_3$) δ: 1.36 (6H, s), 1.44 (6H, s), 2.11-2.18 (2H, m), 2.16 (3H, s), 2.27 (3H, s), 2.68 (2H, t, J=7.5 Hz), 2.80 (2H, t, J=7.5 Hz), 6.79 (1H, s). MS: 339 (M$^+$+1).

Example 3

6-(3,5-dimethyl-3H-imidazol-4-yl)-2,2,4,4-tetramethyl-2,3,4,7,8,9-hexahydro-1H-cyclopenta[h]quinolin-3-one

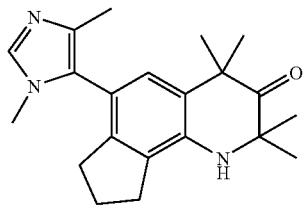 [SMILES: Cc1ncn(C)c1-c1cc2c(c3c1CCC3)NC(C)(C)C(=O)C2(C)C]

Using 4-bromo-3,5-dimethyl-3H-imidazole instead of 4-bromo-3-chlorophenol of Example 1, 10) and according to a similar method, the title compound (21 mg, 94%) was obtained.

NMR (400 MHz, CDCl$_3$) δ: 1.36 (3H, s), 1.38 (3H, s), 1.44 (6H, s), 2.11 (3H, s), 2.11-2.18 (2H, m), 2.57-2.77 (2H, m), 2.80 (2H, t, J=7.5 Hz), 3.39 (3H, s), 3.59 (1H, br), 6.68 (1H, s), 7.50 (1H, s). MS: 338 (M$^+$+1)

Example 4

6-(3,5-dimethyl-3H-[1,2,3]triazol-4-yl)-2,2,4,4-tetramethyl-2,3,4,7,8,9-hexahydro-1H-cyclopenta[h]quinolin-3-one

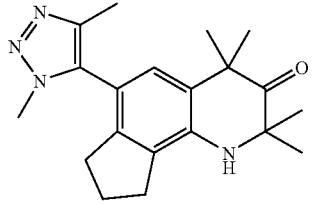 [SMILES: Cc1nnn(C)c1-c1cc2c(c3c1CCC3)NC(C)(C)C(=O)C2(C)C]

Using 4-bromo-3,5-dimethyl-3H-[1,2,3]triazole instead of 4-bromo-3-chlorophenol of Example 1, 10) and according to a similar method, the title compound (9.4 mg, 17%) was obtained.

NMR (300 MHz, DMSO) δ: 1.28 (6H, s), 1.35 (6H, s), 2.01-2.09 (2H, m), 2.09 (3H, s), 2.49-2.58 (2H, m), 2.83 (2H, t, J=7.3 Hz), 3.75 (3H, s), 5.47 (1H, s), 6.93 (1H, s). MS: 339 (M$^+$+1).

Example 5

6-(2-cyano-3-methylthiophen-4-yl)-2,2,4,4-tetramethyl-2,3,4,7,8,9-hexahydro-1H-cyclopenta[h]quinolin-3-one

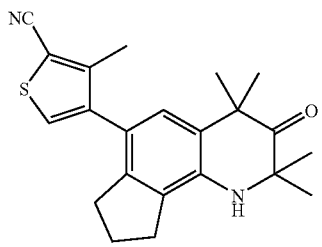

Using 4-bromo-3-methylthiophene-2-carbonitrile instead of 4-bromo-3-chlorophenol of Example 1, 10) and according to a similar method, the title compound (11 mg, 37%) was obtained.

NMR (300 MHz, DMSO) δ: 1.27 (6H, s), 1.34 (6H, s), 1.96-2.06 (2H, m), 2.49 (3H, s), 2.71 (2H, t, J=7.5 Hz), 2.82 (2H, t, J=7.5 Hz), 5.31 (1H, s), 6.88 (1H, s), 7.84 (1H, s). MS: 365 (M$^+$+1).

Example 6

2,2,4,4-tetramethyl-6-(3-methylpyridin-4-yl)-2,3,4,7,8,9-hexahydro-1H-cyclopenta[h]quinolin-3-one

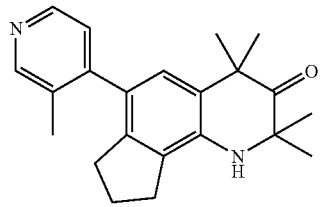 [SMILES: Cc1cnccc1-c1cc2c(c3c1CCC3)NC(C)(C)C(=O)C2(C)C]

Using 4-chloro-3-methylpyridine hydrochloride instead of 4-bromo-3-chlorophenol of Example 1, 10) and according to a similar method, the title compound (17 mg, 29%) was obtained.

NMR (400 MHz, DMSO) δ: 1.28 (6H, s), 1.34 (6H, s), 1.99-2.03 (2H, m), 2.12 (3H, s), 2.61 (2H, t, J=7.4 Hz), 2.83 (2H, t, J=7.4 Hz), 5.30 (1H, s), 6.83 (1H, s), 7.17 (1H, d, J=4.8 Hz), 8.36 (1H, d, J=4.8 Hz), 8.46 (1H, s). MS: 335 (M$^+$+1).

Example 7

6-(2-chloropyridin-3-yl)-2,2,4,4-tetramethyl-2,3,4,7,8,9-hexahydro-1H-cyclopenta[h]quinolin-3-one

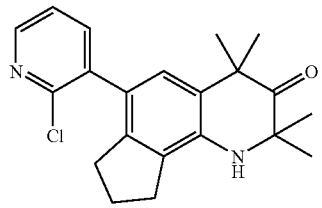 [SMILES: CC1(C)Nc2c(cc(-c3cccnc3Cl)c3c2CCC3)C(C)(C)C1=O]

Using 3-bromo-2-chloropyridine instead of 4-bromo-3-chlorophenol of Example 1, 10) and according to a similar method, the title compound (14 mg, 23%) was obtained.

NMR (400 MHz, DMSO) δ: 1.28 (6H, s), 1.34 (6H, s), 2.00-2.04 (2H, m), 2.66 (2H, t, J=7.4 Hz), 2.83 (2H, t, J=7.4 Hz), 5.32 (1H, s), 6.92 (1H, s), 7.45 (1H, dd, J=7.6, 4.7 Hz), 7.81 (1H, dd, J=7.6, 1.6 Hz), 8.37 (1H, dd, J=4.7, 1.6 Hz). MS: 355 (M$^+$+1)

Example 8

6-(5-fluoro-2-methoxypyridin-3-yl)-2,2,4,4-tetramethyl-2,3,4,7,8,9-hexahydro-1H-cyclopenta[h]quinolin-3-one

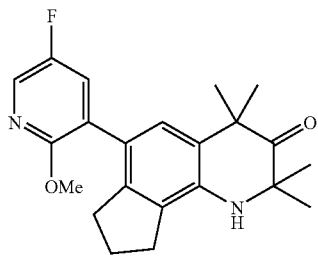 [SMILES: COc1ncc(F)cc1-c1cc2c(c3c1CCC3)NC(C)(C)C(=O)C2(C)C]

Using 3-bromo-5-fluoro-2-methoxypyridine instead of 4-bromo-3-chlorophenol of Example 1, 10) and according to a similar method, the title compound (18 mg, 30%) was obtained.

NMR (400 MHz, DMSO) δ:1.27 (6H, s), 1.35 (6H, s), 1.96-2.03 (2H, m), 2.69 (2H, t, J=7.4 Hz), 2.80 (2H, t, J=7.3 Hz), 5.27 (1H, s), 6.94 (1H, s), 7.58 (1H, dd, J=8.6, 3.0 Hz), 8.09 (1H, d, J=3.0 Hz). MS: 369 (M⁺+1).

Example 9

6-(2,5-dimethylpyridin-4-yl)-2,2,4,4-tetramethyl-2,3,4,7,8,9-hexahydro-1H-cyclopenta[h]quinolin-3-one

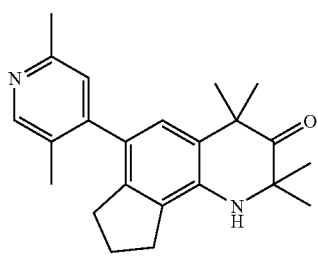 [SMILES: Cc1cc(-c2cc3c(c4c2CCC4)NC(C)(C)C(=O)C3(C)C)c(C)cn1]

Using 4-bromo-2,5-dimethylpyridine instead of 4-bromo-3-chlorophenol of Example 1, 10) and according to a similar method, the title compound (12 mg, 21%) was obtained.

NMR (300 MHz, DMSO) δ:1.29 (6H, s), 1.35 (6H, s), 2.02-2.07 (2H, m), 2.27 (3H, s), 2.66 (3H, s), 2.71 (2H, t, J=7.2 Hz), 2.85 (2H, t, J=7.2 Hz), 6.00 (1H, s), 6.96 (1H, s), 7.78 (1H, s), 8.73 (1H, s). MS: 349 (M⁺+1)

Example 10

6-(1H-indol-7-yl)-2,2,4,4-tetramethyl-2,3,4,7,8,9-hexahydro-1H-cyclopenta[h]quinolin-3-one

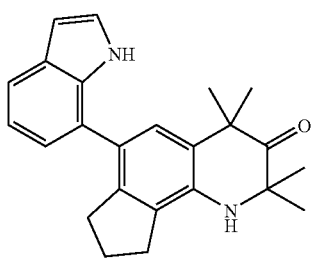 [SMILES: CC1(C)Nc2c(cc(-c3cccc4cc[nH]c34)c3c2CCC3)C(C)(C)C1=O]

Using 7-bromoindole instead of 4-bromo-3-chlorophenol of Example 1, 10) and according to a similar method, the title compound (25 mg, 54%) was obtained.

NMR (300 MHz, CDCl₃) δ: 1.31 (6H, s), 1.38 (6H, s), 2.01 (2H, m), 2.70 (2H, t, J=7.5 Hz), 2.85 (2H, t, J=7.5 Hz), 5.20 (1H, br), 6.46 (1H, dd, J=3.0, 1.2 Hz), 6.93 (1H, dd, J=6.9, 0.9 Hz), 7.02 (1H, s), 6.99-7.04 (1H, m), 7.24 (1H, t, J=3.0 Hz), 7.47 (1H, d, J=7.5 Hz), 10.59 (1H, br). MS: 359 (M⁺+1).

Example 11

6-(5-fluoro-1H-indol-7-yl)-2,2,4,4-tetramethyl-2,3,4,7,8,9-hexahydro-1H-cyclopenta[h]quinolin-3-one

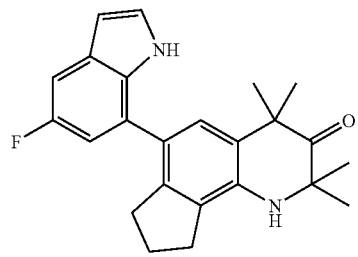 [SMILES: CC1(C)Nc2c(cc(-c3cc(F)cc4cc[nH]c34)c3c2CCC3)C(C)(C)C1=O]

Using 7-bromo-5-fluoroindole instead of 4-bromo-3-chlorophenol of Example 1, 10) and according to a similar method, the title compound (23 mg, 51%) was obtained.

NMR (300 MHz, DMSO) δ: 1.30 (6H, s), 1.38 (6H, s), 1.99-2.04 (2H, m), 2.72 (2H, t, J=7.5 Hz), 2.85 (2H, t, J=7.5 Hz), 5.31 (1H, s), 6.46 (1H, s), 6.80 (1H, dd, J=9.8, 2.3 Hz), 7.04 (1H, s), 7.23 (1H, dd, J=9.8, 2.3 Hz), 7.31 (1H, s), 10.74 (1H, s). MS: 377 (M⁺+1).

Example 12

6-(1H-benzoimidazol-7-yl)-2,2,4,4-tetramethyl-2,3,4,7,8,9-hexahydro-1H-cyclopenta[h]quinolin-3-one

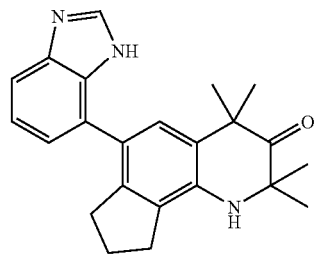 [SMILES: CC1(C)Nc2c(cc(-c3cccc4nc[nH]c34)c3c2CCC3)C(C)(C)C1=O]

Using 7-iodo-1H-benzoimidazole instead of 4-bromo-3-chlorophenol of Example 1, 10) and according to a similar method, the title compound (6.3 mg, 11%) was obtained.

NMR (300 MHz, DMSO) δ: 1.31 (6H, s), 1.38 (6H, s), 2.02-2.09 (2H, m), 2.72 (2H, t, J=7.2 Hz), 2.87 (2H, t, J=7.2 Hz), 5.45 (1H, s), 7.06 (1H, s), 7.45 (1H, d, J=7.5 Hz), 7.58 (1H, dd, J=7.5, 7.5 Hz), 7.77 (1H, d, J=7.5 Hz), 9.46 (1H, s). MS: 360 (M⁺+1).

Example 13

2,2,4,4-tetramethyl-6-(1H-pyrrolo[3,2-b]pyridin-7-yl)-2,3,4,7,8,9-hexahydro-1H-cyclopenta[h]quinolin-3-one

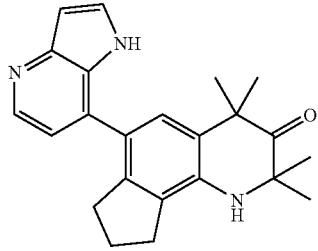 [SMILES: CC1(C)Nc2c(cc(-c3ccnc4cc[nH]c34)c3c2CCC3)C(C)(C)C1=O]

Using 7-chloro-1H-pyrrolo[3,2-b]pyridine instead of 4-bromo-3-chlorophenol of Example 1, 10) and according to a similar method, the title compound (1.6 mg, 3%) was obtained.

NMR (300 MHz, DMSO) δ: 1.33 (6H, s), 1.40 (6H, s), 2.04-2.09 (2H, m), 2.81-2.91 (4H, m), 5.76 (1H, s), 6.87 (1H, dd, J=3.0, 1.5 Hz), 7.23 (1H, s), 7.55 (1H, d, J=6.0 Hz), 8.11 (1H, dd, J=3.0, 3.0 Hz), 8.61 (1H, d, J=6.0 Hz), 12.37 (1H, s). MS: 360 (M$^+$+1)

Example 14

6-(imidazo[1,2-a]pyridin-5-yl)-2,2,4,4-tetramethyl-2,3,4,7,8,9-hexahydro-1H-cyclopenta[h]quinolin-3-one

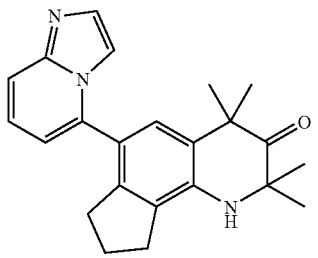 [SMILES: CC1(C)Nc2c(cc(-c3cccc4nccn34)c3c2CCC3)C(C)(C)C1=O]

Using 5-bromoimidazo[1,2-a]pyridine instead of 4-bromo-3-chlorophenol of Example 1, 10) and according to a similar method, the title compound (41 mg, 77%) was obtained.

NMR (400 MHz, DMSO) δ: 1.31 (6H, s), 1.36 (6H, s), 1.99-2.05 (2H, m), 2.63 (2H, t, J=7.1 Hz), 2.86 (2H, t, J=7.1 Hz), 5.52 (1H, s), 6.81 (1H, d, J=6.6 Hz), 7.16 (1H, s), 7.29 (1H, dd, J=8.8, 6.6 Hz), 7.43 (1H, s), 7.54 (1H, d, J=8.8 Hz). MS: 360 (M$^+$+1).

Example 15

6-(1H-indazol-4-yl)-2,2,4,4-tetramethyl-2,3,4,7,8,9-hexahydro-1H-cyclopenta[h]quinolin-3-one

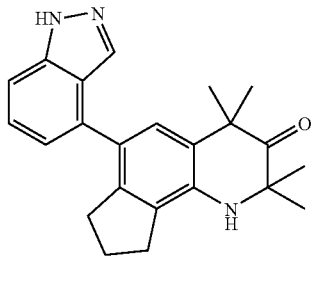 [SMILES: CC1(C)Nc2c(cc(-c3cccc4[nH]ncc34)c3c2CCC3)C(C)(C)C1=O]

Using 4-bromo-1H-indazole instead of 4-bromo-3-chlorophenol of Example 1, 10) and according to a similar method, the title compound (14 mg, 24%) was obtained.

NMR (300 MHz, DMSO) δ: 1.30 (6H, s), 1.38 (6H, s), 2.00-2.08 (2H, m), 2.85 (4H, t, J=7.2 Hz), 5.31 (1H, s), 7.05 (1H, d, J=6.4 Hz), 7.14 (1H, s), 7.36 (1H, dd, J=8.3, 6.4 Hz), 7.45 (1H, d, J=8.3 Hz), 7.89 (1H, s), 13.11 (1H, s). MS: 360 (M$^+$+1) .

Example 16

2,2,4,4-tetramethyl-6-(pyrazolo[1,5-a]pyridin-4-yl)-2,3,4,7,8,9-hexahydro-1H-cyclopenta[h]quinolin-3-one

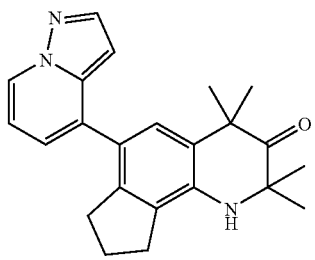 [SMILES: CC1(C)Nc2c(cc(-c3cccn4nccc34)c3c2CCC3)C(C)(C)C1=O]

Using 4-pyrazolo[1,5-a]pyridyl trifluoromethanesulfonate instead of 4-bromo-3-chlorophenol of Example 1, 10) and according to a similar method, the title compound (14 mg, 24%) was obtained.

NMR (300 MHz, DMSO) δ: 1.30 (6H, s), 1.37 (6H, s), 1.99-2.08 (2H, m), 2.79-2.87 (4H, m), 5.38 (1H, s), 6.42 (1H, d, J=2.3 Hz), 6.93 (1H, to dd, J=6.8, 6.8 Hz), 7.12 (1H, d, J=6.8 Hz), 7.17 (1H, s), 7.98 (1H, d, J=2.3 Hz), 8.61 (1H, d, J=6.8 Hz). MS: 360 (M$^+$+1).

Example 17

2,2,4,4-tetramethyl-6-([1,2,4]triazolo[4,3-a]pyridin-5-yl)-2,3,4,7,8,9-hexahydro-1H-cyclopenta[h]quinolin-3-one

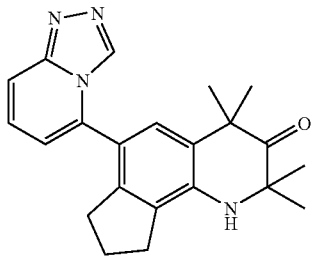 [SMILES: CC1(C)Nc2c(cc(-c3cccc4nncn34)c3c2CCC3)C(C)(C)C1=O]

Using 5-chloro[1,2,4]triazolo[4,3-a]pyridine instead of 4-bromo-3-chlorophenol of Example 1, 10) and according to a similar method, the title compound (19 mg, 33%) was obtained.

NMR (400 MHz, DMSO) δ: 1.31 (6H, s), 1.38 (6H, s), 2.01-2.08 (2H, m), 2.70 (2H, t, J=7.3 Hz), 2.87 (2H, t, J=7.3 Hz), 5.61 (1H, s), 6.89 (1H, d, J=6.6 Hz), 7.25 (1H, s), 7.44 (1H, dd, J=9.2, 2.4 Hz), 7.74 (1H, d, J=9.2 Hz), 8.92 (1H, s). MS: 361 (M$^+$+1).

Example 18

6-(imidazo[1,2-a]pyrazin-5-yl)-2,2,4,4-tetramethyl-2,3,4,7,8,9-hexahydro-1H-cyclopenta[h]quinolin-3-one

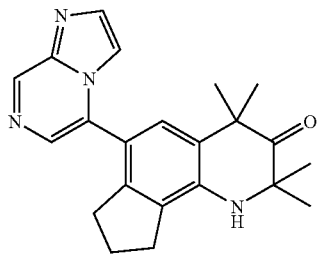 [SMILES: CC1(C)Nc2c(cc(-c3cncc4nccn34)c3c2CCC3)C(C)(C)C1=O]

Using 5-chloroimidazo[1,2-a]pyrazine instead of 4-bromo-3-chlorophenol of Example 1, 10) and according to a similar method, the title compound (22 mg, 37%) was obtained.

NMR (300 MHz, DMSO) δ:1.32 (6H, s), 1.37 (6H, s), 2.00-2.10 (2H, m), 2.71 (2H, t, J=7.5 Hz), 2.87 (2H, t, J=7.5 Hz), 5.68 (1H, s), 7.27 (1H, s), 7.87 (1H, s), 7.97 (1H, d, J=1.1 Hz), 7.99 (1H, s), 9.14 (1H, s). MS: 361 (M$^+$+1)

Example 19

2,2,4,4-tetramethyl-6-(thieno[2,3-b]pyridin-3-yl)-2,3,4,7,8,9-hexahydro-1H-cyclopenta[h]quinolin-3-one

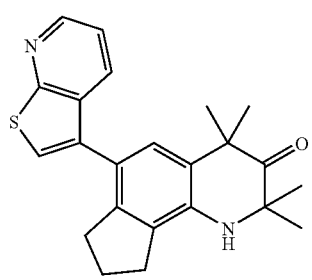 [SMILES: CC1(C)Nc2c(cc(-c3csc4ncccc34)c3c2CCC3)C(C)(C)C1=O]

Using 3-bromothieno[2,3-b]pyridine instead of 4-bromo-3-chlorophenol of Example 1, 10) and according to a similar method, the title compound (17 mg, 27%) was obtained.

NMR (400 MHz, DMSO) δ: 1.30 (6H, s), 1.38 (6H, s), 2.01-2.07 (2H, m), 2.80 (2H, t, J=7.4 Hz), 2.86 (2H, t, J=7.4 Hz), 5.32 (1H, s), 7.05 (1H, s), 7.45 (1H, dd, J=7.9, 4.7 Hz), 7.75 (1H, s), 8.01 (1H, dd, J=7.9, 1.3 Hz), 8.59 (1H, dd, J=4.7, 1.3 Hz). MS: 377 (M$^+$+1).

Example 20

2,2,4,4-tetramethyl-6-(quinolin-5-yl)-2,3,4,7,8,9-hexahydro-1H-cyclopenta[h]quinolin-3-one

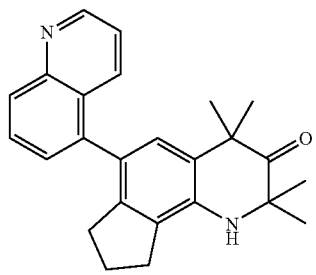 [SMILES: CC1(C)Nc2c(cc(-c3cccc4ncccc34)c3c2CCC3)C(C)(C)C1=O]

Using 5-bromoquinoline instead of 4-bromo-3-chlorophenol of Example 1, 10) and according to a similar method, the title compound (33 mg, 74%) was obtained.

NMR (300 MHz, DMSO) δ: 1.32 (6H, s), 1.36 (3H, s), 1.38 (3H, s), 1.95-2.05 (2H, m), 2.41-2.50 (1H, m), 2.54-2.64 (1H, m), 2.85-2.91 (2H, m), 5.37 (1H, br), 6.95 (1H, s), 7.65-7.70 (2H, m), 7.92 (1H, dd, J=8.4, 7.2 Hz), 8.08 (1H, d, J=8.4 Hz), 8.23 (1H, d, J=8.4 Hz), 9.05 (1H, dd, J=4.5, 3.0 Hz). MS: 371 (M$^+$+1)

Example 21

2,2,4,4-tetramethyl-6-([1,8]naphthyridin-4-yl)-2,3,4,7,8,9-hexahydro-1H-cyclopenta[h]quinolin-3-one

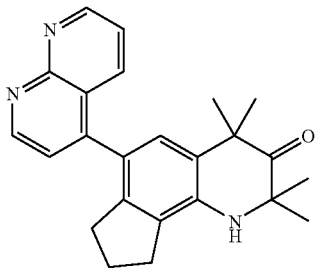 [SMILES: CC1(C)Nc2c(cc(-c3ccnc4ncccc34)c3c2CCC3)C(C)(C)C1=O]

Using 4-chloro[1,8]naphthyridine instead of 4-bromo-3-chlorophenol of Example 1, 10) and according to a similar method, the title compound (19 mg, 32%) was obtained.

NMR (400 MHz, DMSO) δ: 1.32 (6H, s), 1.37 (6H, s), 2.00-2.05 (2H, m), 2.67-2.73 (2H, m), 2.89 (2H, t, J=6.8 Hz), 5.63 (1H, s), 7.06 (1H, s), 7.74 (1H, d, J=4.9 Hz), 7.77 (1H, dd, J=8.7, 4.5 Hz), 8.32 (1H, dd, J=8.7, 1.9 Hz), 9.16 (1H, d, J=4.9 Hz), 9.18 (1H, dd, J=4.5, 1.9 Hz). MS: 372 (M$^+$+1)

Example 22

2,2,4,4-tetramethyl-6-(phthalazin-5-yl)-2,3,4,7,8,9-hexahydro-1H-cyclopenta[h]quinolin-3-one

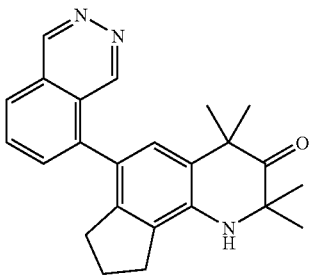 [SMILES: CC1(C)Nc2c(cc(-c3cccc4cnncc34)c3c2CCC3)C(C)(C)C1=O]

Using 5-bromophthalazine instead of 4-bromo-3-chlorophenol of Example 1, 10) and according to a similar method, the title compound (17 mg, 28%) was obtained.

NMR (300 MHz, DMSO) δ: 1.33 (6H, s), 1.36 (3H, s), 1.39 (3H, s), 2.00-2.07 (2H, m), 2.70-2.77 (2H, m), 2.86-2.93 (2H, m), 5.48 (1H, s), 7.04 (1H, s), 8.02 (1H, dd, J=7.6, 1.5 Hz), 8.14 (1H, dd, J=7.9, 7, 6 Hz), 8.22 (1H, d, J=7.9 Hz), 9.33 (1H, s), 9.83 (1H, d, J=1.5 Hz). MS: 372 (M$^+$+1)

Example 23

6-(3,5-dimethylisoxazol-4-yl)-2,2,4,4-tetramethyl-3-methylene-2,3,4,7,8,9-hexahydro-1H-cyclopenta[h]quinoline

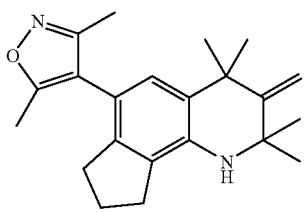 [SMILES: C=C1C(C)(C)Nc2c(cc(-c3c(C)noc3C)c3c2CCC3)C1(C)C]

To a solution of methyltriphenylphosphonium bromide (570 mg) in toluene (1.1 ml) was added tert-butoxy potassium (160 mg), and the mixture was stirred at 100° C. for 1 hr. Toluene was distilled off, and the obtained emulsion was added to 6-(3,5-dimethylisoxazol-4-yl)-2,2,4,4-tetramethyl-2,3,4,7,8,9-hexahydro-1H-cyclopenta[h]quinolin-3-one (98 mg) of Example 2, and the mixture was stirred at 150° C. for 3 hr. The reaction solution was diluted with water and ethyl acetate, and filtered through a sellite column. The solvent was evaporated, and the residue was subjected to high performance liquid chromatography to give the title compound (32 mg, 33%).

NMR (400 MHz, DMSO) δ: 1.34 (6H, s), 1.39 (6H, s), 1.97-2.03 (2H, m), 2.05 (3H, s), 2.22 (3H, s), 2.57 (2H, t, J=7.4 Hz), 2.75 (2H, t, J=7.4 Hz), 4.70 (1H, s), 4.96 (1H, s), 5.04 (1H, s), 6.81 (1H, s). MS: 337 (M$^+$+1).

Example 24

6-(imidazo[1,2-a]pyridin-5-yl)-2,2,4,4-tetramethyl-3-methylene-2,3,4,7,8,9-hexahydro-1H-cyclopenta[h]quinoline

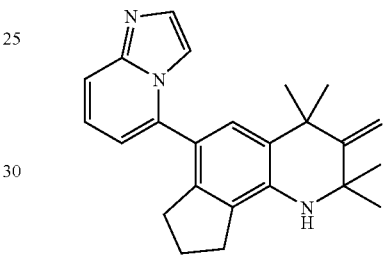

Using 6-(5-imidazo[1,2-a]pyridyl)-2,2,4,4-tetramethyl-2,3,4,7,8,9-hexahydro-1H-cyclopenta[h]quinolin-3-one instead of 6-(3,5-dimethylisoxazol-4-yl)-2,2,4,4-tetramethyl-2,3,4,7,8,9-hexahydro-1H-cyclopenta[h]quinolin-3-one of Example 23 and according to a similar method, the title compound (22 mg, 38%) was obtained.

NMR (400 MHz, DMSO) δ: 1.40 (6H, s), 1.42 (6H, s), 1.99-2.07 (2H, m), 2.67 (2H, br), 2.82 (2H, t, J=7.0 Hz), 5.01 (1H, s), 5.09 (1H, s), 5.24 (1H, s), 7.25 (1H, s), 7.42 (1H, d, J=7.0 Hz), 7.85 (1H, d, J=2.0 Hz), 7.91 (1H, d, J=8.8 Hz), 7.97 (1H, dd, J=8.8, 7.0 Hz), 8.17 (1H, d, J=2.0 Hz). MS: 358 (M$^+$+1)

Example 25

2,2,4,4-tetramethyl-3-methylene-6-([1,8]naphthyridin-4-yl)-2,3,4,7,8,9-hexahydro-1H-cyclopenta[h]quinoline

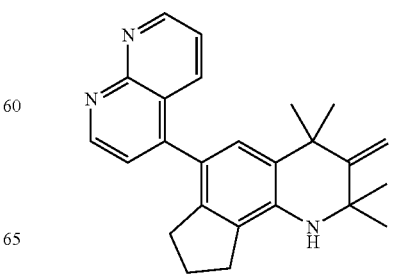

Using 2,2,4,4-tetramethyl-6-([1,8]naphthyridin-4-yl)-2,3,4,7,8,9-hexahydro-1H-cyclopenta[h]quinolin-3-one instead of 6-(3,5-dimethylisoxazol-4-yl)-2,2,4,4-tetramethyl-2,3,4,7,8,9-hexahydro-1H-cyclopenta[h]quinolin-3-one of Example 23 and according to a similar method, the title compound (5.2 mg, 9%) was obtained.

NMR (400 MHz, DMSO) δ: 1.39 (6H, s), 1.41 (6H, s), 1.96-2.01 (2H, m), 2.66 (2H, br), 2.81 (2H, br), 4.95 (1H, s), 4.99 (1H, s), 5.07 (1H, s), 7.00 (1H, s), 7.52 (1H, d, J=4.6 Hz), 7.60 (1H, dd, J=8.4, 4.0 Hz), 8.13 (1H, dd, J=8.4, 1.6 Hz), 9.05 (1H, d, J=4.6 Hz), 9.08 (1H, dd, J=4.0, 1.6 Hz). MS: 370 (M$^+$+1).

Example 26

2,2,4,4-tetramethyl-3-methylene-6-([1,2,4]triazolo[4,3-a]pyridin-5-yl)-2,3,4,7,8,9-hexahydro-1H-cyclopenta[h]quinoline

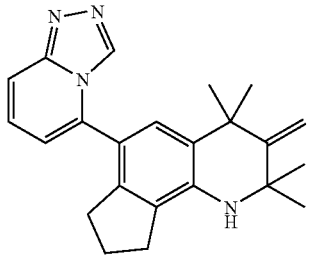 [SMILES: C=C1C(C)(C)Nc2c(cc(-c3cccc4nncn34)c3c2CCC3)C1(C)C]

Using 2,2,4,4-tetramethyl-6-([1,2,4]triazolo[4,3-a]pyridin-5-yl)-2,3,4,7,8,9-hexahydro-1H-cyclopenta[h]quinolin-3-one instead of 6-(3,5-dimethylisoxazol-4-yl)-2,2,4,4-tetramethyl-2,3,4,7,8,9-hexahydro-1H-cyclopenta[h]quinolin-3-one of Example 23 and according to a similar method, the title compound (21 mg, 35%) was obtained.

NMR (400 MHz, DMSO) δ: 1.39 (6H, s), 1.42 (6H, s), 1.99-2.08 (2H, m), 2.69 (2H, t, J=7.2 Hz), 2.80 (2H, t, J=7.2 Hz), 5.00 (1H, s), 5.08 (1H, s), 7.03 (1H, d, J=7.0 Hz), 7.27 (1H, s), 7.62 (1H, dd, J=9.2, 7.0 Hz), 7.81 (1H, d, J=9.2 Hz), 9.01 (1H, s). MS: 359 (M$^+$+1).

Example 27

6-(imidazo[1,2-a]pyrazin-5-yl)-2,2,4,4-tetramethyl-3-methylene-2,3,4,7,8,9-hexahydro-1H-cyclopenta[h]quinoline

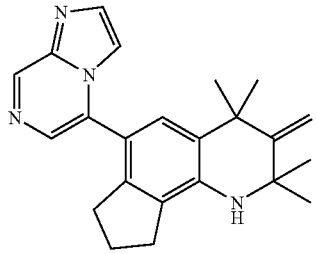 [SMILES: C=C1C(C)(C)Nc2c(cc(-c3cncc4nccn34)c3c2CCC3)C1(C)C]

Using 6-(imidazo[1,2-a]pyrazin-5-yl)-2,2,4,4-tetramethyl-2,3,4,7,8,9-hexahydro-1H-cyclopenta[h]quinolin-3-one instead of 6-(3,5-dimethylisoxazol-4-yl)-2,2,4,4-tetramethyl-2,3,4,7,8,9-hexahydro-1H-cyclopenta[h]quinolin-3-one of Example 23 and according to a similar method, the title compound (5.7 mg, 10%) was obtained.

NMR (400 MHz, DMSO) δ: 1.39 (6H, s), 1.42 (6H, s), 2.00-2.03 (2H, m), 2.66 (2H, t, J=7.3 Hz), 2.81 (2H, t, J=7.3 Hz), 5.00 (1H, s), 5.07 (1H, s), 5.11 (1H, s), 7.23 (1H, s), 7.72 (1H, s), 7.82 (2H, s), 9.01 (1H, s). MS: 359 (M$^+$+1)

Example 28

6-(3,5-dimethyl-3H-[1,2,3]triazol-4-yl)-2,2,4,4-tetramethyl-3-methylene-2,3,4,7,8,9-hexahydro-1H-cyclopenta[h]quinoline

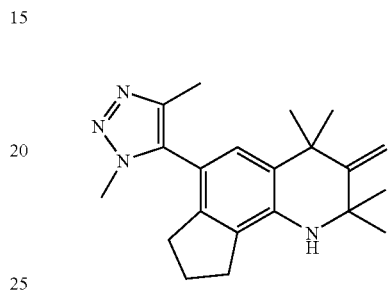

Using 6-(3,5-dimethyl-3H-[1,2,3]triazol-4-yl)-2,2,4,4-tetramethyl-2,3,4,7,8,9-hexahydro-1H-cyclopenta[h]quinolin-3-one instead of 6-(3,5-dimethylisoxazol-4-yl)-2,2,4,4-tetramethyl-2,3,4,7,8,9-hexahydro-1H-cyclopenta[h]quinolin-3-one of Example 23 and according to a similar method, the title compound (13 mg, 24%) was obtained.

NMR (400 MHz, DMSO) δ: 1.35 (6H, s), 1.40 (6H, s), 1.99-2.03 (2H, m), 2.08 (3H, s), 2.52 (2H, t, J=7.3 Hz), 2.77 (2H, t, J=7.3 Hz), 3.74 (3H, s), 4.98 (1H, s), 5.06 (1H, s), 6.91 (1H, s). MS: 337 (M$^+$+1).

Example 29

6-(3,5-dimethyl-3H-imidazol-4-yl)-2,2,4,4-tetramethyl-3-methylene-2,3,4,7,8,9-hexahydro-1H-cyclopenta[h]quinoline

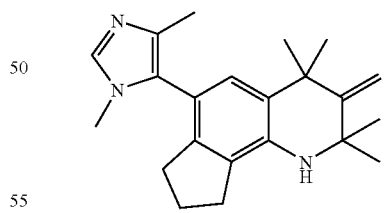

Using 6-(3,5-dimethyl-3H-imidazol-4-yl)-2,2,4,4-tetramethyl-2,3,4,7,8,9-hexahydro-1H-cyclopenta[h]quinolin-3-one instead of 6-(3,5-dimethylisoxazol-4-yl)-2,2,4,4-tetramethyl-2,3,4,7,8,9-hexahydro-1H-cyclopenta[h]quinolin-3-one of Example 23 and according to a similar method, the title compound (22 mg, 41%) was obtained.

NMR (400 MHz, DMSO) δ: 1.36 (6H, s), 1.39 (3H, s), 1.40 (3H, s), 2.00-2.04 (2H, m), 2.12 (3H, s), 2.55-2.61 (2H, m), 2.78 (2H, t, J=7.2 Hz), 3.54 (3H, s), 4.99 (1H, s), 5.06 (1H, s), 6.98 (1H, s), 9.03 (1H, s). MS: 336 (M$^+$+1).

Example 30

6-(2-cyano-3-methylthiophen-4-yl)-2,2,4,4-tetramethyl-3-methylene-2,3,4,7,8,9-hexahydro-1H-cyclopenta[h]quinoline Using 6-(2-cyano-3-methylthiophen-4-yl)-2,2,4,4-tetramethyl-2,3,4,7,8,9-hexahydro-1H-cyclopenta[h]quinolin-3-one obtained in Example 5 instead of 6-(3,5-dimethylisoxazol-4-yl)-2,2,4,4-tetramethyl-2,3,4,7,8,9-hexahydro-1H-cyclopenta[h]quinolin-3-one of Example 23 and according to a similar method, the title compound (18 mg, 30%) was obtained.
NMR (400 MHz, DMSO) δ: 1.34 (6H, s), 1.39 (6H, s), 1.96-2.00 (2H, m), 2.25 (3H, s), 2.68 (2H, t, J=7.4 Hz), 2.75 (2H, t, J=7.4 Hz), 4.96 (1H, s), 5.04 (1H, s), 6.87 (1H, s), 7.80 (1H, s). MS: 363 (M$^+$+1).

Example 31

2,2,4,4-tetramethyl-3-methylene-6-(pyrazolo[1,5-a]pyridin-4-yl)-2,3,4,7,8,9-hexahydro-1H-cyclopenta[h]quinoline Using 2,2,4,4-tetramethyl-6-(pyrazolo[1,5-a]pyridin-4-yl)-2,3,4,7,8,9-hexahydro-1H-cyclopenta[h]quinolin-3-one obtained in Example 16 instead of 6-(3,5-dimethylisoxazol-4-yl)-2,2,4,4-tetramethyl-2,3,4,7,8,9-hexahydro-1H-cyclopenta[h]quinolin-3-one of Example 23 and according to a similar method, the title compound (9.0 mg, 15%) was obtained.
NMR (400 MHz, DMSO) δ: 1.37 (6H, s), 1.41 (6H, s), 1.95-2.03 (2H, m), 2.78 (4H, t, J=7.3 Hz), 4.83 (1H, br), 4.98 (1H, s), 5.06 (1H, s), 6.39 (1H, d, J=2.0 Hz), 6.92 (1H, dd, J=6.9, 6.8 Hz), 7.10 (1H, d, J=6.9 Hz), 7.18 (1H, s), 7.98 (1H, d, J=2.0 Hz), 8.59 (1H, d, J=6.8 Hz). MS: 358 (M$^+$+1)

Example 32

2,2,4,4-tetramethyl-3-methylene-6-(quinolin-5-yl)-2,3,4,7,8,9-hexahydro-1H-cyclopenta[h]quinoline Using 2,2,4,4-tetramethyl-6-(quinolin-5-yl)-2,3,4,7,8,9-hexahydro-1H-cyclopenta[h]quinolin-3-one obtained in Example instead of 6-(3,5-dimethylisoxazol-4-yl)-2,2,4,4-tetramethyl-2,3,4,7,8,9-hexahydro-1H-cyclopenta[h]quinolin-3-one of Example 23 and according to a similar method, the title compound (13 mg, 21%) was obtained.
NMR (400 MHz, DMSO) δ: 1.39 (3H, s), 1.40 (6H, s), 1.43 (3H, s), 1.94-2.01 (2H, m), 2.39-2.46 (1H, m), 2.54-2.62 (1H, m), 2.80-2.85 (2H, m), 5.00 (1H, s), 5.07 (1H, s), 6.97 (1H, s), 7.70 (1H, d, J=7.0 Hz), 7.80 (1H, dd, J=8.5, 4.6 Hz), 8.00 (1H, dd, J=8.4, 7.0 Hz), 8.12 (1H, d, J=8.5 Hz), 8.40 (1H, d, J=8.4 Hz), 9.15 (1H, dd, J=4.6, 1.0 Hz). MS: 369 (M$^+$+1)

Example 33

1) 6-bromo-2,2,4,4-tetramethyl-2,3,4,7,8,9-hexahydro-1H-cyclopenta[h]quinolin-3-one To a solution of tert-butyl 6-bromo-2,2,4,4-tetramethyl-2,3,4,7,8,9-hexahydro-1H-cyclopenta[h]quinolin-3-one-1-carboxylate (1.0 g) obtained in Example 1, 8) in CH$_2$Cl$_2$ (10 ml) was added trifluoroacetic acid (10 ml), and the mixture was stirred at room temperature for 1 hr. The reaction solution was neutralized with 1N aqueous sodium hydroxide solution, and the mixture was extracted with CHCl$_3$. The organic layer was washed with water and saturated brine, and dried over sodium sulfate. The solvent was evaporated under reduced pressure. The residue was subjected to normal phase chromatography (elution solvent hexane→hexane-ethyl acetate=7:3) to give the title compound (760 mg, 100%).
NMR (400 MHz, CHCl$_3$) δ: 1.32 (6H, s), 1.42 (6H, s), 2.12-2.20 (2H, m), 2.83 (2H, t, J=7.5 Hz), 2.95 (2H, t, J=7.5 Hz), 3.46 (1H, s), 7.14 (1H, s). MS: 322 (M$^+$+1)

2) 6-(2-methoxyphenyl)-2,2,4,4-tetramethyl-2,3,4,7,8,9-hexahydro-1H-cyclopenta[h]quinolin-3-one To a solution of the compound of the previous step (20 mg) in isopropanol (1.5 ml) were added 2-methoxyphenylboronic acid (9.4 mg), 2.0M aqueous potassium carbonate solution (93 μl) and tetrakis(triphenylphosphine)palladium(0) (2.2 mg), and the mixture was heated under reflux for 4 hr. The reaction solution was diluted with water and ethyl acetate, and filtered through a sellite column. The solvent was evaporated and the residue was subjected to high performance liquid chromatography to give the title compound (16 mg, 72%).
NMR (400 MHz, DMSO) δ: 1.27 (6H, s), 1.34 (6H, s), 1.95-2.00 (2H, m), 2.63 (2H, t, J=7.4 Hz), 2.80 (2H, t, J=7.3 Hz), 6.83 (1H, s), 6.95 (1H, ddd, J=7.4, 7.4, 0.6 Hz), 7.03 (1H, d, J=8.0 Hz), 7.13 (1H, dd, J=7.4, 1.7 Hz), 7.28 (1H, ddd, J=8.0, 7.4, 1.7 Hz). MS: 350 (M$^+$+1).

Example 34

6-(4-hydroxy-2-methylphenyl)-2,2,4,4-tetramethyl-2,3,4,7,8,9-hexahydro-1H-cyclopenta[h]quinolin-3-one Using 4-bromo-3-methylphenol instead of 4-bromo-3-chlorophenol of Example 1, 10) and according to a similar method, the title compound (12 mg, 39%) was obtained.
NMR (300 MHz, DMSO) δ: 1.26 (6H, s), 1.32 (6H, s), 1.93-2.02 (2H, m), 1.99 (3H, s), 2.49-2.57 (2H, m), 2.80 (2H, t, J=7.5 Hz), 5.08 (1H, br), 6.57 (1H, dd, J=8.4, 2.4 Hz), 6.64 (1H, d, J=2.4 Hz), 6.90 (1H, d, J=8.4 Hz), 9.19 (1H, br). MS: 350 (M$^+$+1).

Example 35

6-(5-fluoro-2-methoxyphenyl)-2,2,4,4-tetramethyl-2,3,4,7,8,9-hexahydro-1H-cyclopenta[h]quinolin-3-one Using 2-bromo-4-fluoroanisole instead of 4-bromo-3-chlorophenol of Example 1, 10) and according to a similar method, the title compound (22 mg, 35%) was obtained.
NMR (400 MHz, DMSO) δ: 1.27 (6H, s), 1.34 (6H, s), 1.96-1.99 (2H, m), 2.65 (2H, t, J=7.5 Hz), 2.79 (2H, t, J=7.4 Hz), 3.71 (3H, s), 5.17 (1H, s), 6.86 (1H, s), 6.98 (1H, dd, J=9.3, 3.1 Hz), 7.03 (1H, dd, J=8.9, 4.8 Hz), 7.08 (1H, dd, J=8.4, 3.1 Hz). MS: 368 (M$^+$+1).

Example 36

6-(3-hydroxymethyl-5-methylisoxazol-4-yl)-2,2,4,4-tetramethyl-2,3,4,7,8,9-hexahydro-1H-cyclopenta[h]quinolin-3-one Using 4-bromo-3-(tert-butyldimethylsilyloxymethyl)-5-methylisoxazole instead of 4-bromo-3-chlorophenol of Example 1, 10) and according to a similar method, tert-butyl 6-[(3-tert-butyldimethylsilyloxymethyl)-5-methylisoxazol-4-yl]-2,2,4,4-tetramethyl-2,3,4,7,8,9-hexahydro-1H-cyclopenta[h]quinolin-3-one-1-carboxylate was obtained.

Then, to a solution of the obtained compound (49 mg) in THF (0.2 ml) was added 1M tetrabutylammonium fluoride-THF solution (500 μl), and the mixture was stirred at room temperature for 3 hr. The solvent was evaporated under reduced pressure, and the residue was subjected to normal phase chromatography to give tert-butyl 6-(3-hydroxymethyl-5-methylisoxazol-4-yl)-2,2,4,4-tetramethyl-2,3,4,7,8,9-hexahydro-1H-cyclopenta[h]quinolin-3-one-1-carboxylate.

Trifluoroacetic acid (1.0 ml) was added to the obtained compound, and the mixture was stood at room temperature for 30 min. Trifluoroacetic acid was evaporated, and the residue was subjected to high performance liquid chromatography to give the title compound (9.0 mg, 83%).

NMR (400 MHz, DMSO) δ: 1.27 (6H, s), 1.33 (6H, s), 2.01 (2H, m), 2.24 (3H, s), 2.62 (2H, t, J=7.4 Hz), 2.81 (2H, t, J=7.4 Hz), 4.31 (2H, d, J=5.5 Hz), 5.23 (1H, t, J=5.5 Hz), 5.25 (1H, s), 6.94 (1H, s). MS: 355 ($M^+$+1).

Example 37

6-(3-amino-5-methylisoxazol-4-yl)-2,2,4,4-tetramethyl-2,3,4,7,8,9-hexahydro-1H-cyclopenta[h]quinolin-3-one Using di-tert-butyl (4-bromo-5-methylisoxazol-3-yl)dicarbamate instead of 4-bromo-3-chlorophenol of Example 1, 10) and according to a similar method, the title compound (4.5 mg, 16%) was obtained.

NMR (400 MHz, DMSO) δ: 1.26 (6H, s), 1.34 (6H, s), 1.98-2.06 (2H, m), 2.10 (3H, s), 2.67 (2H, br), 2.80 (2H, t, J=7.4 Hz), 5.12 (2H, s), 5.22 (1H, s), 6.80 (1H, s). MS: 340 ($M^+$+1).

Example 38

A: 6-(3-dimethylamino-5-methylisoxazol-4-yl)-2,2,4,4-tetramethyl-2,3,4,7,8,9-hexahydro-1H-cyclopenta[h]quinolin-3-one
B: 2,2,4,4-tetramethyl-6-(3-methylamino-5-methylisoxazol-4-yl)-2,3,4,7,8,9-hexahydro-1H-cyclopenta[h]quinolin-3-one To a solution of the compound of the previous step (16 mg) in DMF (500 μl) were added potassium carbonate (10 mg) and iodomethane (23 μl), and the mixture was stirred at 100° C. for 2 hr. The reaction solution was diluted with water, and the mixture was extracted with ethyl acetate. The organic layer was washed with saturated brine, and dried over sodium sulfate. The solvent was evaporated under reduced pressure. The residue was subjected to normal phase chromatography (elution solvent hexane→hexane-ethyl acetate=3:2) to give the title compound A (1.9 mg, 11%) and the title compound B (1.7 mg, 10%).

A: NMR (400 MHz, DMSO) δ: 1.25 (6H, s), 1.32 (6H, s), 2.00-2.06 (2H, m), 2.10 (3H, s), 2.55 (6H, s), 2.68 (2H, br), 2.82 (2H, br), 5.25 (1H, s), 6.82 (1H, s). MS: 368 ($M^+$+1)
B: NMR (400 MHz, DMSO) δ: 1.26 (6H, s), 1.33 (6H, s), 1.98-2.05 (2H, m), 2.10 (3H, s), 2.65 (3H, d, J=5.0 Hz), 2.71 (2H, br), 2.80 (2H, t, J=7.4 Hz), 5.20 (1H, d, J=5.0 Hz), 5.23 (1H, s), 6.78 (1H, s). MS: 354 ($M^+$+1)

Example 39

6-(3-ethylamino-5-methylisoxazol-4-yl)-2,2,4,4-tetramethyl-2,3,4,7,8,9-hexahydro-1H-cyclopenta[h]quinolin-3-one Using iodoethane instead of iodomethane of Example 38 and according to a similar method, the title compound (3.0 mg, 18%) was obtained.

NMR (400 MHz, DMSO) δ: 1.09 (3H, t, J=7.1 Hz), 1.26 (6H, s), 1.34 (6H, s), 2.02 (2H, br), 2.09 (3H, s), 2.55 (2H, br), 2.80 (2H, t, J=7.4 Hz), 3.04-3.11 (2H, m), 5.16 (1H, t, J=5.8 Hz), 5.23 (1H, s), 6.80 (1H, s). MS: 368 ($M^+$+1).

Example 40

A: 6-(3-cyano-5-methylisoxazol-4-yl)-2,2,4,4-tetramethyl-2,3,4,7,8,9-hexahydro-1H-cyclopenta[h]quinolin-3-one
B: 6-(3-hydroxyiminomethyl-5-methylisoxazol-4-yl)-2,2,4,4-tetramethyl-2,3,4,7,8,9-hexahydro-1H-cyclopenta[h]quinolin-3-one To a solution of tert-butyl 2,2,4,4-tetramethyl-6-(4,4,5,5-tetramethyl-[1,3,2]dioxaborolan-2-yl)-2,3,4,7,8,9-hexahydro-1H-cyclopenta[h]quinolin-3-one-1-carboxylate (1.2 g) obtained in Example 1, 9) in isopropanol (11 ml) were added 4-bromo-3-[1,3]dioxolan-2-yl-5-methylisoxazole (500 mg), 2.0 M aqueous potassium carbonate solution (3.2 ml) and tetrakis(triphenylphosphine)palladium(0) (250 mg), and the mixture was stirred at 80° C. for 16 hr. The reaction solution was diluted with water and ethyl acetate, the mixture was filtered through celite, and the filtrate was extracted with ethyl acetate. The organic layer was washed with saturated brine, and dried over magnesium sulfate. The solvent was evaporated under reduced pressure. The residue was subjected to normal phase chromatography (elution solvent hexane-ethyl acetate=6:1) to give tert-butyl 6-(3-[1,3]dioxolan-2-yl-5-methylisoxazol-4-yl)-2,2,4,4-tetramethyl-2,3,4,7,8,9-hexahydro-1H-cyclopenta[h]quinolin-3-one-1-carboxylate (410 mg, 32%).

Then, to a solution of the obtained compound (400 mg) in THF (1.6 ml) were added water (1.6 ml) and trifluoroacetic acid (10 ml), and the mixture was stirred at 60° C. for 3 hr. The reaction mixture was neutralized with 1N aqueous sodium hydroxide solution, and the mixture was extracted with ethyl acetate. The organic layer was washed with water and saturated brine, and dried over magnesium sulfate. The solvent was evaporated under reduced pressure. The residue was subjected to normal phase chromatography (elution solvent hexane-ethyl acetate=6:1) to give 6-(3-formyl-5-methylisoxazol-4-yl)-2,2,4,4-tetramethyl-2,3,4,7,8,9-hexahydro-1H-cyclopenta[h]quinolin-3-one (200 mg, 70%).

To a solution of the obtained compound (100 mg) in acetic acid (2.6 ml) were added hydroxylamine-O-sulfonic acid (44 mg) and sodium acetate (78 mg), and the mixture was heated under reflux for 4 hr. The reaction solution was diluted with water and ethyl acetate, and the mixture was neutralized with 1N aqueous sodium hydroxide solution and extracted with ethyl acetate. The organic layer was washed with water and saturated brine, and dried over magnesium sulfate. The solvent was evaporated under reduced pressure. The residue was subjected to normal phase chromatography (elution solvent hexane-ethyl acetate=4:1) to give the title compound A (32 mg, 36%) and the title compound B (28 mg, 29%).

A: NMR (300 MHz, CDCl$_3$) δ: 1.37 (6H, s), 1.45 (6H, s), 2.14-2.21 (2H, m), 2.45 (3H, s), 2.78-2.83 (4H, m), 3.64 (1H, s), 6.88 (1H, s). MS: 350 ($M^+$+1)

B: NMR (300 MHz, CDCl$_3$) δ: 1.36 (6H, s), 1.42 (6H, s), 2.06-2.14 (2H, m), 2.30 (3H, s), 2.63 (2H, br), 2.77 (2H, t, J=7.3 Hz), 3.55 (1H, s), 6.80 (1H, s), 7.93 (1H, s), 8.01 (1H, s). MS: 368 (M$^+$+1).

Example 41

6-(2-cyano-4-methylthiophen-5-yl)-2,2,4,4-tetramethyl-2,3,4,7,8,9-hexahydro-1H-cyclopenta[h]quinolin-3-one Using 5-bromo-4-methylthiophene-2-carbonitrile instead of 4-bromo-3-chlorophenol of Example 1, 10) and according to a similar method, the title compound (12 mg, 38%) was obtained.
NMR (300 MHz, DMSO) δ: 1.27 (6H, s), 1.34 (6H, s), 2.02-2.09 (2H, m), 2.13 (3H, s), 2.76-2.85 (4H, m), 5.50 (1H, br), 6.98 (1H, s), 7.82 (1H, s). MS: 365 (M$^+$+1).

Example 42

6-(3,5-dimethyl-1H-pyrazol-4-yl)-2,2,4,4-tetramethyl-2,3,4,7,8,9-hexahydro-1H-cyclopenta[h]quinolin-3-one Using tert-butyl 4-bromo-3,5-dimethylpyrazole-1-carboxylate instead of 4-bromo-3-chlorophenol of Example 1, 10) and according to a similar method, the title compound (10 mg, 35%) was obtained.
NMR (400 MHz, DMSO) δ: 1.26 (6H, s), 1.33 (6H, s), 1.96-2.00 (2H, m), 2.00 (6H, s), 2.58 (2H, t, J=7.4 Hz), 2.80 (2H, t, J=7.3 Hz), 5.09 (1H, s), 6.72 (1H, s), 12.09 (1H, br). MS: 338 (M$^+$+1).

Example 43

6-(2-methoxypyridin-3-yl)-2,2,4,4-tetramethyl-2,3,4,7,8,9-hexahydro-1H-cyclopenta[h]quinolin-3-one Using 3-iodo-2-methoxypyridine instead of 4-bromo-3-chlorophenol of Example 1, 10) and according to a similar method, the title compound (9.9 mg, 33%) was obtained.
NMR (400 MHz, DMSO) δ: 1.27 (6H, s), 1.34 (6H, s), 1.94-2.07 (2H, m), 2.66 (2H, t, J=7.5 Hz), 2.81 (2H, t, J=7.5 Hz), 3.84 (3H, s), 5.20 (1H, br), 6.89 (1H, s), 7.02 (1H, dd, J=7.2, 5.1 Hz), 7.56 (1H, dd, J=7.2, 1.8 Hz), 8.12 (1H, dd, J=5.1, 1.8 Hz). MS: 351 (M$^+$+1).

Example 44

6-(5-chloro-2-fluoropyridin-4-yl)-2,2,4,4-tetramethyl-2,3,4,7,8,9-hexahydro-1H-cyclopenta[h]quinolin-3-one Using 5-chloro-2-fluoro-4-iodopyridine instead of 4-bromo-3-chlorophenol of Example 1, 10) and according to a similar method, the title compound (19 mg, 31%) was obtained.
NMR (400 MHz, DMSO) δ: 1.28 (6H, s), 1.35 (6H, s), 2.01-2.07 (2H, m), 2.74 (2H, t, J=7.5 Hz), 2.83 (2H, t, J=7.4 Hz), 5.47 (1H, s), 7.00 (1H, s), 7.29 (1H, d, J=1.8 Hz), 8.38 (1H, s). MS: 373 (M$^+$+1).

Example 45

6-(benzooxazol-7-yl)-2,2,4,4-tetramethyl-2,3,4,7,8,9-hexahydro-1H-cyclopenta[h]quinolin-3-one Using 7-bromobenzooxazole instead of 4-bromo-3-chlorophenol of Example 1, 10) and according to a similar method, the title compound (5.4 mg, 11%) was obtained.
NMR (300 MHz, DMSO) δ: 1.30 (6H, s), 1.38 (6H, s), 2.01-2.05 (2H, m), 2.80-2.88 (4H, m), 5.39 (1H, s), 7.17 (1H, s), 7.40-7.46 (2H, m), 7.72 (1H, dd, J=6.8, 1.9 Hz), 8.74 (1H, s). MS: 361 (M$^+$+1).

Example 46

6-(2,3-dioxo-1H-indolin-7-yl)-2,2,4,4-tetramethyl-2,3,4,7,8,9-hexahydro-1H-cyclopenta[h]quinolin-3-one Using 7-bromo-2,3-dioxoindoline instead of 4-bromo-3-chlorophenol of Example 1, 10) and according to a similar method, the title compound (39 mg, 37%) was obtained.
NMR (300 MHz, DMSO) δ: 1.28 (6H, s), 1.37 (6H, s), 2.01-2.08 (2H, m), 2.74 (2H, t, J=7.5 Hz), 2.83 (2H, t, J=7.5 Hz), 5.30 (1H, br), 6.89 (1H, s), 7.10 (1H, dd, J=7.9, 7.5 Hz), 7.45-7.49 (2H, m), 10.71 (1H, s). MS: 389 (M$^+$+1).

Example 47

2,2,4,4-tetramethyl-6-(thieno[2,3-b]pyridin-4-yl)-2,3,4,7,8,9-hexahydro-1H-cyclopenta[h]quinolin-3-one Using 4-chlorothieno[2,3-b]pyridine instead of 4-bromo-3-chlorophenol of Example 1, 10) and according to a similar method, the title compound (4.0 mg, 6%) was obtained.
NMR (300 MHz, DMSO) δ: 1.30 (6H, s), 1.35 (6H, s), 2.01-2.09 (2H, m), 2.79 (2H, t, J=7.4 Hz), 2.86 (2H, t, J=7.4 Hz), 5.47 (1H, s), 7.10 (1H, s), 7.25 (1H, d, J=6.1 Hz), 7.36 (1H, d, J=4.8 Hz), 7.84 (1H, d, J=6.1 Hz), 8.54 (1H, d, J=4.8 Hz). MS: 377 (M$^+$+1).

Example 48

2,2,4,4-tetramethyl-6-(quinolin-4-yl)-2,3,4,7,8,9-hexahydro-1H-cyclopenta[h]quinolin-3-one Using 4-chloroquinoline instead of 4-bromo-3-chlorophenol of Example 1, 10) and according to a similar method, the title compound (12 mg, 20%) was obtained.
NMR (300 MHz, DMSO) δ: 1.33 (6H, s), 1.37 (6H, s), 2.00-2.05 (2H, m), 2.59 (1H, br), 2.73 (1H, br), 2.88 (2H, br), 5.63 (1H, br), 7.07 (1H, s), 7.72-7.77 (2H, m), 7.87 (1H, d, J=8.3 Hz), 7.96 (1H, dd, J=8.3, 6.8 Hz), 8.19 (1H, d, J=8.3 Hz), 9.09 (1H, d, J=5.3 Hz). MS: 371 (M$^+$+1).

Example 49

6-(5-hydroxynaphthalen-1-yl)-2,2,4,4-tetramethyl-2,3,4,7,8,9-hexahydro-1H-cyclopenta[h]quinolin-3-one Using 5-hydroxynaphthyl trifluoromethanesulfonate instead of 4-bromo-3-chlorophenol of Example 1, 10) and according to a similar method, the title compound (11 mg, 23%) was obtained.

NMR (400 MHz, DMSO) δ: 1.30 (3H, s), 1.31 (3H, s), 1.35 (6H, s), 1.93-2.01 (2H, m), 2.43-2.56 (2H, m), 2.81-2.91 (2H, m), 5.24 (1H, br), 6.85 (1H, d, J=7.4 Hz), 6.89 (1H, s), 6.99 (1H, d, J=8.5 Hz), 7.21 (1H, dd, J=8.5, 7.4 Hz), 7.32 (1H, d, J=7.1 Hz), 7.44 (1H, dd, J=8.2, 7.1 Hz), 8.12 (1H, d, J=8.2 Hz), 10.10 (1H, s). MS: 386 (M$^+$+1).

Example 50

1) tert-butyl 4-allyl-6-bromo-2,2,4-trimethyl-2,3,4,7,8,9-hexahydro-1H-cyclopenta[h]quinolin-3-one-1-carboxylate Using allyl iodide instead of iodomethane of Example 1, 8) and according to a similar method, the title compound (695 mg, 91%) was obtained.

NMR (300 MHz, CDCl$_3$) δ: 1.40 (6H, s), 1.48 (9H, s), 1.99 (3H, br), 1.99-2.03 (1H, m), 2.03-2.17 (1H, m), 2.45-2.50 (1H, m), 2.69-2.76 (2H, m), 2.93-2.98 (3H, m), 5.01 (1H, d, J=16.8 Hz), 5.06 (1H, d, J=9.6 Hz), 5.52-5.57 (1H, m), 7.12 (1H, s).

2) tert-butyl 4-allyl-2,2,4-trimethyl-6-(4,4,5,5-tetramethyl-[1,3,2]dioxaborolan-2-yl)-2,3,4,7,8,9-hexahydro-1H-cyclopenta[h]quinolin-3-one-1-carboxylate Using the compound of the previous step (425 mg) instead of tert-butyl 6-bromo-2,2,4,4-tetramethyl-2,3,4,7,8,9-hexahydro-1H-cyclopenta[h]quinolin-3-one-1-carboxylate of Example 1, 9) and according to a similar method, the title compound (356 mg, 76%) was obtained.

NMR (300 MHz, CDCl$_3$) δ: 1.33 (12H, s), 1.47 (9H, s), 1.58 (6H, s), 1.75 (3H, br), 1.90-1.98 (1H, m), 2.05-2.20 (1H, m), 2.51-2.95 (4H, m), 3.03-3.23 (2H, m), 5.01 (1H, d, J=17.9 Hz), 5.03 (1H, d, J=10.5 Hz), 5.56-5.65 (1H, m), 7.41 (1H, s).

3) 4-allyl-6-(4-hydroxy-2-methylphenyl)-2,2,4-trimethyl-2,3,4,7,8,9-hexahydro-1H-cyclopenta[h]quinolin-3-one Using the compound of the previous step (50 mg) instead of tert-butyl 2,2,4,4-tetramethyl-6-(4,4,5,5-tetramethyl-[1,3,2]dioxaborolan-2-yl)-2,3,4,7,8,9-hexahydro-1H-cyclopenta[h]quinolin-3-one-1-carboxylate of Example 1, 10), 4-bromo-3-methylphenol instead of 4-bromo-3-chlorophenol of Example 1, 10), and according to a similar method, the title compound (11 mg, 28%) was obtained.

NMR (300 MHz, DMSO) δ: 1.21 (3H, s), 1.28 (6H, s), 1.93-2.03 (2H, m), 1.99 (3H, s), 2.40-2.67 (4H, m), 2.81 (2H, t, J=7.6 Hz), 4.92 (1H, d, J=12.2 Hz), 4.92 (1H, d, J=14.2 Hz), 4.95 (1H, br), 5.32-5.43 (1H, m), 6.57 (1H, dd, J=8.2, 2.5 Hz), 6.64 (1H, d, J=2.5 Hz), 6.66 (1H, s), 6.90 (1H, d, J=8.2 Hz), 9.20 (1H, br). MS: 376 (M$^+$+1).

Example 51

4-allyl-6-(3,5-dimethylisoxazol-4-yl)-2,2,4-trimethyl-2,3,4,7,8,9-hexahydro-1H-cyclopenta[h]quinolin-3-one Using 3,5-dimethyl-4-(4,4,5,5-tetramethyl-1,3,2-dioxaborolan-2-yl)isoxazole instead of tert-butyl 2,2,4,4-tetramethyl-6-(4,4,5,5-tetramethyl-[1,3,2]dioxaborolan-2-yl)-2,3,4,7,8,9-hexahydro-1H-cyclopenta[h]quinolin-3-one-1-carboxylate of Example 1, 10), using tert-butyl 4-allyl-6-bromo-2,2,4-trimethyl-2,3,4,7,8,9-hexahydro-1H-cyclopenta[h]quinolin-3-one-1-carboxylate obtained in Example 50, 1) instead of 4-bromo-3-chlorophenol of Example 1, 10) and according to a similar method, the title compound (25 mg, 31%) was obtained.

NMR (300 MHz, CDCl$_3$) δ: 1.31 (3H, s), 1.38 (3H, s), 1.41 (3H, s), 2.14 (3H, s), 2.14 (2H, dt, J=15.0, 7.5 Hz), 2.27 (3H, s), 2.43 (1H, dd, J=13.0, 7.5 Hz), 2.67 (2H, dd, J=15.0, 7.5 Hz), 2.78 (3H, dd, J=14.0, 7.2 Hz), 4.93-4.94 (1H, m), 4.98 (1H, s), 5.37-5.52 (1H, m), 6.74 (1H, s). MS: 365 (M$^+$+1).

Example 52

4-allyl-6-(2-cyano-4-methylthiophen-5-yl)-2,2,4-trimethyl-2,3,4,7,8,9-hexahydro-1H-cyclopenta[h]quinolin-3-one Using 5-bromo-4-methylthiophene-2-carbonitrile instead of 4-bromo-3-methylphenol of Example 50, 3) and according to a similar method, the title compound (7.6 mg, 24%) was obtained.

NMR (300 MHz, DMSO) δ: 1.23 (3H, s), 1.28 (3H, s), 1.32 (3H, s), 2.02-2.13 (2H, m), 2.13 (3H, s), 2.44-2.54 (1H, m), 2.63 (1H, dd, J=13.8, 6.6 Hz), 2.74-2.85 (4H, m), 4.94 (1H, d, J=12.0 Hz), 4.94 (1H, d, J=15.6 Hz), 5.31-5.47 (1H, m), 5.47 (1H, s), 6.95 (1H, s), 7.82 (1H, s). MS: 391 (M$^+$+1).

Example 53

4-allyl-6-(3-chloropyridin-4-yl)-2,2,4-trimethyl-2,3,4,7,8,9-hexahydro-1H-cyclopenta[h]quinolin-3-one Using 3-chloro-4-pyridylboronic acid pentahydrate instead of 3,5-dimethyl-4-(4,4,5,5-tetramethyl-1,3,2-dioxaborolan-2-yl)isoxazole of Example 51 and according to a similar method, the title compound (6.9 mg, 16%) was obtained.

NMR (300 MHz, DMSO) δ: 1.23 (3H, s), 1.30 (3H, s), 1.31 (3H, s), 2.00-2.08 (2H, m), 2.43-2.54 (1H, m), 2.63 (1H, dd, J=13.8, 7.0 Hz), 2.68-2.74 (2H, m), 2.83 (2H, t, J=7.5 Hz), 4.94 (1H, d, J=11.8 Hz), 4.94 (1H, d, J=15.5 Hz), 5.34-5.48 (1H, m), 6.93 (1H, s), 7.42 (1H, d, J=4.9 Hz), 8.51 (1H, d, J=4.9 Hz), 8.68 (1H, s). MS: 381 (M$^+$+1).

Example 54

4-allyl-6-(2-methoxypyridin-3-yl)-2,2,4-trimethyl-2,3,4,7,8,9-hexahydro-1H-cyclopenta[h]quinolin-3-one Using 3-iodo-2-methoxypyridine instead of 4-bromo-3-methylphenol of Example 50, 3) and according to a similar method, the title compound (7.6 mg, 20%) was obtained.

NMR (300 MHz, DMSO) δ: 1.23 (3H, s), 1.28 (3H, s), 1.30 (3H, s), 1.99-2.07 (2H, m), 2.42-2.80 (6H, m), 3.84 (3H, s), 4.92 (1H, d, J=10.2 Hz), 4.94 (1H, d, J=17.1 Hz), 5.20 (1H, br), 5.32-5.48 (1H, m), 6.88 (1H, s), 7.02 (1H, dd, J=7.2, 5.1 Hz), 7.55 (1H, dd, J=7.2, 1.8 Hz), 8.12 (1H, dd, J=5.1, 1.8 Hz). MS: 377 (M$^+$+1)

Example 55

4-allyl-6-(1H-indol-7-yl)-2,2,4-trimethyl-2,3,4,7,8,9-hexahydro-1H-cyclopenta[h]quinolin-3-one Using 7-(4,4,5,5-tetramethyl-1,3,2-dioxaborolan-2-yl)indole instead of 3,5-dimethyl-4-(4,4,5,5-tetramethyl-1,3,2-dioxaborolan-2-yl)isoxazole of Example 51 and according to a similar method, the title compound (17 mg, 34%) was obtained.

NMR (300 MHz, DMSO) δ: 1.25 (3H, s), 1.32 (3H, s), 1.34 (3H, s), 1.99-2.07 (2H, m), 2.50-2.76 (4H, m), 2.86 (2H, t, J=7.5 Hz), 4.95 (1H, d, J=11.4 Hz), 4.97 (1H, d, J=15.6 Hz), 5.22 (1H, s), 5.43-5.52 (1H, m), 6.47 (1H, dd, J=2.7, 1.8 Hz), 6.93 (1H, d, J=6.9 Hz), 6.98 (1H, s), 7.02 (1H, dd, J=7.5, 6.9 Hz), 7.24 (1H, dd, J=3.0, 2.7 Hz), 7.48 (1H, d, J=7.5 Hz), 10.57 (1H, br). MS: 385 ($M^+$+1).

Example 56

4-allyl-2,2,4-trimethyl-6-(quinolin-5-yl)-2,3,4,7,8,9-hexahydro-1H-cyclopenta[h]quinolin-3-one Using 5-(4,4,5,5-tetramethyl-1,3,2-dioxaborolan-2-yl) quinoline instead of 3,5-dimethyl-4-(4,4,5,5-tetramethyl-1,3,2-dioxaborolan-2-yl)isoxazole of Example 51 and according to a similar method, the title compound (26 mg, 58%) was obtained.

NMR (300 MHz, DMSO) δ: 1.27 (3H, s), 1.31 (3H, s), 1.34 (3H, s), 1.98-2.05 (2H, m), 2.40-2.75 (4H, m), 2.88 (2H, br), 4.91-5.03 (2H, m), 5.40-5.51 (1H, m), 6.91 (1H, d, J=12.4 Hz), 7.62-7.73 (2H, m), 7.90-7.97 (1H, m), 8.09 (1H, d, J=8.5 Hz), 8.25 (1H, d, J=8.5 Hz), 9.07 (1H, d, J=4.3 Hz). MS: 397 ($M^+$+1).

Example 57

1) tert-butyl 2,2,4-trimethyl-6-(4,4,5,5-tetramethyl-[1,3,2]dioxaborolan-2-yl)-2,3,4,7,8,9-hexahydro-1H-cyclopenta[h]quinolin-3-one-1-carboxylate Using tert-butyl 6-bromo-2,2,4-trimethyl-2,3,4,7,8,9-hexahydro-1H-cyclopenta[h]quinolin-3-one-1-carboxylate (1.5 g) obtained in Example 1, 7) instead of tert-butyl 6-bromo-2,2,4,4-tetramethyl-2,3,4,7,8,9-hexahydro-1H-cyclopenta[h]quinolin-3-one-1-carboxylate of Example 1, 9) and according to a similar method, the title compound (1.7 g, 100%) was obtained.

NMR (400 MHz, CDCl$_3$) δ: 1.32 (12H, s), 1.32 (3H, br), 1.51 (9H, s), 1.52 (3H, d, J=5.2 Hz), 1.71 (3H, br), 1.84-2.01 (1H, m), 2.05-2.22 (1H, m), 2.50-2.61 (1H, m), 2.83-2.89 (1H, m), 2.91-2.96 (1H, m), 3.00-3.09 (1H, m), 3.88 (1H, br), 7.37 (1H, s).

2) tert-butyl 6-(imidazo[1,2-a]pyridin-5-yl)-2,2,4-trimethyl-2,3,4,7,8,9-hexahydro-1H-cyclopenta[h]quinolin-3-one-1-carboxylate To a solution of the compound of the previous step (2.3 g) in isopropanol (25 ml) were added 5-bromoimidazo[1,2-a]pyridine (1.1 g), 2.0M aqueous potassium carbonate solution (4.9 ml) and tetrakis(triphenylphosphine)palladium(0) (170 mg), and the mixture was stirred at 80° C. for 15 hr. The reaction mixture was diluted with water, and the mixture was extracted with ethyl acetate. The organic layer was washed with saturated brine, and dried over sodium sulfate. The solvent was evaporated under reduced pressure. The residue was subjected to normal phase chromatography (elution solvent hexane-ethyl acetate=1:1→ethyl acetate) to give the title compound (1.8 g, 81%).

NMR (300 MHz, CDCl$_3$) δ: 1.42 (3H, s), 1.47 (3H, d, J=6.6 Hz), 1.59 (9H, s), 1.77 (3H, br), 1.85-2.05 (1H, m), 2.10-2.25 (1H, m), 2.42-2.88 (3H, m), 2.91-3.10 (1H, m), 3.99 (1H, q, J=6.6 Hz), 6.69 (1H, d, J=6.9 Hz), 7.04-7.14 (2H, m), 7.22-7.27 (1H, m), 7.61 (1H, d, J=1.2 Hz), 7.64 (1H, d, J=9.3 Hz).

3) 4-allyl-6-(imidazo[1,2-a]pyridin-5-yl)-2,2,4-trimethyl-2,3,4,7,8,9-hexahydro-1H-cyclopenta[h]quinolin-3-one A solution of the compound of the previous step (80 mg) in toluene (1 ml) was cooled to −20° C., 1.0 M lithiumbis(trimethylsilyl)amide/THF solution (718 µl) was added dropwise and the mixture was stirred for 15 min. Allyl iodide (66 µl) was added, and the mixture was stirred at room temperature for 2 hr. The reaction mixture was diluted with water, and the mixture was extracted with ethyl acetate. The organic layer was washed with saturated brine, and dried over magnesium sulfate. The solvent was evaporated under reduced pressure.

Trifluoroacetic acid (1 ml) was added to the residue, and the mixture was stirred at room temperature for 30 min. Trifluoroacetic acid was evaporated and the residue was subjected to high performance liquid chromatography to give the title compound (39 mg, 57%).

NMR (300 MHz, DMSO) δ: 1.27 (3H, s), 1.33 (6H, s), 2.04-2.10 (2H, m), 2.46-2.77 (4H, m), 2.88 (2H, br), 4.95 (1H, d, J=10.4 Hz), 4.96 (1H, d, J=18.4 Hz), 5.40-5.45 (1H, m), 5.72 (1H, s), 7.23 (1H, s), 7.45 (1H, d, J=7.0 Hz), 7.82 (1H, br), 7.91-8.02 (2H, m), 8.19 (1H, s). MS: 386 ($M^+$+1).

Example 58

4-ethyl-6-(imidazo[1,2-s]pyridin-5-yl)-2,2,4-trimethyl-2,3,4,7,8,9-hexahydro-1H-cyclopenta[h]quinolin-3-one Using iodoethane instead of allyl iodide of Example 57, 3) and according to a similar method, the title compound (49 mg, 59%) was obtained.

NMR (300 MHz, DMSO) δ:0.63 (3H, t, J=7.2 Hz), 1.28 (3H, s), 1.33 (6H, s), 1.68-1.75 (1H, m), 1.90-1.94 (1H, m), 2.04-2.09 (2H, m), 2.61-2.77 (2H, m), 2.87 (2H, br), 5.68 (1H, s), 7.21 (1H, s), 7.45 (1H, dd, J=6.9, 1.2 Hz), 7.84 (1H, br), 7.91-8.02 (2H, m), 8.18 (1H, d, J=2.1 Hz). MS: 374 ($M^+$+1).

Example 59

6-(imidazo[1,2-a]pyridin-5-yl)-2,2,4-trimethyl-4-propyl-2,3,4,7,8,9-hexahydro-1H-cyclopenta[h]quinolin-3-one Using 1-iodopropane instead of allyl iodide of Example 57, 3) and according to a similar method, the title compound (48 mg, 55%) was obtained.

NMR (300 MHz, DMSO) δ:0.76 (3H, t, J=7.2 Hz), 0.93-1.03 (2H, m), 1.27 (3H, s), 1.34 (3H, s), 1.35 (3H, s), 1.61-1.71 (1H, m), 1.85-1.92 (1H, m), 2.03-2.11 (2H, m), 2.61-2.87 (4H, m), 5.67 (1H, s), 7.22 (1H, s), 7.45 (1H, dd, J=6.9, 0.9 Hz), 7.83 (1H, br), 7.91-8.02 (2H, m), 8.18 (1H, s). MS: 388 ($M^+$+1).

Example 60

4-butyl-6-(imidazo[1,2-a]pyridin-5-yl)-2,2,4-trimethyl-2,3,4,7,8,9-hexahydro-1H-cyclopenta[h]quinolin-3-one Using 1-iodobutane instead of allyl iodide of Example 57, 3) and according to a similar method, the title compound (45 mg, 50%) was obtained.

NMR (300 MHz, DMSO) δ:0.78 (3H, t, J=7.2 Hz), 0.91-1.00 (2H, m), 1.13-1.20 (2H, m), 1.27 (3H, s), 1.33 (3H, s), 1.35 (3H, s), 1.65-1.77 (1H, m), 1.81-1.90 (1H, m), 2.04-2.08 (2H, m), 2.60-2.87 (4H, m), 5.66 (1H, s), 7.22 (1H, s), 7.43 (1H, dd, J=6.9, 1.2 Hz), 7.81 (1H, br), 7.90-8.00 (2H, m), 8.17 (1H, d, J=1.8 Hz). MS: 402 (M$^+$+1)

Example 61

6-(imidazo[1,2-a]pyridin-5-yl)-2,2,4-trimethyl-4-(3-methylbutyl)-2,3,4,7,8,9-hexahydro-1H-cyclopenta[h]quinolin-3-one Using 1-iodo-3-methylbutane instead of allyl iodide of Example 57, 3) and according to a similar method, the title compound (43 mg, 46%) was obtained.
NMR (300 MHz, DMSO) δ:0.77 (6H, d, J=0.6 Hz), 0.87-0.92 (2H, m), 1.27 (3H, s), 1.33 (6H, s), 1.27-1.41 (1H, m), 1.74-1.80 (2H, m), 2.04-2.11 (2H, m), 2.59-2.87 (4H, m), 5.67 (1H, s), 7.22 (1H, s), 7.45 (1H, d, J=6.9 Hz), 7.82 (1H, br), 7.91-8.03 (2H, m), 8.19 (1H, s). MS: 416 (M$^+$+1).

Example 62

4-(2-butenyl)-6-(imidazo[1,2-a]pyridin-5-yl)-2,2,4-trimethyl-2,3,4,7,8,9-hexahydro-1H-cyclopenta[h]quinolin-3-one Using crotyl bromide instead of allyl iodide of Example 57, 3) and according to a similar method, the title compound (33 mg, 37%) was obtained.
NMR (300 MHz, DMSO) δ: 1.27 (3H, s), 1.31 (3H, d, J=5.1 Hz), 1.34 (3H, s), 1.69 (3H, d, J=6.3 Hz), 2.04-2.11 (2H, m), 2.43-2.54 (1H, m), 2.65-2.90 (5H, m), 5.06-5.11 (1H, m), 5.31-5.46 (1H, m), 5.70 (1H, br), 7.29 (1H, d, J=7.8 Hz), 7.45 (1H, d, J=6.6 Hz), 7.81 (1H, br), 7.91-8.03 (2H, m), 8.20 (1H, s). MS: 400 (M$^+$+1).

Example 63

4-(2-butynyl)-6-(imidazo[1,2-a]pyridin-5-yl)-2,2,4-trimethyl-2,3,4,7,8,9-hexahydro-1H-cyclopenta[h]quinolin-3-one Using 1-bromo-2-butyne instead of allyl iodide of Example 57, 3) and according to a similar method, the title compound (43 mg, 48%) was obtained.
NMR (300 MHz, DMSO) δ: 1.30 (3H, s), 1.33 (6H, s), 1.67 (3H, s), 2.06 (2H, br), 2.61-2.88 (6H, m), 5.76 (1H, br), 7.31 (1H, s), 7.47 (1H, d, J=6.0 Hz), 7.88-8.03 (3H, m), 8.24 (1H, s). MS: 398 (M$^+$+1)

Example 64

1) tert-butyl 6-bromo-2,2,4-trimethyl-4-(2-methylethyl)-2,3,4,7,8,9-hexahydro-1H-cyclopenta[h]quinolin-3-one-1-carboxylate A solution of tert-butyl 6-bromo-2,2,4-trimethyl-2,3,4,7,8,9-hexahydro-1H-cyclopenta[h]quinolin-3-one-1-carboxylate (300 mg) obtained in Example 1, 7) in toluene (3 ml) was cooled to −20° C., 1.0 M lithiumbis(trimethylsilyl)amide/THF solution (2.9 ml) was added dropwise and the mixture was stirred for 15 min. 2-Iodopropane (293 μl) was added, and the mixture was stirred at 70° C. for 13 hr. The reaction mixture was diluted with water, and the mixture was extracted with ethyl acetate. The organic layer was washed with saturated brine, and dried over magnesium sulfate. The solvent was evaporated under reduced pressure. The residue was subjected to normal phase chromatography (elution solvent hexane-ethyl acetate=20:1→10:1) to give the title compound (136 mg, 41%).
NMR (300 MHz, CHCl$_3$) δ:0.75 (3H, d, J=6.8 Hz), 0.87 (3H, d, J=6.9 Hz), 1.21 (3H, s), 1.27 (3H, s), 1.46 (9H, s), 1.80 (3H, s), 1.98-2.05 (1H, m), 2.08-2.20 (1H, m), 2.57-2.62 (1H, m), 2.83-3.01 (4H, m), 7.10 (1H, s).

2) 6-(imidazo[1,2-a]pyridin-5-yl)-2,2,4-trimethyl-4-(2-methylethyl)-2,3,4,7,8,9-hexahydro-1H-cyclopenta[h]quinolin-3-one Using the compound of the previous step (136 mg) instead of tert-butyl 6-bromo-2,2,4,4-tetramethyl-2,3,4,7,8,9-hexahydro-1H-cyclopenta[h]quinolin-3-one-1-carboxylate of Example 1, 9) and according to a similar method, tert-butyl 2,2,4-trimethyl-4-(2-methylethyl)-6-(4,4,5,5-tetramethyl-[1,3,2]dioxoborolan-2-yl)-2,3,4,7,8,9-hexahydro-1H-cyclopenta[h]-quinolin-3-one-1-carboxylate (96 mg, 64%) was obtained.
Then, using the obtained compound (96 mg) instead of tert-butyl 2,2,4,4-tetramethyl-6-(4,4,5,5-tetramethyl-[1,3,2]dioxaborolan-2-yl)-2,3,4,7,8,9-hexahydro-1H-cyclopenta[h]quinolin-3-one-1-carboxylate of Example 1, 10), 5-bromoimidazo[1,2-a]pyridine instead of 4-bromo-3-chlorophenol of Example 1, 10) and according to a similar method, the title compound (71 mg, 95%) was obtained.
NMR (300 MHz, DMSO) δ:0.60 (3H, d, J=6.6 Hz), 0.76 (3H, d, J=6.9 Hz), 1.18 (3H, s), 1.26 (3H, s), 1.43 (3H, s), 2.04-2.09 (2H, m), 2.54-2.64 (2H, m), 2.83-2.92 (3H, m), 5.68 (1H, s), 7.13 (1H, s), 7.44 (1H, dd, J=6.9, 1.2 Hz), 7.78 (1H, br), 7.91-8.01 (2H, m), 8.17 (1H, s). MS: 388 (M$^+$+1).

Example 65

1) tert-butyl 6-bromo-2,2,4-trimethyl-4-(2-methylallyl)-2,3,4,7,8,9-hexahydro-1H-cyclopenta[h]quinolin-3-one-1-carboxylate Using 3-bromo-2-methylpropene instead of 2-iodopropane of Example 64, 1) and according to a similar method, the title compound (325 mg, 96%) was obtained.
NMR (300 MHz, CHCl$_3$) δ: 1.23 (3H, br), 1.42 (3H, s), 1.48 (12H, s), 1.82 (3H, br), 1.93-2.05 (1H, m), 2.10-2.22 (1H, m), 2.24 (1H, d, J=13.1 Hz), 2.69-2.80 (1H, m), 2.89-3.00 (4H, m), 4.57 (1H, s), 4.85 (1H, s), 7.12 (1H, s).

2) 6-(imidazo[1,2-a]pyridin-5-yl)-2,2,4-trimethyl-4-(2-methylallyl)-2,3,4,7,8,9-hexahydro-1H-cyclopenta[h]quinolin-3-one Using the compound of the previous step instead of tert-butyl 6-bromo-2,2,4-trimethyl-4-(2-methylethyl)-2,3,4,7,8,9-hexahydro-1H-cyclopenta[h]quinolin-3-one-1-carboxylate of Example 64, 2) and according to a similar method, the title compound (21 mg, 7%) was obtained.
NMR (300 MHz, DMSO) δ: 1.28 (3H, s), 1.38 (3H, s), 1.40 (6H, s), 2.03-2.08 (2H, m), 2.32 (1H, d, J=13.7 Hz), 2.50-2.90 (5H, m), 4.40 (1H, s), 4.70 (1H, br), 5.73 (1H, s), 7.20 (1H, s), 7.36-7.41 (2H, m), 7.90-8.00 (2H, m), 8.19 (1H, s). MS: 400 (M$^+$+1).

Example 66

1) tert-butyl 6-bromo-2,2,4-trimethyl-4-(3-methyl-2-butenyl)-2,3,4,7,8,9-hexahydro-1H-cyclopenta[h]quinolin-3-one-1-carboxylate Using 4-bromo-2-methyl-2-butene instead of 2-iodopropane of Example 64, 1) and according to a similar method, the title compound (358 mg, 100%) was obtained.

NMR (300 MHz, CHCl$_3$) δ: 1.30 (3H, s), 1.41 (9H, s), 1.49 (6H, s), 1.60 (3H, br), 1.86-1.97 (1H, m), 2.01-2.12 (1H, m), 2.40-2.58 (2H, m), 2.68 (1H, br), 2.85-2.90 (3H, m), 4.83 (1H, t, J=1.6 Hz), 7.05 (1H, s).

2) 6-(imidazo[1,2-a]pyridin-5-yl)-2,2,4-trimethyl-4-(3-methyl-2-butenyl)-2,3,4,7,8,9-hexahydro-1H-cyclopenta[h]quinolin-3-one Using the compound of the previous step instead of tert-butyl 6-bromo-2,2,4-trimethyl-4-(2-methylethyl)-2,3,4,7,8,9-hexahydro-1H-cyclopenta[h]quinolin-3-one-1-carboxylate of Example 64, 2) and according to a similar method, the title compound (45 mg, 15%) was obtained.

NMR (300 MHz, DMSO) δ: 1.26 (3H, s), 1.32 (3H, s), 1.33 (3H, s), 1.42 (3H, s), 1.58 (3H, s), 2.02-2.08 (2H, m), 2.29-2.36 (1H, m), 2.54-2.88 (5H, m), 4.81 (1H, br), 5.71 (1H, s), 7.15 (1H, s), 7.42 (1H, d, J=7.0 Hz), 7.79 (1H, br), 7.90-8.02 (2H, m), 8.20 (1H, s). MS: 414 (M$^+$+1).

Example 67

1) tert-butyl 6-bromo-2,2,4-trimethyl-4-(3,3,3-trifluoropropyl)-2,3,4,7,8,9-hexahydro-1H-cyclopenta[h]quinolin-3-one-1-carboxylate Using 1,1,1-trifluoro-3-iodopropane instead of 2-iodopropane of Example 64, 1) and according to a similar method, the title compound (74 mg, 6%) was obtained.

NMR (300 MHz, CHCl$_3$) δ: 1.44 (3H, s), 1.47 (9H, s), 1.50 (3H, s), 1.52 (3H, s), 1.95-2.98 (10H, m), 7.13 (1H, s).

2) 6-(imidazo[1,2-a]pyridin-5-yl)-2,2,4-trimethyl-4-(3,3,3-trifluoropropyl)-2,3,4,7,8,9-hexahydro-1H-cyclopenta[h]quinolin-3-one Using the compound of the previous step instead of tert-butyl 6-bromo-2,2,4-trimethyl-4-(2-methylethyl)-2,3,4,7,8,9-hexahydro-1H-cyclopenta[h]quinolin-3-one-1-carboxylate of Example 64, 2) and according to a similar method, the title compound (14 mg, 53%) was obtained.

NMR (300 MHz, DMSO) δ: 1.31 (3H, s), 1.34 (3H, s), 1.40 (3H, s), 1.92-2.14 (6H, m), 2.51-2.91 (4H, m), 5.74 (1H, s), 7.25 (1H, s), 7.39 (1H, d, J=6.2 Hz), 7.85-7.92 (3H, m), 8.12 (1H, s). MS: 442 (M$^+$+1)

Example 68

1) ethyl 2,3-dihydroxybenzoate

To a solution of 2,3-dihydroxybenzoic acid (25 g) in ethanol (320 ml) was added concentrated sulfuric acid (1.8 ml), and the mixture was heated under reflux for one day. The reaction mixture was concentrated, poured into water, and the mixture was extracted with ethyl acetate. The organic layer was washed with saturated brine, and dried over sodium sulfate. The solvent was evaporated under reduced pressure. The residue was subjected to normal phase chromatography (elution solvent ethyl acetate) to give the title compound (30 g, 100%).

NMR (300 MHz, CDCl$_3$) δ: 1.42 (3H, t, J=7.2 Hz), 4.42 (2H, q, J=7.2 Hz), 6.80 (1H, dd, J=8.1, 7.8 Hz), 7.11 (1H, dd, J=7.8, 1.5 Hz), 7.38 (1H, dd, J=8.1, 1.5 Hz), 10.99 (1H, s).

2) ethyl 1,3-benzodioxole-4-carboxylate

To a solution of the compound of the previous step (22 g) in DMF (200 ml) were added potassium fluoride (36 g) and CH$_2$Cl$_2$ (9.0 ml), and the mixture was stirred at 110° C. for 8 hr. CH$_2$Cl$_2$ (20 ml) was added to the solution, and the mixture was further stirred at 110° C. for 6.5 hr. The reaction solution was poured into water, and the mixture was extracted with ethyl acetate. The organic layer was washed with saturated brine, and dried over magnesium sulfate. The solvent was evaporated under reduced pressure. The residue was subjected to normal phase chromatography (elution solvent hexane-ethyl acetate=4:1) to give the title compound (16 g, 68%).

NMR (300 MHz, CDCl$_3$) δ: 1.39 (3H, t, J=7.2 Hz), 4.39 (2H, q, J=7.2 Hz), 6.10 (2H, s), 6.86 (1H, dd, J=8.1, 7.2 Hz), 6.97 (1H, dd, J=7.2, 1.2 Hz), 7.41 (1H, dd, J=8.1, 1.2 Hz).

3) 1,3-benzodioxole-4-carboxylic acid

To a solution of the compound of the previous step (16 g) in methanol (170 ml) was added a solution of sodium hydroxide (9.9 g) in water (40 ml), and the mixture was stirred at room temperature for 3.5 hr. The reaction solution was acidified with concentrated hydrochloric acid, and the mixture was concentrated. The resulting precipitate was collected by filtration to give the title compound (13 g, 95%).

NMR (300 MHz, CDCl$_3$) δ: 6.14 (2H, s), 6.90 (1H, t, J=7.8 Hz), 7.03 (1H, dd, J=7.5, 1.2 Hz), 7.46 (1H, dd, J=8.1, 1.2 Hz).

4) 1,3-benzodioxol-4-amine

To a solution of the compound of the previous step (13 g) in acetone (200 ml) were added triethylamine (12 ml) and ethyl chlorocarbonate (8.0 ml) under ice-cooling, and the mixture was stirred for 30 min. Then, sodium azide (5.5 g) was added to the solution under ice-cooling, and the mixture was stirred for 1 hr. The reaction solution was poured into water, and the mixture was extracted with ethyl acetate. The organic layer was washed with saturated brine, and dried over magnesium sulfate. The solvent was evaporated under reduced pressure.

Toluene (160 ml) was added to the residue, and the mixture was heated under reflux for 1 hr. tert-Butanol (40 ml) was added, and the mixture was further heated under reflux for 3.5 hr. The reaction solution was concentrated, ethyl acetate was added, and the precipitate was removed by filtration. The solvent was evaporated under reduced pressure.

The residue was dissolved in CHCl$_3$ (50 ml), trifluoroacetic acid (30 ml) was added, and the mixture was stirred at room temperature for 8 hr.

The reaction solution was poured into aqueous sodium hydroxide solution, and the mixture was extracted with ethyl acetate. The organic layer was washed with saturated brine, and dried over sodium sulfate. The solvent was evaporated under reduced pressure to give the title compound (13 g, 100%).

NMR (300 MHz, CDCl$_3$) δ: 3.57 (2H, br), 5.92 (2H, s), 6.30-6.36 (2H, m), 6.67 (1H, dd, J=7.8, 0.3 Hz).

5) 6,8,8-trimethyl-8,9-dihydro-[1,3]dioxolo[4,5-h]quinoline

Using the compound of the previous step (11 g) instead of 4-aminoindane of Example 1, 1) and according to a similar method, the title compound (7.9 g, 46%) was obtained.

NMR (300 MHz, CDCl$_3$) δ: 1.29 (6H, s), 1.96 (3H, s), 3.64 (1H, br), 5.23 (1H, s), 5.90 (2H, s), 6.21 (1H, d, J=8.1 Hz), 6.62 (1H, d, J=8.1 Hz).

6) 6,8,8-trimethyl-6,7,8,9-tetrahydro-[1,3]dioxolo[4,5-h]quinolin-7-ol

Using the compound of the previous step (7.9 g) instead of 2,2,4-trimethyl-2,7,8,9-tetrahydro-1H-cyclopenta[h]quinoline of Example 1, 2) and according to a similar method, the title compound (9.4 g, 100%) was obtained.

NMR (300 MHz, CDCl$_3$) δ: 1.11 (6H, s), 1.32 (3H, s), 1.41 (3H, d, J=6.6 Hz), 1.73 (1H, d, J=6.3 Hz), 2.64-2.73 (1H, m), 3.34 (1H, dd, J=9.3, 6.0 Hz), 3.61 (1H, br), 5.90 (2H, dd, J=11.0, 1.5 Hz), 6.30 (1H, d, J=8.1 Hz), 6.68 (1H, dd, J=8.1, 1.2 Hz).

7) 4-bromo-6,8,8-trimethyl-6,7,8,9-tetrahydro-[1,3]dioxolo[4,5-h]quinoline-7-ol bromate To a solution of the compound of the previous step (7.9 g) in CHCl$_3$ (180 ml) was added dropwise bromine (2.0 ml) under ice-cooling, and the mixture was stirred at room temperature overnight. The reaction solution was concentrated under reduced pressure, ethyl acetate was added, and the precipitated crystals were collected by filtration to give the title compound (13 g, 93%).

NMR (300 MHz, DMSO) δ:0.93 (6H, s), 1.20 (3H, s), 1.25 (3H, d, J=6.6 Hz), 1.97 (1H, d, J=10.0 Hz), 2.97 (1H, d, J=10.0 Hz), 5.99 (2H, d, J=11.0 Hz), 6.76 (1H, s).

8) 4-bromo-7-(tert-butyldimethylsilyloxy)-6,8,8-trimethyl-6,7,8,9-tetrahydro-[1,3]dioxolo[4,5-h]quinoline Using the compound of the previous step (13 g) instead of 6-bromo-2,2,4-trimethyl-2,3,4,7,8,9-hexahydro-1H-cyclopenta[h]quinolin-3-ol of Example 1, 4) and according to a similar method, the title compound (9.7 g, 67%) was obtained.

NMR (300 MHz, CDCl$_3$) δ:0.11 (3H, s), 0.13 (3H, s), 0.94 (9H, s), 1.06 (3H, s), 1.23 (3H, s), 1.30 (3H, d, J=9.5 Hz), 2.61-2.73 (1H, m), 3.36 (1H, d, J=9.1 Hz), 3.53 (1H, br), 5.96 (1H, d, J=7.2 Hz), 5.96 (1H, d, J=7.2 Hz), 6.77 (1H, s).

9) tert-butyl 4-bromo-7-hydroxy-6,8,8-trimethyl-6,7,8,9-tetrahydro-[1,3]dioxolo[4,5-h]quinoline-9-carboxylate A solution of the compound of the previous step (9.7 g) in THF (200 ml) was cooled to −78° C., 1.6M n-butyllithium-hexane solution (16 ml) was added dropwise, and the mixture was heated to room temperature with stirring. Di-tert-butyl (5.9 g) was added to the solution, and the mixture was stirred at room temperature overnight. Production of tert-butyl 4-bromo-7-(tert-butyldimethylsilyloxy)-6,8,8-trimethyl-6,7,8,9-tetrahydro-[1,3]dioxolo[4,5-h]quinoline-9-carboxylate was confirmed by LC-MS.

Then, tetrabutylammonium fluoride (30 ml) was added to the reaction solution, and the mixture was stirred at 60° C. for 7 hr. The reaction solution was poured into water, and the mixture was extracted with ethyl acetate. The organic layer was washed with saturated brine, dried over sodium sulfate, and the solvent was evaporated under reduced pressure. The residue was subjected to normal phase chromatography (elution solvent hexane-ethyl acetate=4:1) to give the title compound (5.0 g, 53%).

NMR (300 MHz, CDCl$_3$) δ: 1.35 (3H, d, J=6.9 Hz), 1.45 (12H, s), 1.59 (3H, s), 1.87 (1H, d, J=6.3 Hz), 2.68-2.82 (1H, m), 3.08 (1H, dd, J=9.9, 6.3 Hz), 6.03 (1H, d, J=20.0 Hz), 6.04 (1H, d, J=20.0 Hz), 6.75 (1H, d, J=1.8 Hz).

10) tert-butyl 4-bromo-6,8,8-trimethyl-6,7,8,9-tetrahydro-[1,3]dioxolo[4,5-h]quinolin-7-one-9-carboxylate Using the compound of the previous step (5.0 g) instead of tert-butyl 6-bromo-3-hydroxy-2,2,4-trimethyl-2,3,4,7,8,9-hexahydro-1H-cyclopenta[h]quinoline-1-carboxylate of Example 1, 7) and according to a similar method, the title compound (2.9 g, 60%) was obtained.

NMR (300 MHz, CDCl$_3$) δ: 1.40 (3H, s), 1.42 (3H, d, J=6.6 Hz), 1.48 (9H, s), 1.72 (3H, s), 3.82 (1H, q, J=6.6 Hz), 6.08 (1H, d, J=17.0 Hz), 6.08 (1H, d, J=17.0 Hz), 6.73 (1H, d, J=1.2 Hz).

11) tert-butyl 4-bromo-6,6,8,8-tetramethyl-6,7,8,9-tetrahydro-[1,3]dioxolo[4,5-h]quinolin-7-one-9-carboxylate Using the compound of the previous step (500 mg) instead of tert-butyl 6-bromo-2,2,4-trimethyl-2,3,4,7,8,9-hexahydro-1H-cyclopenta[h]quinolin-3-one-1-carboxylate of Example 1, 8) and according to a similar method, the title compound (470 mg, 91%) was obtained.

NMR (300 MHz, CDCl$_3$) δ: 1.46 (6H, s), 1.47 (9H, s), 1.57 (6H, s), 6.08 (2H, s), 6.84 (1H, s).

12) tert-butyl 6,6,8,8-tetramethyl-4-(4,4,5,5-tetramethyl-[1,3,2]dioxaborolan-2-yl)-6,7,8,9-tetrahydro-[1,3]dioxolo[4,5-h]quinolin-7-one-9-carboxylate Using the compound of the previous step (274 mg) instead of tert-butyl 6-bromo-2,2,4-trimethyl-2,3,4,7,8,9-hexahydro-1H-cyclopenta[h]quinolin-3-one-1-carboxylate of Example 1, 9) and according to a similar method, the title compound (297 mg, 98%) was obtained.

NMR (300 MHz, CDCl$_3$) δ: 1.36 (12H, s), 1.46 (9H, s), 1.49 (6H, s), 1.56 (6H, s), 6.06 (2H, s), 7.07 (1H, s).

13) 4-(4-hydroxy-2-methylphenyl)-6,6,8,8-tetramethyl-6,7,8,9-tetrahydro-[1,3]dioxolo[4,5-h]quinolin-7-one Using the compound of the previous step instead of tert-butyl 2,2,4,4-tetramethyl-6-(4,4,5,5-tetramethyl-[1,3,2]dioxaborolan-2-yl)-2,3,4,7,8,9-hexahydro-1H-cyclopenta[h]quinolin-3-one-1-carboxylate of Example 1, 10), 4-bromo-3-methylphenol instead of 4-bromo-3-chlorophenol of Example 1, 10) and according to a similar method, the title compound (12 mg, 39%) was obtained.

NMR (300 MHz, DMSO) δ: 1.26 (6H, s), 1.33 (6H, s), 2.13 (3H, s), 5.53 (1H, br), 5.98 (2H, s), 6.52 (1H, s), 6.61 (1H, dd, J=8.4, 2.4 Hz), 6.65 (1H, d, J=2.4 Hz), 7.01 (1H, d, J=8.4 Hz), 9.30 (1H, br). MS: 354 (M$^+$+1).

Example 69

4-(3,5-dimethylisoxazol-4-yl)-6,6,8,8-tetramethyl-6,7,8,9-tetrahydro-[1,3]dioxolo[4,5-h]quinolin-7-one Using 4-iodo-3,5-dimethylisoxazole instead of 4-bromo-3-methylphenol of Example 68, 13) and according to a similar method, the title compound (37 mg, 69%) was obtained.
NMR (300 MHz, CDCl$_3$)δ:1.38(6H, s), 1.44(6H, s), 2.26 (3H, s), 2.38(3H, s), 5.99(2H, s), 6.54(1H, s).MS:343(M$^+$+1).

Example 70

4-(1H-indol-7-yl)-6,6,8,8-tetramethyl-6,7,8,9-tetrahydro-[1,3]dioxolo[4,5-h]quinolin-7-one Using 7-bromoindole instead of 4-bromo-3-methylphenol of Example 68, 13) and according to a similar method, the title compound (28 mg, 51%) was obtained.
NMR (300 MHz, DMSO)δ:1.30(6H, s), 1.39(6H, s), 5.68 (1H, s), 6.11(2H, s), 6.47(1H, dd, J=3.0, 1.8 Hz), 6.83(1H, s), 7.02-7.12(2H, m), 7.29(1H, dd, J=3.0, 2.7 Hz), 7.51(1H, d, J=7.5 Hz), 10.66(1H, br).MS:363(M$^+$+1).

Example 71

4-(imidazo[1,2-a]pyridin-5-yl)-6,6,8,8-tetramethyl-6,7,8,9-tetrahydro-[1,3]dioxolo[4,5-h]quinolin-7-one Using 5-bromoimidazo[1,2-a]pyridine instead of 4-bromo-3-methylphenol of Example 68, 13) and according to a similar method, the title compound (18 mg, 38%) was obtained.
NMR (400 MHz, DMSO)δ:1.32(6H, s), 1.39(6H, s), 6.19 (2H, s), 6.26(1H, s), 7.02(1H, s), 7.54(1H, dd, J=7.0, 1.2 Hz), 7.93-8.01(2H, m), 8.22-8.24(2H, m).MS:364(M$^+$+1).

Example 72

6,6,8,8-tetramethyl-4-(quinolin-5-yl)-6,7,8,9-tetrahydro-[1,3]dioxolo[4,5-h]quinolin-7-one Using 5-bromoquinoline instead of 4-bromo-3-methylphenol of Example 68, 13) and according to a similar method, the title compound (24 mg, 69%) was obtained.
NMR (300 MHz, DMSO)δ:1.32(6H, s), 1.39(6H, s), 5.85 (1H, br), 6.05(2H, s), 6.80(1H, s), 7.67-7.72(2H, m), 7.93 (1H, dd, J=8.5, 7.3 Hz), 8.10(1H, d, J=8.5 Hz), 8.47(1H, d, J=8.5 Hz), 9.05(1H, dd, J=4.5, 1.5 Hz).MS:375(M$^+$+1).

Example 73

6,6,8,8-tetramethyl-4-([1,8]naphthyridin-4-yl)-6,7,8,9-tetrahydro-[1,3]dioxolo[4,5-h]quinolin-7-one Using 4-chloro[1,8]naphthyridine instead of 4-bromo-3-methylphenol of Example 68, 13) and according to a similar method, the title compound (14 mg, 29%) was obtained.
NMR (400 MHz, DMSO)δ:1.32(6H, s), 1.40(6H, s), 6.12 (2H, s), 6.14(1H, s), 6.92(1H, s), 7.75(1H, dd, J=8.5, 4.2 Hz), 7.79(1H, d, J=4.9 Hz), 8.57(1H, dd, J=8.5, 1.8 Hz), 9.16-9.18 (2H, m).MS:376(M$^+$+1).

Example 74

1) tert-butyl 6-allyl-4-bromo-6,8,8-trimethyl-6,7,8,9-tetrahydro-[1,3]dioxolo[4,5-h]quinolin-7-one-9-carboxylate Using tert-butyl 4-bromo-6,8,8-trimethyl-6,7,8,9-tetrahydro-[1,3]dioxolo[4,5-h]quinolin-7-one-9-carboxylate (500 mg) obtained in Example 68, 10) instead of tert-butyl 6-bromo-2,2,4-trimethyl-2,3,4,7,8,9-hexahydro-1H-cyclopenta[h]quinolin-3-one-1-carboxylate of Example 1, 8), allyl iodide instead of iodomethane of Example 1, 8) and according to a similar method, the title compound (584 mg, 100%) was obtained.
NMR (300 MHz, CDCl$_3$)δ:1.36(3H, s), 1.39(3H, s), 1.47 (9H, s), 1.76(3H, s), 2.45(1H, dd, J=13.8, 7.2 Hz), 2.71(1H, dd, J=13.8, 7.5 Hz), 4.99(1H, dd, J=17.1, 1.8 Hz), 5.06(1H, dd, J=10.2, 1.8 Hz), 5.51-5.60(1H, m), 6.08(1H, d, J=7.2 Hz), 6.09(1H, d, J=7.2 Hz), 6.77(1H, s).

2) tert-butyl 6-allyl-4-(4,4,5,5-tetramethyl-[1,3,2]dioxaborolan-2-yl)-6,8,8-trimethyl-6,7,8,9-tetrahydro-[1,3]dioxolo[4,5-h]quinoline-7-one-9-carboxylate Using the compound of the previous step (350 mg) instead of tert-butyl 6-bromo-2,2,4,4-tetramethyl-2,3,4,7,8,9-hexahydro-1H-cyclopenta[h]quinolin-3-one-1-carboxylate of Example 1, 9) and according to a similar method, the title compound (478 mg, 100%) was obtained.
NMR (300 MHz, CDCl$_3$)δ:1.36(12H, s), 1.46(9H, s), 1.58 (6H, s), 1.76(3H, s), 2.51(1H, dd, J=13.8, 6.8 Hz), 2.70(1H, dd, J=13.8, 7.5 Hz), 4.99(1H, dd, J=19.6, 1.8 Hz), 7.05(1H, d, J=8.3, 1.8 Hz), 5.52-5.58(1H, m), 6.07(1H, d, J=6.3 Hz), 6.07(1H, d, J=6.3 Hz), 7.01(1H, s).

3) 6-allyl-4-(4-hydroxy-2-methoxyphenyl)-6,8,8-trimethyl-6,7,8,9-tetrahydro-[1,3]dioxolo[4,5-h]quinoline-7-one Using the compound of the previous step instead of tert-butyl 2,2,4,4-tetramethyl-6-(4,4,5,5-tetramethyl-[1,3,2]dioxaborolan-2-yl)-2,3,4,7,8,9-hexahydro-1H-cyclopenta[h]quinolin-3-one-1-carboxylate of Example 1, 10), 4-bromo-3-methoxyphenol instead of 4-bromo-3-chlorophenol of Example 1, 10) and according to a similar method, the title compound (6.4 mg, 16%) was obtained.
NMR (300 MHz, DMSO)δ:1.21(3H, s), 1.27(3H, s), 1.29 (3H, s), 2.43(1H, dd, J=13.8, 7.5 Hz), 2.61(1H, dd, J=13.8, 6.6 Hz), 3.69(3H, s), 4.96(1H, d, J=14.7 Hz), 4.97(1H, d, J=11.7 Hz), 5.36-5.48(1H, m), 5.48(1H, s), 5.96(2H, d, J=14.4 Hz), 6.39(1H, dd, J=8.1, 2.1 Hz), 6.46(1H, d, J=2.1 Hz), 6.66(1H, s), 7.07(1H, d, J=8.1 Hz), 9.48(1H, s).MS:396 (M$^+$+1).

Example 75

6-allyl-4-(3,5-dimethylisoxazol-4-yl)-6,8,8-trimethyl-6,7,8,9-tetrahydro-[1,3]dioxolo[4,5-h]quinolin-7-one Using 4-iodo-3,5-dimethylisoxazole instead of 4-bromo-3-methoxyphenol of Example 74, 3) and according to a similar method, the title compound (32 mg, 40%) was obtained.
NMR (300 MHz, CDCl$_3$)δ:1.33(3H, s), 1.40(3H, s), 1.41 (3H, s), 2.26(3H, s), 2.37(3H, s), 2.39(1H, dd, J=14.0, 7.5 Hz), 2.79(1H, dd, J=14.0, 6.9 Hz), 4.96(1H, dd, J=9.3, 1.8

Hz), 4.97(1H, dd, J=16.8, 1.8 Hz), 5.42-5.54(1H, m), 5.99 (1H, d, J=12.0 Hz), 6.00(1H, d, J=12.0 Hz), 6.48(1H, s).MS: 369(M$^+$+1).

Example 76

6-allyl-4-(2-cyano-3-methylthiophen-4-yl)-6,8,8-trimethyl-6,7,8,9-tetrahydro-[1,3]dioxolo[4,5-h]quinolin-7-one Using 4-bromo-3-methylthiophene-2-carbonitrile instead of 4-bromo-3-methoxyphenol of Example 74, 3) and according to a similar method, the title compound (11 mg, 28%) was obtained.

NMR (300 MHz, DMSO)δ:1.22(3H, s), 1.28(3H, s), 1.33 (3H, s), 2.35(3H, s), 2.45(1H, dd, J=13.8, 7.2 Hz), 2.62(1H, dd, J=13.8, 6.9 Hz), 4.94(1H, d, J=15.3 Hz), 4.95(1H, d, J=11.9 Hz), 5.34-5.48(1H, m), 5.78(1H, s), 6.06(2H, d, J=15.1 Hz), 6.68(1H, s), 7.90(1H, s).MS:395(M$^+$+1).

Example 77

6-allyl-4-(2-methoxypyridin-3-yl)-6,8,8-trimethyl-6,7,8,9-tetrahydro-[1,3]dioxolo[4,5-h]quinolin-7-one Using 3-iodo-2-methoxypyridine instead of 4-bromo-3-methoxyphenol of Example 74, 3) and according to a similar method, the title compound (11 mg, 28%) was obtained.

NMR (300 MHz, DMSO)δ:1.23(3H, s), 1.28(3H, s), 1.31 (3H, s), 2.46(1H, dd, J=13.8, 7.4 Hz), 2.62(1H, dd, J=13.8, 6.8 Hz), 3.86(3H, s), 4.97(1H, d, J=14.3 Hz), 4.97(1H, d, J=12.0 Hz), 5.39-5.48(1H, m), 5.69(1H, br), 6.02(1H, d, J=14.6 Hz), 6.03(1H, d, J=14.6 Hz), 6.84(1H, s), 7.04(1H, dd, J=7.3, 4.9 Hz), 7.73(1H, dd, J=7.3, 1.9 Hz), 8.12(1H, dd, J=4.9, 1.9 Hz).MS:381(M$^+$+1).

Example 78

6-allyl-4-(1H-indol-7-yl)-6,8,8-trimethyl-6,7,8,9-tetrahydro-[1,3]dioxolo[4,5-h]quinolin-7-one Using 7-bromoindole instead of 4-bromo-3-methoxyphenol of Example 74, 3) and according to a similar method, the title compound (26 mg, 55%) was obtained.

NMR (300 MHz, DMSO)δ:1.26(3H, s), 1.31(3H, s), 1.36 (3H, s), 2.54-2.67(2H, m), 4.97(1H, d, J=11.7 Hz), 4.98(1H, d, J=15.6 Hz), 5.42-5.51(1H, m), 5.67(1H, s), 6.11(1H, d, J=5.7 Hz), 6.12(1H, d, J=5.7 Hz), 6.48(1H, dd, J=3.0, 1.8 Hz), 6.79(1H, s), 7.03-7.09(2H, m), 7.29(1H, dd, J=3.0, 2.7 Hz), 7.52(1H, dd, J=6.6, 2.4 Hz), 10.63(1H, br).MS:389(M$^+$+1).

Example 79

6-allyl-6,8,8-trimethyl-4-(quinolin-5-yl)-6,7,8,9-tetrahydro-[1,3]dioxolo[4,5-h]quinolin-7-one Using 5-bromoquinoline instead of 4-bromo-3-methoxyphenol of Example 74, 3) and according to a similar method, the title compound (10 mg, 29%) was obtained.

NMR (300 MHz, DMSO)δ:1.28(3H, s), 1.33(3H, s), 1.35 (3H, s), 2.46-2.54(1H, m), 2.68(1H, dd, J=13.1, 7.2 Hz), 4.97(1H, d, J=15.4 Hz), 5.00(1H, d, J=8.2 Hz), 5.35-5.51(1H, m), 5.86(1H, br), 6.04(2H, d, J=4.5 Hz), 6.76(1H, s), 7.68-7.72(2H, m), 7.93(1H, dd, J=7.1, 6.6 Hz), 8.10(1H, d, J=8.4 Hz), 8.46(1H, d, J=8.4 Hz), 9.06(1H, d, J=3.9 Hz).MS:401 (M$^+$+1).

Example 80

4-(3,5-dimethylisoxazol-4-yl)-2,2-difluoro-6,6,8,8-tetramethyl-6,7,8,9-tetrahydro-[1,3]dioxolo[4,5-h]quinolin-7-one Using 4-amino-2,2-difluoro-1,3-benzodioxole instead of 4-aminoindane of Example 1, 1), 4-iodo-3,5-dimethylisoxazole instead of 4-bromo-3-chlorophenol of Example 1, 10) and according to the method of Example 1, 1)-10), the title compound (5.0 mg, 1%) was obtained.

NMR (300 MHz, CDCl$_3$)δ:1.41(6H, s), 1.46(6H, s), 2.27 (3H, s), 2.40(3H, s), 3.93(1H, s), 6.76(1H, s).MS:379(M$^+$+1).

Example 81

4-(2-cyano-3-methylthiophen-4-yl)-2,2-difluoro-6,6,8,8-tetramethyl-6,7,8,9-tetrahydro-[1,3]dioxolo[4,5-h]quinolin-7-one Using 4-bromo-3-methylthiophene-2-carbonitrile instead of 4-iodo-3,5-dimethylisoxazole of Example 80 and according to a similar method, the title compound (7.6 mg, 19%) was obtained.

NMR (400 MHz, DMSO)δ:1.30(6H, s), 1.39(6H, s), 2.36 (3H, s), 6.58(1H, s), 7.07(1H, s), 8.06(1H, s).MS:405(M$^+$+1).

Example 82

2,2-difluoro-4-(imidazo[1,2-a]pyridin-5-yl)-6,6,8,8-tetramethyl-6,7,8,9-tetrahydro-[1,3]dioxolo[4,5-h]quinolin-7-one Using 5-bromoimidazo[1,2-a]pyridine instead of 4-iodo-3,5-dimethylisoxazole of Example 80 and according to a similar method, the title compound (15 mg, 38%) was obtained.

NMR (400 MHz, DMSO)δ:1.36(6H, s), 1.42(6H, s), 6.97 (1H, s), 7.40(1H, s), 7.57(1H, dd, J=6.7, 4.9 Hz), 7.94-8.00 (2H, m), 8.22-8.25(2H, m).MS:400(M$^+$+1).

Example 83

2,2-difluoro-6,6,8,8-tetramethyl-4-(quinolin-5-yl)-6,7,8,9-tetrahydro-[1,3]dioxolo[4,5-h]quinolin-7-one Using 5-bromoquinoline instead of 4-iodo-3,5-dimethylisoxazole of Example 80 and according to a similar method, the title compound (6.2 mg, 15%) was obtained.

NMR (400 MHz, DMSO)δ:1.35(6H, s), 1.42(6H, s), 6.62 (1H, s), 7.15(1H, s), 7.68(1H, dd, J=8.5, 4.0 Hz), 7.74(1H, d, J=6.9 Hz), 7.94(1H, dd, J=8.5, 6.9 Hz), 8.15(1H, d, J=8.5 Hz), 8.34(1H, d, J=8.5 Hz), 9.05(1H, dd, J=4.0, 1.2 Hz).MS:411 (M$^+$+1).

Example 84

1) 7-methoxy-2,2,4-trimethyl-1,2-dihydroquinoline

To a solution of m-anisidine (400 g) in acetone (7.2 l) were added catechol (33 g) and iodine (27 g), and the mixture was heated under reflux for 4 days. The reaction mixture filtered through silica gel and the solvent was evaporated under reduced pressure. The residue was subjected to normal phase chromatography (elution solvent hexane-ethyl acetate=10:1→5:1) to give the title compound (234 g, 35%).

NMR (400 MHz, CDCl$_3$)δ:1.26(6H, s), 1.96(3H, d, J=1.4 Hz), 3.75(3H, s), 3.75(1H, br), 5.19(1H, d, J=1.4 Hz), 6.01 (1H, d, J=2.5 Hz), 6.20(1H, dd, J=8.4, 2.5 Hz), 6.82(1H, d, J=8.4 Hz).

2) 7-methoxy-2,2,4-trimethyl-1,2,3,4-tetrahydro-quinolin-3-ol

Using the compound of the previous step (213 g) instead of 2,2,4-trimethyl-2,7,8,9-tetrahydro-1H-cyclopenta[h]quinoline of Example 1, 2) and according to a similar method, the title compound (161 g, 69%) was obtained.

NMR (400 MHz, CDCl$_3$)δ:1.09(3H, s), 1.27(3H, s), 1.39 (3H, d, J=6.6 Hz), 2.61-2.68(1H, m), 3.30(1H, d, J=9.5 Hz), 3.73(3H, s), 3.73(1H, br), 6.03(1H, d, J=2.5 Hz), 6.29(1H, dd, J=8.5, 2.5 Hz), 7.06(1H, d, J=8.5 Hz).

3) 6-bromo-7-methoxy-2,2,4-trimethyl-1,2,3,4-tetrahydroquinolin-3-ol

Using the compound of the previous step (104 g) instead of 2,2,4-trimethyl-2,3,4,7,8,9-hexahydro-1H-cyclopenta[h]quinolin-3-ol of Example 1, 3) and according to a similar method, the title compound (137 g, 97%) was obtained.

NMR (400 MHz, CDCl$_3$)δ:1.06(3H, s), 1.27(3H, s), 1.40 (3H, d, J=6.9 Hz), 1.77(1H, d, J=5.9 Hz), 2.65-2.69(1H, m), 3.30(1H, dd, J=9.2, 5.9 Hz), 3.44(3H, s), 3.70(1H, br), 6.59 (1H, s), 7.27(1H, s).

4) 6-bromo-3-(tert-butyldimethylsilyloxy)-7-methoxy-2,2,4-trimethyl-1,2,3,4-tetrahydroquinoline Using the compound of the previous step (18 g) instead of 6-bromo-2,2,4-trimethyl-2,3,4,7,8,9-hexahydro-1H-cyclopenta[h]quinolin-3-ol of Example 1, 4) and according to a similar method, the title compound (25 g, 100%) was obtained.

NMR (400 MHz, CDCl$_3$)δ:0.10(3H, s), 0.13 (3H, s), 0.94 (9H, s), 1.05(3H, s), 1.20(3H, s), 1.30(3H, d, J=6.8 Hz), 2.60-2.68 (1H, m), 3.32(1H, d, J=9.1 Hz), 3.64(1H, br), 3.79 (3H, s), 6.03(1H, s) 7.23(1H, s).

5) tert-butyl 6-bromo-3-hydroxy-7-methoxy-2,2,4-trimethyl-1,2,3,4-tetrahydroquinoline-1-carboxylate Using the compound of the previous step (25 g) instead of 4-bromo-7-(tert-butyldimethylsilyloxy)-6,8,8-trimethyl-6,7,8,9-tetrahydro-[1,3]dioxolo[4,5-h]quinoline of Example 68, 9) and according to a similar method, the title compound (10 g, 42%) was obtained.

NMR (400 MHz, CDCl$_3$)δ:1.36(3H, d, J=6.9 Hz), 1.39 (3H, s), 1.50(9H, s), 1.61(3H, s), 1.88(1H, d, J=6.2 Hz), 2.68-2.72(1H, m), 3.13(1H, dd, J=8.9, 6.2 Hz), 3.85(3H, s), 6.81(1H, s), 7.27(1H, s).

6) tert-butyl 6-bromo-7-methoxy-2,2,4-trimethyl-1,2,3,4-tetrahydroquinolin-3-one-1-carboxylate Using the compound of the previous step (10 g) instead of tert-butyl 6-bromo-3-hydroxy-2,2,4-trimethyl-2,3,4,7,8,9-hexahydro-1H-cyclopenta[h]quinoline-1-carboxylate of Example 1, 7) and according to a similar method, the title compound (7.3 g, 72%) was obtained.

NMR (400 MHz, CDCl$_3$)δ:1.42(3H, s), 1.43(3H, d, J=6.8 Hz), 1.53(9H, s), 1.72(3H, s), 3.76-3.79(1H, m), 3.88(3H, s), 6.86 (1H, s), 7.26(1H, s).

7) tert-butyl 6-bromo-7-methoxy-2,2,4,4-tetramethyl-1,2,3,4-tetrahydroquinolin-3-one-1-carboxylate Using the compound of the previous step (7.3 g) instead of tert-butyl 6-bromo-2,2,4-trimethyl-2,3,4,7,8,9-hexahydro-1H-cyclopenta[h]quinolin-3-one-1-carboxylate of Example 1, 8) and according to a similar method, the title compound (7.6 g, 100%) was obtained.

NMR (400 MHz, CDCl$_3$)δ:1.46(6H, s), 1.52(9H, s), 1.58 (6H, s), 3.88(3H, s), 6.80(1H, s), 7.35(1H, s).

8) 6-bromo-7-hydroxy-2,2,4,4-tetramethyl-1,2,3,4-tetrahydroquinolin-3-one

To a solution of the compound of the previous step (4.9 g) in CH$_2$Cl$_2$ (50 ml) was added dropwise 1.0M boron tribromide/CH$_2$Cl$_2$ solution (30 ml) under ice-cooling, and the mixture was stirred at room temperature for 3 hr. The reaction solution was neutralized with 1N aqueous sodium hydroxide solution, and extracted with CHCl$_3$. The organic layer was washed with water and saturated brine, and dried over sodium sulfate. The solvent was evaporated under reduced pressure. The residue was subjected to normal phase chromatography (elution solvent hexane→hexane-ethyl acetate=7:3) to give the title compound (3.2 g, 91%).

NMR (400 MHz, CDCl$_3$)δ:1.31(6H, s), 1.40(6H, s), 3.65 (1H, br), 5.38(1H, s), 6.38(1H, s), 7.20(1H, s).

9) 6-bromo-7-(2-hydroxyethoxy)-2,2,4,4-tetramethyl-1,2,3,4-tetrahydroquinolin-3-one To a solution of the compound of the previous step (2.5 g) in DMF (40 ml) were added potassium carbonate (1.4 g) and 2-bromoethanol, and the mixture was stirred at 120° C. for 3 hr. The reaction mixture was diluted with water, and the mixture was extracted with ethyl acetate. The organic layer was washed with saturated brine, and dried over sodium sulfate. The solvent was evaporated under reduced pressure. The residue was subjected to normal phase chromatography (elution solvent hexane→hexane-ethyl acetate=20:1) to give the title compound (2.9 g, 100%).

NMR (400 MHz, CDCl$_3$)δ:1.31(6H, s), 1.40(6H, s), 2.26 (1H, t, J=6.4 Hz), 3.95-3.99(2H, m), 4.09-4.11(2H, m), 4.52 (1H, s), 6.29(1H, s), 7.29(1H, s).

10) 6,8-dibromo-7-(2-hydroxyethoxy)-2,2,4,4-tetramethyl-1,2,3,4-tetrahydroquinolin-3-one To a solution of the compound of the previous step (2.3 g) in THF (30 ml) was added pyridinium hydrobromide perbromide (4.1 g) under ice-cooling, and the mixture was stirred for 1 hr. The reaction solution was neutralized with 1N aqueous sodium hydroxide solution, and extracted with ethyl acetate. The organic layer was washed with water and saturated brine, and dried over sodium sulfate. The solvent was evaporated under reduced pressure. The residue was subjected to normal phase chromatography (elution solvent hexane-hexane-ethyl acetate=3:2) to give the title compound (2.2 g, 81%).

NMR (400 MHz, CDCl$_3$)δ:1.34(6H, s), 1.43(6H, s), 2.42 (1H, t, J=6.4 Hz), 3.98-4.02(2H, m), 4.18-4.21(2H, m), 4.50 (1H, br), 7.31(1H, s).

11) 6,8-dibromo-7-(2-bromoethoxy)-2,2,4,4-tetramethyl-1,2,3,4-tetrahydroquinolin-3-one To a solution of the compound of the previous step (2.2 g) in diethyl ether (10 ml) were added triphenylphosphine (2.8 g) and carbon tetrabromide (3.5 g), and the mixture was stirred at room temperature for 1 hr. The reaction solution was diluted with 1N aqueous sodium hydroxide solution, and the mixture was extracted with ethyl acetate. The organic layer was washed with water and saturated brine, and dried over sodium sulfate. The solvent was evaporated under reduced pressure. The residue was subjected to normal phase chromatography (elution solvent hexane→hexane-ethyl acetate=4:1) to give the title compound (2.6 g, 100%).

NMR (400 MHz, CDCl$_3$)δ:1.34(6H, s), 1.42(6H, s), 3.74 (2H, t, J=6.6 Hz), 4.32(2H, t, J=6.6 Hz), 4.50(1H, br), 7.30 (1H, s).

12) 6-bromo-2,2,4,4-tetramethyl-1,2,3,4,8,9-hexahydro-furo[2,3-h]quinolin-3-one

A solution of the compound of the previous step (2.8 g) in THF (60 ml) was cooled to −78° C., 1.6M n-butyllithium-hexane solution (7.0 ml) was added dropwise, and the mixture was stirred for 1 hr. The reaction solution was diluted with water, and the mixture was extracted with ethyl acetate. The organic layer was washed with saturated brine, and dried over sodium sulfate. The solvent was evaporated under reduced pressure. The residue was subjected to normal phase chromatography (elution solvent hexane→hexane-ethyl acetate=7:3) to give the title compound (590 mg, 32%).

NMR (400 MHz, CDCl$_3$)δ:1.33(6H, s), 1.41(6H, s), 3.14 (2H, t, J=8.6 Hz), 3.39(1H, br), 4.73(2H, t, J=8.6 Hz), 7.08 (1H, s).

13) 2,2,4,4-tetramethyl-6-(4,4,5,5-tetramethyl-[1,3,2]dioxaborolan-2-yl)-1,2,3,4,8,9-hexahydro-furo[2,3-h]quinolin-3-one Using the compound of the previous step (300 mg) instead of tert-butyl 6-bromo-2,2,4,4-tetramethyl-2,3,4,7,8,9-hexahydro-1H-cyclopenta[h]quinolin-3-one-1-carboxylate of Example 1, 9) and according to a similar method, the title compound (343 mg, 100%) was obtained.

NMR (400 MHz, CDCl$_3$)δ:1.24(6H, s), 1.33(12H, s), 1.45 (6H, s), 2.98(2H, t, J=8.7 Hz), 3.55(1H, br), 4.71(2H, t, J=8.7 Hz), 7.38(1H, s).

14) 6-(3,5-dimethylisoxazol-4-yl)-2,2,4,4-tetramethyl-1,2,3,4,8,9-hexahydro-furo[2,3-h]quinolin-3-one To a solution of the compound of the previous step (30 mg) in DMF (1.5 ml) were added 4-iodo-3,5-dimethylisoxazole (18 mg), 2.0M aqueous potassium carbonate solution (120 µl) and tetrakis(triphenylphosphine)palladium(0) (2.8 mg), and the mixture was stirred at 130° C. for 2 hr. The reaction solution was diluted with water and ethyl acetate, and the mixture was filtered through a sellite column. The solvent was evaporated and the residue was subjected to high performance liquid chromatography to give the title compound (17 mg, 60%).

NMR (400 MHz, DMSO)δ:1.27(6H, s), 1.33(6H, s), 2.13 (3H, s), 2.28(3H, s), 3.11(2H, t, J=8.7 Hz), 4.57(2H, t, J=8.7 Hz), 5.56(1H, s), 6.81(1H, s).MS:341(M$^+$+1).

Example 85

6-(3-hydroxymethyl-5-methylisoxazol-4-yl)-2,2,4,4-tetramethyl-1,2,3,4,8,9-hexahydro-furo[2,3-h]quinolin-3-one Using (4-bromo-5-methylisoxazol-3-yl)methanol instead of 4-iodo-3,5-dimethylisoxazole of Example 84, 14) and according to a similar method, the title compound (6.7 mg, 23%) was obtained.

NMR (400 MHz, DMSO)δ:1.27(6H, s), 1.33(6H, s), 2.31 (3H, s), 3.10(2H, t, J=8.6 Hz), 4.41(2H, d, J=5.6 Hz), 4.57 (2H, t, J=8.6 Hz), 5.25(1H, t, J=5.6 Hz), 5.54(1H, s), 7.03 (1H, s).MS:357(M$^+$+1).

Example 86

6-(3-amino-5-methylisoxazol-4-yl)-2,2,4,4-tetramethyl-1,2,3,4,8,9-hexahydro-furo[2,3-h]quinolin-3-one Using 3-amino-4-bromo-5-methylisoxazole instead of 4-iodo-3,5-dimethylisoxazole of Example 84, 14) and according to a similar method, the title compound (0.9 mg, 3%) was obtained.

NMR (400 MHz, DMSO)δ:1.26(6H, s), 1.33(6H, s), 2.19 (3H, s), 3.10(2H, t, J=8.6 Hz), 4.59(2H, t, J=8.6 Hz), 5.07 (2H, br), 5.52(1H, s), 6.81(1H, s).MS:342(M$^+$+1).

Example 87

6-(2-cyano-3-methylthiophen-4-yl)-2,2,4,4-tetramethyl-1,2,3,4,8,9-hexahydro-furo[2,3-h]quinolin-3-one Using 4-bromo-3-methylthiophene-2-carbonitrile instead of 4-iodo-3,5-dimethylisoxazole of Example 84, 14) and according to a similar method, the title compound (9.7 mg, 33%) was obtained.

NMR (400 MHz, DMSO)δ:1.27(6H, s), 1.33(6H, s), 2.30 (3H, s), 3.11(2H, t, J=8.6 Hz), 4.57(2H, t, J=8.6 Hz), 5.60 (1H, br), 6.87(1H, s), 7.80(1H, s).MS:367(M$^+$+1).

Example 88

6-(imidazo[1,2-a]pyridin-5-yl)-2,2,4,4-tetramethyl-1,2,3,4,8,9-hexahydro-furo[2,3-h]quinolin-3-one Using 5-bromoimidazo[1,2-a]pyridine instead of 4-iodo-3,5-dimethylisoxazole of Example 84, 14) and according to a similar method, the title compound (21 mg, 73%) was obtained.

NMR (400 MHz, DMSO)δ:1.33(6H, s), 1.38(6H, s), 3.18 (2H, t, J=8.6 Hz), 4.67(2H, t, J=8.6 Hz), 6.08(1H, br), 7.20 (1H, s), 7.49(1H, d, J=6.9 Hz), 7.91(1H, d, J=8.8 Hz), 7.97-8.01(2H, m), 8.17(1H, d, J=2.1 Hz).MS:362(M$^+$+1).

Example 89

2,2,4,4-tetramethyl-6-([1,2,4]triazolo[4,3-a]pyridin-5-yl)-1,2,3,4,8,9-hexahydro-furo[2,3-h]quinolin-3-one Using 5-chloro[1,2,4]triazolo[4,3-a]pyridine instead of 4-iodo-3,5-dimethylisoxazole of Example 84, 14) and according to a similar method, the title compound (10 mg, 35%) was obtained.

NMR (400 MHz, DMSO)δ:1.32(6H, s), 1.38(6H, s), 3.17 (2H, t, J=8.6 Hz), 4.69(2H, t, J=8.6 Hz), 6.03(1H, br), 7.18-7.20(2H, m), 7.71(1H, dd, J=9.0, 7.1 Hz), 7.86(1H, d, J=9.0 Hz), 9.20(1H, s).MS:363(M$^+$+1).

Example 90

6-(imidazo[1,2-a]pyrazin-5-yl)-2,2,4,4-tetramethyl-1,2,3,4,8,9-hexahydro-furo[2,3-h]quinolin-3-one Using 5-chloroimidazo[1,2-a]pyrazine instead of 4-iodo-3,5-dimethylisoxazole of Example 84, 14) and according to a similar method, the title compound (20 mg, 69%) was obtained.
NMR (400 MHz, DMSO)δ:1.32(6H, s), 1.38(6H, s), 3.18 (2H, t, J=8.6 Hz), 4.67(2H, t, J=8.6 Hz), 6.02(1H, br), 7.22 (1H, s), 7.99(1H, s), 8.05(1H, d, J=1.1 Hz), 8.10(1H, s), 9.17(1H, s).MS:363($M^+$+1).

Example 91

2,2,4,4-tetramethyl-6-(quinolin-5-yl)-1,2,3,4,8,9-hexahydro-furo[2,3-h]quinolin-3-one Using 5-bromoquinoline instead of 4-iodo-3,5-dimethylisoxazole of Example 84, 14) and according to a similar method, the title compound (20 mg, 66%) was obtained.
NMR (400 MHz, DMSO)δ:1.32(6H, s), 1.37(6H, s), 3.17 (2H, t, J=8.6 Hz), 4.53(2H, t, J=8.6 Hz), 5.71(1H, br), 6.98 (1H, s), 7.66(1H, d, J=7.5 Hz), 7.73(1H, dd, J=8.6, 4.6 Hz), 7.94(1H, dd, J=8.4, 7.5 Hz), 8.08(1H, d, J=8.4 Hz), 8.43(1H, d, J=8.6 Hz), 9.08(1H, dd, J=4.6, 1.4 Hz).MS:373($M^+$+1).

Example 92

2,2,4,4-tetramethyl-6-([1,8]naphthyridin-4-yl)-1,2,3,4,8,9-hexahydro-furo[2,3-h]quinolin-3-one Using 4-chloro[1,8]naphthyridine instead of 4-iodo-3,5-dimethylisoxazole of Example 84, 14) and according to a similar method, the title compound (23 mg, 47%) was obtained.
NMR (400 MHz, DMSO)δ:1.33(6H, s), 1.38(6H, s), 3.18 (2H, t, J=8.7 Hz), 4.61(2H, t, J=8.7 Hz), 6.02(1H, br), 7.11 (1H, s), 7.76(1H, dd, J=8.5, 4.3 Hz), 7.78(1H, d, J=5.0 Hz), 8.49(1H, dd, J=8.5, 1.6 Hz), 9.14(1H, d, J=5.0 Hz), 9.17(1H, dd, J=4.3, 1.6 Hz).MS:374($M^+$+1).

Example 93

1) 6-bromo-2,2,4,4-tetramethyl-1,2,3,4-tetrahydro-furo[2,3-h]quinolin-3-one

To a solution of 6-bromo-2,2,4,4-tetramethyl-1,2,3,4,8,9-hexahydro-furo[2,3-h]quinolin-3-one (426 mg) obtained in Example 84, 12) in dioxane (13 ml) was added 2,3-dichloro-5,6-dicyano-1,4-benzoquinone (447 mg), and the mixture was heated under reflux for 2 hr. The precipitate was filtered off, and the solvent was evaporated under reduced pressure. The residue was subjected to normal phase chromatography (elution solvent hexane→hexane-ethyl acetate=7:3) to give the title compound (125 mg, 30%).
NMR (400 MHz, CDCl$_3$)δ:1.37(6H, s), 1.46(6H, s), 3.88 (1H, br), 6.77(1H, d, J=2.2 Hz), 7.28(1H, s), 7.63(1H, d, J=2.2 Hz).

2) 2,2,4,4-tetramethyl-6-(4,4,5,5-tetramethyl-[1,3,2] dioxaborolan-2-yl)-1,2,3,4-tetrahydro-furo[2,3-h]quinolin-3-one Using the compound of the previous step (125 mg) instead of tert-butyl 6-bromo-2,2,4,4-tetramethyl-2,3,4,7,8,9-hexahydro-1H-cyclopenta[h]quinolin-3-one-1-carboxylate of Example 1, 9) and according to a similar method, the title compound (143 mg, 100%) was obtained.
NMR (400 MHz, CDCl$_3$)δ:1.26(6H, s), 1.39(12H, s), 1.51 (6H, s), 4.05(1H, br), 6.68(1H, d, J=2.3 Hz), 7.61(1H, s), 7.67(1H, d, J=2.3 Hz).

3) 6-(3,5-dimethylisoxazol-4-yl)-2,2,4,4-tetramethyl-1,2,3,4-tetrahydro-furo[2,3-h]quinolin-3-one Using the compound of the previous step instead of 2,2,4,4-tetramethyl-6-(4,4,5,5-tetramethyl-[1,3,2]dioxaborolan-2-yl)-1,2,3,4,8,9-hexahydro-furo[2,3-h]quinolin-3-one of Example 84, 14) and according to a similar method, the title compound (43 mg, 32%) was obtained.
NMR (400 MHz, DMSO)δ:1.31(6H, s), 1.40(6H, s), 2.18 (3H, s), 2.35(3H, s), 6.30(1H, s), 7.07(1H, s), 7.28(1H, d, J=2.3 Hz), 7.85(1H, d, J=2.3 Hz).MS:339($M^+$+1).

Example 94

6-(3-hydroxymethyl-5-methylisoxazol-4-yl)-2,2,4,4-tetramethyl-1,2,3,4-tetrahydro-furo[2,3-h]quinolin-3-one Using (4-bromo-5-methylisoxazol-3-yl)methanol instead of 4-iodo-3,5-dimethylisoxazole of Example 93, 3) and according to a similar method, the title compound (1.2 mg, 12%) was obtained.
NMR (400 MHz, DMSO)δ:1.31(6H, s), 1.40(6H, s), 2.37 (3H, s), 4.47(2H, d, J=5.4 Hz), 5.32(1H, t, J=5.4 Hz), 6.27 (1H, s), 7.27(1H, d, J=2.2 Hz), 7.28(1H, s), 7.84(1H, d, J=2.2 Hz).MS:355($M^+$+1)

Example 95

6-(3-amino-5-methylisoxazol-4-yl)-2,2,4,4-tetramethyl-1,2,3,4-tetrahydro-furo[2,3-h]quinolin-3-one Using 3-amino-4-bromo-5-methylisoxazole instead of 4-iodo-3,5-dimethylisoxazole of Example 93, 3) and according to a similar method, the title compound (1.0 mg, 11%) was obtained.
NMR (400 MHz, DMSO)δ:1.30(6H, s), 1.40(6H, s), 2.21 (3H, s), 5.20(2H, br), 6.23(1H, s), 7.04(1H, s), 7.26(1H, d, J=2.2 Hz), 7.84(1H, d, J=2.2 Hz).MS:340($M^+$+1).

Example 96

2,2,4,4-tetramethyl-6-(2-cyano-3-methylthiophen-4-yl)-1,2,3,4-tetrahydro-furo[2,3-h]quinolin-3-one Using 4-bromo-3-methylthiophene-2-carbonitrile instead of 4-iodo-3,5-dimethylisoxazole of Example 93U3) and according to a similar method, the title compound (1.4 mg, 14%) was obtained.
NMR (400 MHz, DMSO)δ:1.31(6H, s), 1.40(6H, s), 2.34 (3H, s), 6.35(1H, s), 7.13(1H, s), 7.29(1H, d, J=2.2 Hz), 7.86(1H, d, J=2.2 Hz), 8.03(1H, s).MS:365($M^+$+1).

Example 97

6-(3,5-dimethyl-3H-[1,2,3]triazol-4-yl)-2,2,4,4-tetramethyl-1,2,3,4-tetrahydro-furo[2,3-h]quinolin-3-one Using 4-bromo-3,5-dimethyl-3H-[1,2,3]triazole instead of 4-iodo-3,5-dimethylisoxazole of Example 93, 3) and according to a similar method, the title compound (0.5 mg, 5%) was obtained.

NMR (400 MHz, DMSO)δ: 1.33(6H, s), 1.41(6H, s), 2.18 (3H, s), 3.88(3H, s), 6.50(1H, s), 7.19(1H, s), 7.32(1H, d, J=2.1 Hz), 7.88(1H, d, J=2.1 Hz).MS:339(M⁺+1).

Example 98

6-(imidazo[1,2-a]pyridin-5-yl)-2,2,4,4-tetramethyl-1, 2,3,4-tetrahydro-furo[2,3-h]quinolin-3-one Using 5-bromoimidazo[1,2-a]pyridine instead of 4-iodo-3,5-dimethylisoxazole of Example 93, 3) and according to a similar method, the title compound (1.5 mg, 15%) was obtained.

NMR (400 MHz, DMSO)δ:1.37(6H, s), 1.44(6H, s), 6.80 (1H, s), 7.39(1H, d, J=2.1 Hz), 7.50(1H, s), 7.61(1H, d, J=6.7 Hz), 7.94-8.01(3H, m), 8.16(1H, d, J=1.6 Hz).MS:360(M⁺+1).

Example 99

2,2,4,4-tetramethyl-6-([1,2,4]triazolo[4,3-a]pyridin-5-yl)-1,2,3,4-tetrahydro-furo[2,3-h]quinolin-3-one Using 2,2,4,4-tetramethyl-6-([1,2,4]triazolo[4,3-a]pyridin-5-yl)-1,2,3,4,8,9-hexahydro-furo[2,3-h]quinolin-3-one obtained in Example 89 instead of 6-bromo-2,2,4,4-tetramethyl-1,2,3,4,8,9-hexahydro-furo[2,3-h]quinolin-3-one of Example 93, 1) and according to a similar method, the title compound (1.5 mg, 24%) was obtained.

NMR (400 MHz, DMSO)δ:1.36(6H, s), 1.44(6H, s), 6.68 (1H, s), 7.12(1H, d, J=6.8 Hz), 7.36(1H, d, J=2.2 Hz), 7.48-7.52(2H, m), 7.81(1H, d, J=9.2 Hz), 7.90(1H, d, J=2.2 Hz), 8.95 (1H, s).MS:361(M⁺1).

Example 100

6-(imidazo[1,2-a]pyrazin-5-yl)-2,2,4,4-tetramethyl-1,2,3,4-tetrahydro-furo[2,3-h]quinolin-3-one Using 5-chloroimidazo[1,2-a]pyrazine instead of 4-iodo-3,5-dimethylisoxazole of Example 93, 3) and according to a similar method, the title compound (3.1 mg, 32%) was obtained.

NMR (400 MHz, DMSO)δ:1.36(6H, s), 1.45(6H, s), 6.72 (1H, br), 7.38(1H, d, J=2.0 Hz), 7.51(1H, s), 7.86(1H, s), 7.91(1H, d, J=2.0 Hz), 7.94(1H, s), 8.14(1H, s), 9.16(1H, s).MS:361(M⁺+1).

Example 101

2,2,4,4-tetramethyl-6-(quinolin-5-yl)-1,2,3,4-tetrahydro-furo [2,3-h]quinolin-3-one Using 5-bromoquinoline instead of 4-iodo-3,5-dimethylisoxazole of Example 93, 3) and according to a similar method, the title compound (5.1 mg, 51%) was obtained.

NMR (400 MHz, DMSO)δ: 1.36(6H, s), 1.44(6H, s), 5.71 (1H, br), 6.42(1H, br), 7.21(1H, s), 7.34(1H, d, J=2.2 Hz), 7.67(1H, dd, J=8.5, 4.4 Hz), 7.79(1H, d, J=2.2 Hz), 7.80(1H, d, J=7.2 Hz), 7.98(1H, dd, J=8.4, 7.2 Hz), 8.15(1H, d, J=8.4 Hz), 8.27(1H, d, J=8.5 Hz), 9.07(1H, dd, J=4.4, 1.4 Hz).MS: 371(M⁺+1).

Example 102

2,2,4,4-tetramethyl-6-([1,8]naphthyridin-4-yl)-1,2,3,4-tetrahydro-furo[2,3-h]quinolin-3-one Using 2,2,4,4-tetramethyl-6-([1,8]naphthyridin-4-yl)-1,2,3,4,8,9-hexahydro-furo[2,3-h]quinolin-3-one obtained in Example 92 instead of 6-bromo-2,2,4,4-tetramethyl-1,2,3,4,8,9-hexahydro-furo[2,3-h]quinolin-3-one of Example 93, 1) and according to a similar method, the title compound (2.2 mg, 22%) was obtained.

NMR (400 MHz, DMSO)δ:1.36(6H, s), 1.44(6H, s), 6.55 (1H, s), 7.29(1H, s), 7.35(1H, d, J=2.0 Hz), 7.60(1H, dd, J=8.4, 4.1 Hz), 7.73(1H, d, J=4.4 Hz), 7.83(1H, d, J=2.0 Hz), 8.21 (1H, d, J=8.4 Hz), 9.10-9.11(1H, m), 9.13(1H, d, J=4.4 Hz).MS:372(M⁺+1).

Example 103

8-bromo-6-(3,5-dimethylisoxazol-4-yl)-2,2,4,4-tetramethyl-1,2,3,4-tetrahydro-furo[2,3-h]quinolin-3-one

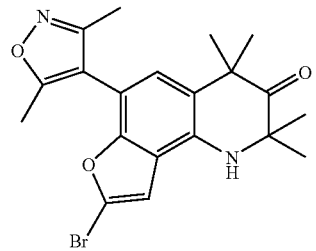 [SMILES: Cc1noc(C)c1-c1cc2c(c3cc(Br)oc13)NC(C)(C)C(=O)C2(C)C]

To a solution of 6-(3,5-dimethylisoxazol-4-yl)-2,2,4,4-tetramethyl-1,2,3,4-tetrahydro-furo[2,3-h]quinolin-3-one (31 mg) obtained in Example 93, 3) in THF (1.0 ml) was added pyridinium hydrobromide perbromide (29 mg) under ice-cooling, and the mixture was stirred at room temperature for 1 hr. The reaction solution was neutralized with 1N aqueous sodium hydroxide solution, and extracted with ethyl acetate. The organic layer was washed with water and saturated brine, and dried over sodium sulfate. The solvent was evaporated under reduced pressure. The residue was subjected to normal phase chromatography (elution solvent hexane→hexane-ethyl acetate=3:2) to give the title compound (17 mg, 44%).

NMR (400 MHz, DMSO)δ:1.30(6H, s), 1.39(6H, s), 2.18 (3H, s), 2.35(3H, s), 6.33(1H, s), 7.08(1H, s), 7.37(1H, s).MS: 417(M⁺), 419 (M⁺+2).

Example 104

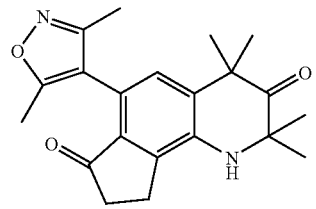 [SMILES: Cc1noc(C)c1-c1cc2c(c3c1C(=O)CC3)NC(C)(C)C(=O)C2(C)C]

1) tert-butyl 6-bromo-2,2,4,4-tetramethyl-2,3,4,7,8, 9-hexahydro-1H-cyclopenta[h]quinoline-3,7-dione-1-carboxylate To a solution of tert-butyl 6-bromo-2,2,4,4-tetramethyl-2,3,4,7,8,9-hexahydro-1H-cyclopenta[h]quinolin-3-one-1-carboxylate (2.1 g) obtained in Example 1, 8) in acetone (50 ml) was added potassium permanganate (7.9 g), and the mixture was cooled to 0° C. Iron trichloride (5.0 g) was added, and the mixture was stirred at 50° C. for 16 hr. The reaction solution was diluted with isopropanol (20 ml) and CHCl₃ (20 ml), filtered through celite, and extracted with CHCl₃. The organic layer was washed with water, saturated aqueous sodium hydrogen carbonate and saturated brine, and dried over sodium sulfate. The solvent was evaporated under reduced pressure. The residue was subjected to normal phase chromatography (elution solvent hexane-ethyl acetate=3:1) to give the title compound (681 mg, 31%, Rf=0.29 [hexane: ethyl acetate=3:1]) and tert-butyl 6-bromo-2,2,4,4-tetramethyl-2,3,7,8-hexahydro-1H-cyclopenta[h]quinoline-3,9-dione-1-carboxylate (293 mg, 13%, Rf=0.33 [hexane:ethyl acetate=3:1]).

NMR (400 MHz, CDCl₃)δ:1.49(9H, s), 1.52(6H, s), 2.76 (2H, br), 3.00(2H, br), 7.45(1H, s).

2) 6-(3,5-dimethylisoxazol-4-yl)-2,2,4,4-tetramethyl-2,3,4,7,8,9-hexahydro-1H-cyclopenta[h]quinoline-3,7-dione To a solution of the compound of the previous step (581 mg) in isopropanol (4 ml) were added 3,5-dimethyl-4-(4,4,5,5-tetramethyl-[1,3,2]dioxaborolan-2-yl)isoxazole (357 mg), 2.0 M aqueous potassium carbonate solution (2.0 ml) and tetrakis(triphenylphosphine)palladium(0) (77 mg), and the mixture was stirred at 80° C. for 8 hr. The reaction solution was diluted with water, and the mixture was extracted with ethyl acetate. The organic layer was washed with saturated brine, and dried over sodium sulfate. The solvent was evaporated under reduced pressure.

To a solution of the residue in CH₂Cl₂ (5 ml) was added trifluoroacetic acid (5 ml), and the mixture was stirred at room temperature for 30 min. The reaction solution was neutralized with 1N aqueous sodium hydroxide solution, and the mixture was extracted with CHCl₃. The organic layer was washed with water and saturated brine, and dried over sodium sulfate. The solvent was evaporated under reduced pressure. The residue was subjected to normal phase chromatography (elution solvent hexane→hexane-ethyl acetate=1:1) to give the title compound (335 mg, 71%).

NMR (400 MHz, DMSO)δ:1.32(6H, s), 1.40(6H, s), 1.99 (3H, s), 2.18(3H, s), 2.64-2.67(2H, m), 2.93-2.96(2H, m), 5.87(1H, br), 7.06(1H, s).MS:353(M⁺+1).

The structures of the Example compounds are shown in Table 1-Table 9.

TABLE 1

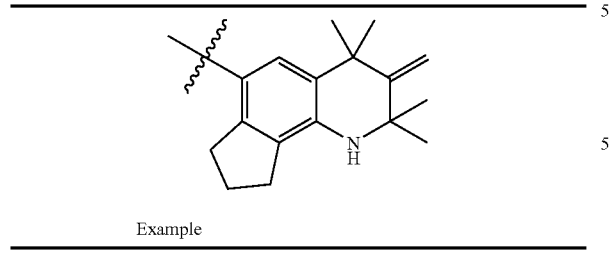

| Example | |
|---|---|
| 30 | 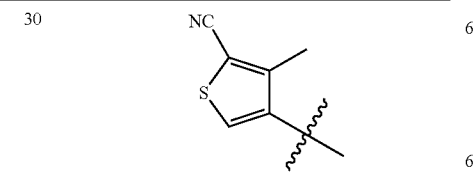 |
| 31 | 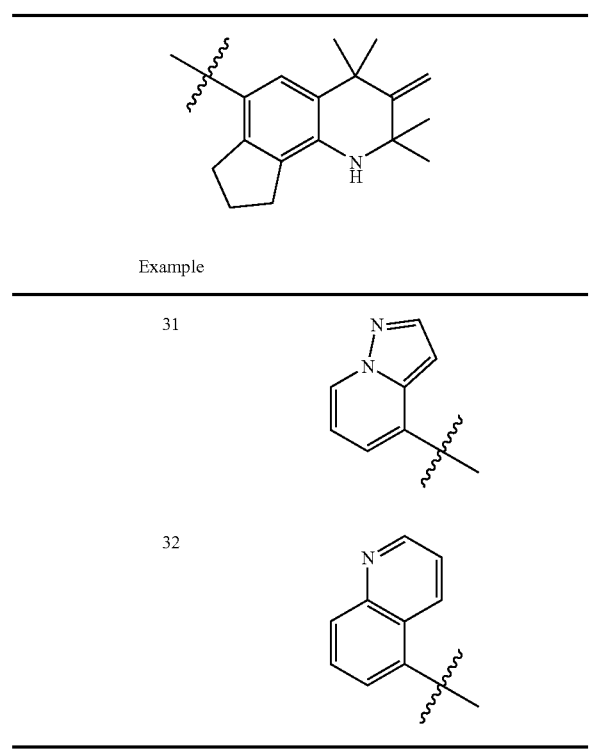 (top structure) |
| 32 | 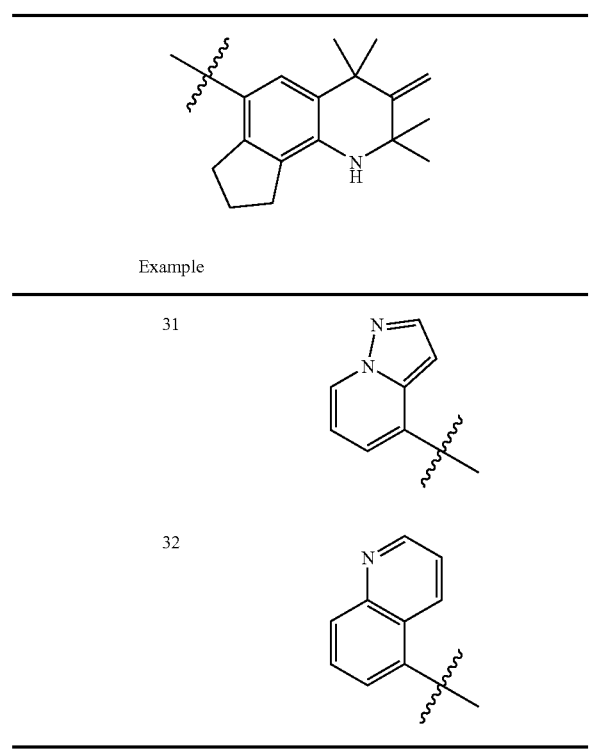 (bottom structure) |

TABLE 2

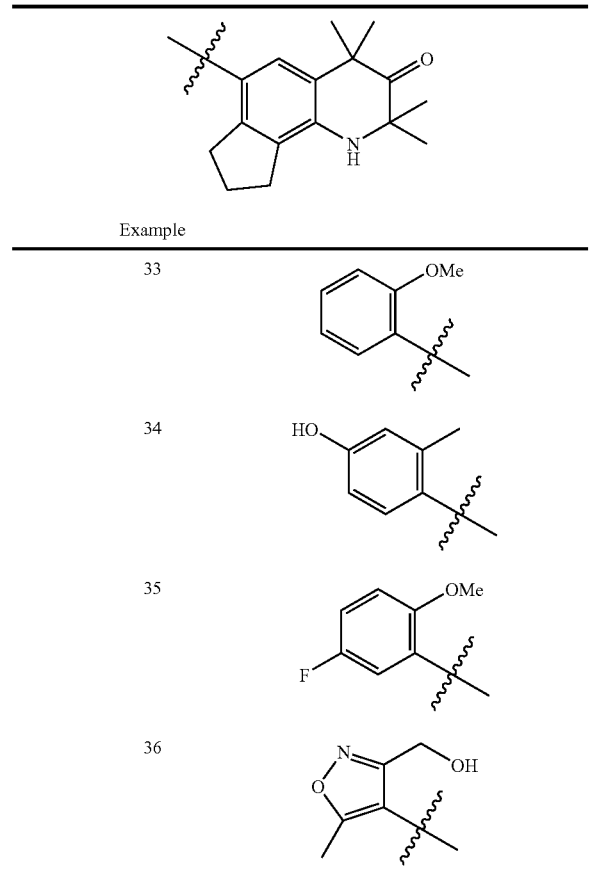

| Example | |
|---|---|
| 33 | 2-OMe phenyl |
| 34 | HO-phenyl-methyl |
| 35 | 4-F, 2-OMe phenyl |
| 36 | 5-methylisoxazol-4-yl-CH₂OH |

TABLE 2-continued
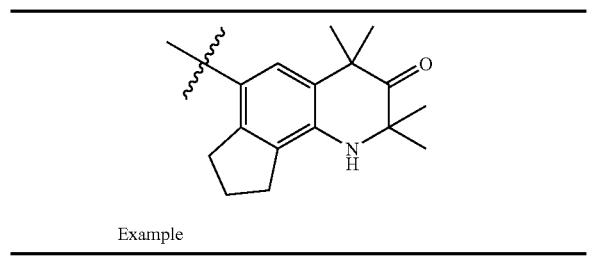
| Example | |
|---|---|
| 37 | 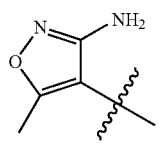 [SMILES: *c1c(N)noc1C] |
| 38A | 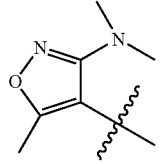 [SMILES: *c1c(N(C)C)noc1C] |
| 38B | 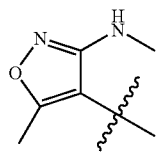 [SMILES: *c1c(NC)noc1C] |
| 39 | 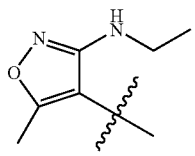 [SMILES: *c1c(NCC)noc1C] |
| 40A | 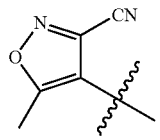 [SMILES: *c1c(C#N)noc1C] |
| 40B | 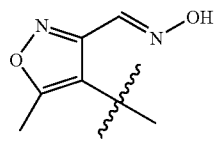 [SMILES: *c1c(/C=N/O)noc1C] |
| 41 | 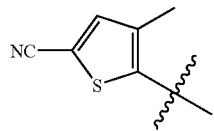 |
| 42 | 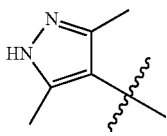 |
| 43 | 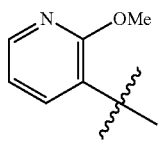 [SMILES: *c1cccnc1OC] |
TABLE 2-continued
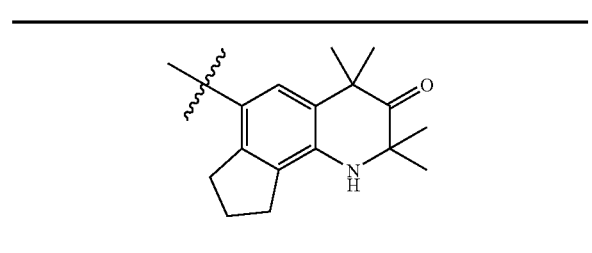
| Example | |
|---|---|
| 44 | 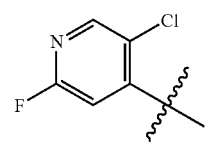 |
| 45 | 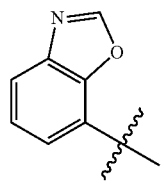 [SMILES: *c1cccc2ncoc12] |
| 46 | 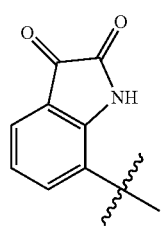 [SMILES: *c1cccc2c1NC(=O)C2=O] |
| 47 | 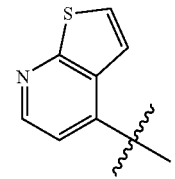 [SMILES: *c1ccnc2sccc12] |
| 48 | 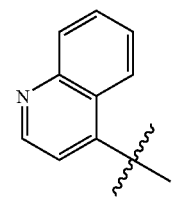 [SMILES: *c1ccnc2ccccc12] |
| 49 | 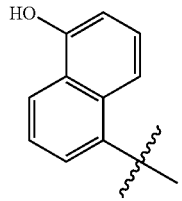 |

TABLE 3
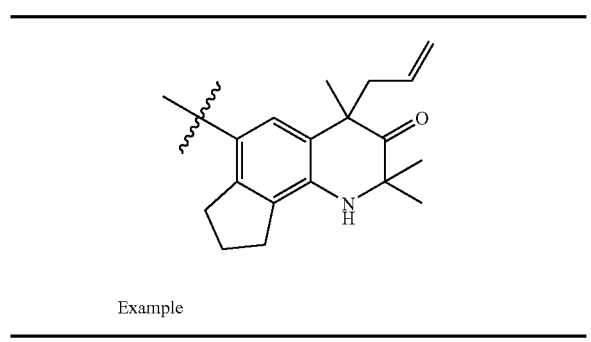
| Example | |
|---|---|
| 50 | 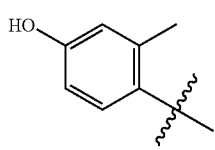 [SMILES: *c1ccc(O)cc1C] |
| 51 | 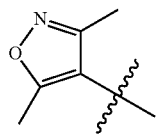 [SMILES: *c1c(C)noc1C] |
| 52 | 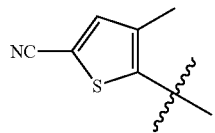 |
| 53 | 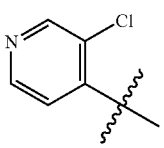 [SMILES: *c1ccncc1Cl] |
| 54 | 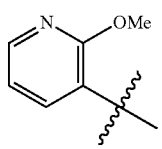 [SMILES: *c1cccnc1OC] |
| 55 | 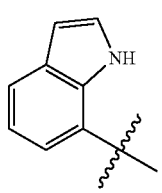 |
| 56 | 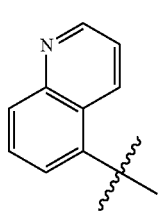 [SMILES: *c1cccc2ncccc12] |
TABLE 4
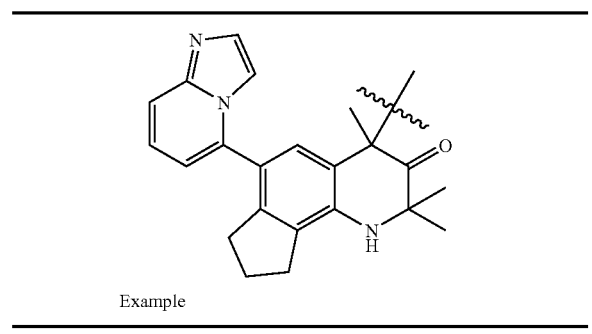
| Example | |
|---|---|
| 57 |  |
| 58 | 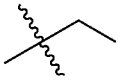 [SMILES: *CC] |
| 59 | 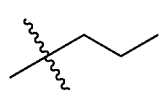 [SMILES: *CCC] |
| 60 | 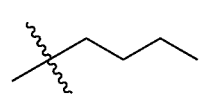 [SMILES: *CCCC] |
| 61 | 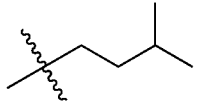 [SMILES: *CCC(C)C] |
| 62 | 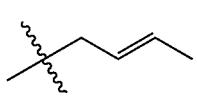 [SMILES: *C/C=C/C] |
| 63 | 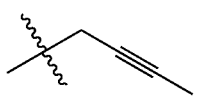 |
| 64 | 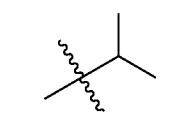 [SMILES: *C(C)C] |
| 65 | 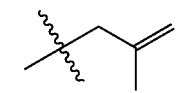 [SMILES: *CC(=C)C] |
| 66 | 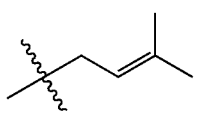 [SMILES: *CC=C(C)C] |
| 67 | 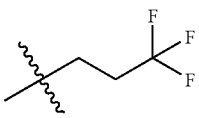 [SMILES: *CCC(F)(F)F] |

TABLE 5
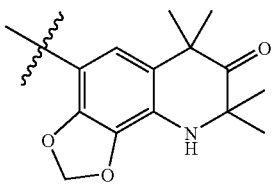 [SMILES: *c1cc2c(c3c1OCO3)NC(C)(C)C(=O)C2(C)C]
| Example | |
|---|---|
| 68 | 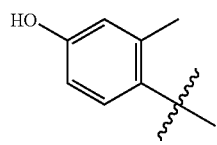 [SMILES: *c1ccc(O)cc1C] |
| 69 | 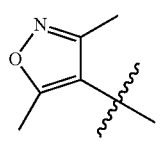 [SMILES: *c1c(C)noc1C] |
| 70 | 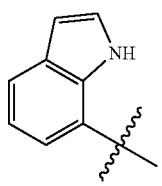 [SMILES: *c1cccc2cc[nH]c12] |
| 71 | 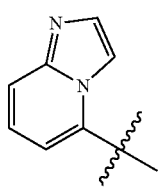 [SMILES: *c1cccc2nccn12] |
| 72 | 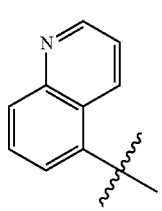 [SMILES: *c1cccc2ncccc12] |
| 73 | 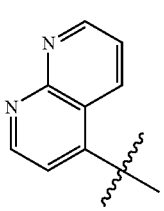 [SMILES: *c1ccnc2ncccc12] |
TABLE 6
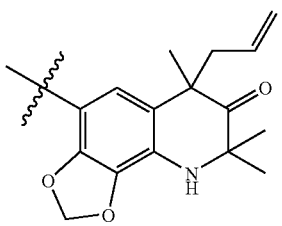 [SMILES: *c1cc2c(c3c1OCO3)NC(C)(C)C(=O)C2(C)CC=C]
| Example | |
|---|---|
| 74 | 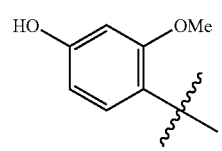 [SMILES: *c1ccc(O)cc1OC] |
| 75 | 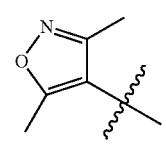 |
| 76 | 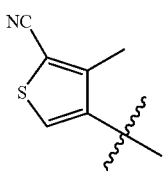 |
| 77 | 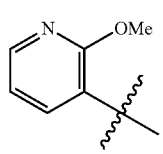 [SMILES: *c1cccnc1OC] |
| 78 | 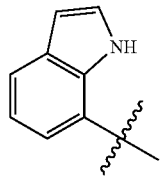 [SMILES: *c1cccc2cc[nH]c12] |
| 79 | 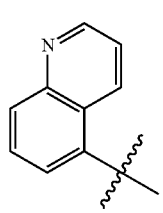 [SMILES: *c1cccc2ncccc12] |

TABLE 7
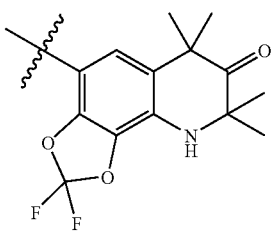 [SMILES: *c1cc2c(c3c1OC(F)(F)O3)NC(C)(C)C(=O)C2(C)C]
| Example | |
|---|---|
| 80 | 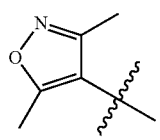 [SMILES: *c1c(C)noc1C] |
| 81 | 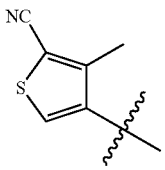 |
| 82 | 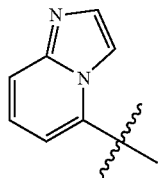 [SMILES: *c1cccc2nccn12] |
| 83 | 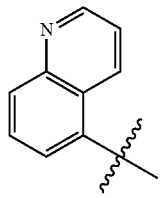 [SMILES: *c1cccc2ncccc12] |
TABLE 8
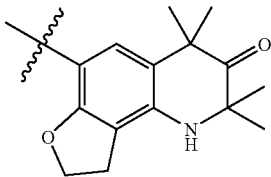 [SMILES: *c1cc2c(c3c1OCC3)NC(C)(C)C(=O)C2(C)C]
| Example | |
|---|---|
| 84 | 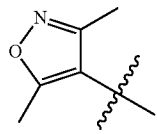 [SMILES: *c1c(C)noc1C] |
| 85 | 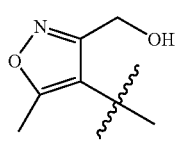 [SMILES: *c1c(CO)noc1C] |
TABLE 8-continued
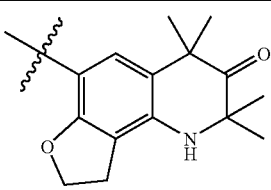
| Example | |
|---|---|
| 86 | 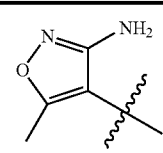 |
| 87 | 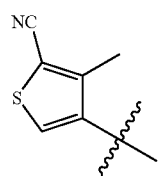 |
| 88 | 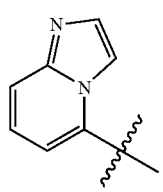 [SMILES: *c1cccc2nccn12] |
| 89 | 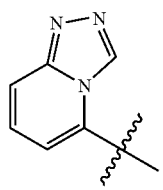 [SMILES: *c1cccc2nncn12] |
| 90 | 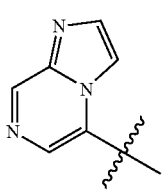 [SMILES: *c1cncc2nccn12] |
| 91 | 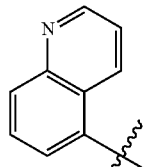 |
| 92 | 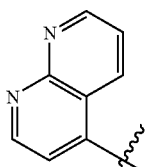 |

TABLE 9

| Example | (substituent) |
|---|---|
| 93 | 3,5-dimethylisoxazol-4-yl |
| 94 | (5-methylisoxazol-3-yl)methanol (hydroxymethyl) |
| 95 | 3-amino-5-methylisoxazol-4-yl |
| 96 | 2-cyano-3-methylthiophen-4-yl |
| 97 | 1,4-dimethyl-1,2,3-triazol-5-yl |
| 98 | imidazo[1,2-a]pyridin-5-yl |
| 99 | [1,2,4]triazolo[4,3-a]pyridin-5-yl |
| 100 | imidazo[1,2-a]pyrazin-5-yl |

TABLE 9-continued

| Example | (substituent) |
|---|---|
| 101 | quinolin-5-yl |
| 102 | 1,5-naphthyridin-4-yl |

The binding affinity and IC$_{50}$ of the compounds of Examples 4, 50, 51, 57, 58, 63, 69, 71, 72, 78, 82, 84, 88, 92, 94, 98, 100, 101, 102 and 104 are shown in Table 10.

TABLE 10

|  | GR (Ki: nM) | PR (Ki: nM) | MR (Ki: nM) | GR (IC$_{50}$: nM) |
|---|---|---|---|---|
| Example 4 | 53 | >1250 | N.T. | 86 |
| Example 50 | 97 | >1250 | >1000 | 61 |
| Example 51 | 17 | >1250 | >1000 | 33 |
| Example 57 | 14 | >1250 | >1000 | 69 |
| Example 58 | 12 | 1006 | >1000 | 37 |
| Example 63 | 27 | >1250 | >1000 | 48 |
| Example 69 | 55 | >1250 | >1000 | 77 |
| Example 71 | 59 | >1250 | >1000 | 59 |
| Example 72 | 96 | >1250 | >1000 | 40 |
| Example 78 | 80 | >1250 | >1000 | 94 |
| Example 82 | 47 | >1250 | >1000 | 111 |
| Example 84 | 27 | >1250 | N.T. | 49 |
| Example 88 | 19 | >1250 | N.T. | 66 |
| Example 92 | 64 | >1250 | N.T. | 73 |
| Example 94 | 11 | >1250 | N.T. | 66 |
| Example 98 | 15 | 1055 | N.T. | 31 |
| Example 100 | 85 | >1250 | N.T. | 47 |
| Example 101 | 35 | 1219 | N.T. | 37 |
| Example 102 | 66 | >1250 | N.T. | 35 |
| Example 104 | 60 | >1250 | N.T. | 128 |

Experimental Example 1

Radioactive Ligand Binding Test Using Cytosols of Human Glucocorticoids Receptor, Progesterone Receptor and Mineralocorticoid Receptor The procedures described in Neuroimmunomodulation (1994, 1, p. 66-73) and Invest. Opthalmol. Vis. Sci. (1996, 37, p. 805-813) were modified and used. In brief, cytosol preparations of human recombinant glucocorticoids receptor (GR) and human recombinant progesterone receptor-B (PRB) were purchased from Invitrogen (Carlsbad, Calif.), and a cytosol preparation of human recombinant mineralocorticoid receptor (MR) was prepared by our company (Yokohama, JP). MR cDNA was cloned into a baculovirus expression vector and expressed in insect cell Sf9. The procedures described in J. Biol. Chem. (1991, 266, p. 18072-18081), Proc. Natl. Acad. Sci. USA (1991, 88, p. 10681-10685) and Bac-to-Bac (registered trade mark) Baculovirus Expression Systems technical manual (Invitrogen) were partly modified and used as the procedures for MR gene cloning up to preparation of recombinant receptor cytosol. [$^3$H]-Dexamethasone (Dex, specific activity 91.0 Ci/mmol) was purchased from GE Healthcare (Buckinghamshire, UK), and [$^3$H]-progesterone (Prog, specific activity 103 Ci/mmol) and [3H]-aldosterone (Ald, specific activity 87.9 Ci/mmol) were each purchased from PerkinElmer (Boston, Mass.). Polypropylene round-bottomed 96 well plate was obtained from ABgene (Epsom, UK). Dimethyl Sulfoxide (DMSO) and hydrochloric acid were obtained from Kanto Chemical (TOKYO, JP). Trizma Base (Tris), Bovine Serum Albumin (BSA) and Sodium tungstate dihydrate were obtained from Sigma Chemicals (St. Louis, Mo.). Dithiothreitol (DTT) and Dextran 70 were obtained from GE Healthcare (Buckinghamshire, UK). Glycerol was obtained from Junsei Chemical (TOKYO, JP). Norit® "SX-II" was obtained from Wako Pure Chemical Industries, Ltd. (Osaka, JP). MeltiLex™, A, Printed Filtermat A and Sample Bag were obtained from PerkinElmer (Boston, Mass.).

As a buffer for GR binding assay, 25 mM Tris-HCl (4° C., pH 7.4)/1 mM EDTA·2Na/1 mM DTT/0.1% BSA was prepared and used. As buffers for PRB and MR binding assay, 10 mM Tris-HCl (4° C., pH 7.4)/1 mM DTT/0.1% BSA/10% glycerol and 20 mM Tris-HCl (4° C., pH 7.4)/1 mM EDTA·2Na/10% glycerol/20 mM sodium tungstate were respectively prepared and used. As dextran-coated charcoal (DCC) for B/F separation, 0.75% Dextran 70/0.75% Norit® SX-II/10 mM Tris-HCl (4° C., pH 7.4) was prepared and used.

Compound storage solutions (5-20 mM) were prepared using DMSO. The storage solutions were diluted with DMSO to 0.1 mM (for GR) and 0.3 mM (for PRB and MR), and further diluted 20-fold with distilled water to give solutions. Then, the preparations were diluted to each concentration with 5% DMSO solution. 1% DMSO was present at the time of the binding assay.

GR, PRB and MR binding reactions were performed in 96 well plate (ABgene). In the case of GR binding assay, [$^3$H]-Dex (about 5 nM), GR cytosol (concentration of function receptor: about 4 pmol/mL), a test compound and a binding buffer were mixed in a total volume of 50 µL, and the mixture was stood at 4° C. for 30 min or longer. A specific binding was defined to be the difference in the [$^3$H]-Dex binding between the presence and the absence of 1 µM unlabeled Dex.

In the case of PRB binding assay, [$^3$H]-Prog (about 5 nM), PRB cytosol (concentration of function receptor: about 4 pmol/mL), a test compound and a binding buffer were mixed in a total volume of 50 µL, and the mixture was stood at 4° C. for 30 min or longer. A specific binding was defined to be the difference in the [$^3$H]-Prog binding between the presence and the absence of 1 µM unlabeled Prog.

In the case of MR binding assay, [$^3$H]-Ald (about 4 nM), MR cytosol (about 1 mg/mL concentration of total protein), a test compound and a binding buffer were mixed in a total volume of 50 µL, and the mixture was stood at 4° C. for 30 min or longer. A specific binding was defined to be the difference in the [$^3$H]-Ald binding between the presence and the absence of 1 µM unlabeled Ald.

After the reaction, 50 µL of DCC was added to each well and blended. Thereafter, the mixture was stood at 4° C. for 10 min. The plate was applied to high-speed cooling centrifuge under the conditions of 4° C., 2000 rpm, 5 min to perform B/F separation. A given amount of the supernatant was recovered, which was spotted on Filtermat A of 96 well format (PerkinElmer) and rapidly dried at a high temperature. Then, solid scintillator MeltiLex A (PerkinElmer) was melted on Filtermat A. The mixture was placed in a Sample Bag (PerkinElmer), and the level of radioactivity was measured by plate reader 1450 Micro Beta TRILUX (PerkinElmer).

Measurement of Inhibition Constant (Ki)

The concentration (IC$_{50}$) of a test compound necessary for inhibiting 50% of a specific binding was determined by Hill analysis of competitive binding experiments. Ki of the test compound was determined by the following Cheng-Prusoff equation:

$$Ki=IC_{50}/(1+[L*]/Kd)$$

wherein L* is a concentration of radioactive ligand and Kd is a dissociation constant for radioactive ligand determined by saturation analysis.

In the case of GR, Kd was about 3.1 nM. In the case of PRB and MR, Kd was about 3.5 nM and about 2.0 nM, respectively.

Experimental Example 2

Glucocorticoid Receptor Function Test Using Transgenic-Recombinant Cell

Transgenic-recombinant cell was prepared by our company (Yokohama, JP). In Hokkaido System Science Co., Ltd., a cis-element wherein two glucocorticoid responsive elements (GRE) present in the tyrosine hydroxylase promoter region of mouse were connected in tandem was produced on order from synthetic DNA. The gene was incorporated into a plasmid vector having a gene encoding luciferase enzyme. The plasmid was incorporated into CHO-K1 cell to give a transfectant. The expression cell (CHO-GRE-Luc #35) produces luciferase instead of the object protein under regulation of a transcription region involved in the expression of the object protein. That is, using the cell, a substance that controls production of the object protein can be screened for by replacing the substance with the luciferase activity. Fetal Bovine Serum (FBS), L-glutamine, penicillin-streptomycin solution, PBS(−), trypsin-EDTA solution, Opti-MEM medium and G418 were obtained from GIBCO (Auckland, N.Z.). A 10 cm dish and DMEM:HAM'S F12 medium were obtained from IWAKI (Chiba, JP). A 96 well white plate was obtained from Corning (Corning, N.Y.). Bright-Glo was obtained from Promega (Madison, US). Dexamethasone was obtained from Sigma Chemicals (St. Louis, Mo.).

CHO-GRE-Luc #35 cells were cultured for several days in a 10 cm dish in a medium (10% FBS/DMEM:HAM'S F12/2.5 mM L-glutamine/50 U/mL penicillin/25 µg/mL streptomycin/500 µg/mL G418). Sub-confluent cells were washed with a suitable amount of PBS(−), 1 ml of Trypsin-EDTA was added and the cells were stood still in a CO$_2$ incubator at 37° C. for 3 min. A 10-fold amount of Opti-MEM medium was added to give a suspension, which was placed in a centrifugal tube and centrifuged (25° C., 1,000 rpm, 5 min). The supernatant was removed, and the cells were suspended in 5 ml of Opti-MEM medium and counted. The cells were diluted with Opti-MEM medium to 2.5×10$^5$ cells/ml, plated at 80 µL/well on a 96 well white plate, and stood still in a CO$_2$ incubator at 37° C. for about 24 hr.

Storage solutions (5-20 mM) of the compound were prepared with DMSO. The storage solutions were diluted with DMSO to 1 mM, and further diluted 100-fold with distilled water or Opti-MEM medium to give solutions. The preparations were diluted with 1% DMSO solution to each concentration. As GR agonist, 10 nM dexamethasone was used. 0.2% DMSO was present at the time of the function assay.

The prepared compound solutions (evaluation compound solution or 1% DMSO solution 10 μL+dexamethasone or 1% DMSO solution 10 μL) were added to the plate. After the addition, the place was stood still in a $CO_2$ incubator at 37° C. for about 6 hr. After the reaction, Bright-Glo was added at 20 μL/well, and the mixture was gently shaken and measured by a microplate luminometer (Turner Designs Instrument).

Measurement of 50% Inhibitory Concentration ($IC_{50}$)

The $IC_{50}$ value (nM) of the evaluation compound against GR stimulation with dexamethasone was calculated using Prism 3.0 as an analysis software and assuming one-site competition.

Results of Receptor Binding Assay and 50% Inhibitory Concentration Assay

The Example compounds were evaluated using the protocol described herein. The compounds were found to be GR receptor selective antagonists. The binding affinity and $IC_{50}$ of the compounds of Examples 2, 13, 14, 17, 20, 21 and 29 are shown in Table 11.

TABLE 11

| | GR (Ki: nM) | PR (Ki: nM) | MR (Ki: nM) | GR ($IC_{50}$: nM) |
| --- | --- | --- | --- | --- |
| Example 2 | 15 | >1250 | >1000 | 30 |
| Example 13 | 54 | >1250 | >1000 | 31 |
| Example 14 | 11 | >1250 | >1000 | 21 |
| Example 17 | 53 | >1250 | >1000 | 91 |
| Example 20 | 70 | >1250 | >1000 | 74 |
| Example 21 | 35 | >1250 | >1000 | 53 |
| Example 29 | 58 | >1250 | >1000 | 69 |

This application is based on a patent application No. 2007-005472 filed in Japan (filing date: Jan. 15, 2007), the contents of which are incorporated in full herein by this reference.

The invention claimed is:

1. A condensed tetrahydroquinoline compound represented by the following formula (I)

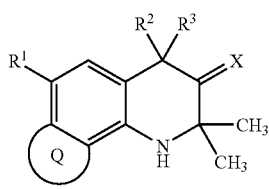

(I)

wherein $R^1$ is optionally substituted $C_6$-$C_{10}$ aryl, optionally substituted 5- or 6- membered heterocyclic aryl or optionally substituted bicyclic heteroaryl, $R^2$ and $R^3$ are the same or different and each independently is a hydrogen atom, $C_1$-$C_6$ alkyl, $C_1$-$C_6$ alkyl optionally substituted by 1 to 3 halogens, $C_2$-$C_6$ alkenyl or $C_2$-$C_6$ alkynyl, ring Q is the following formula (II-a), (II-b) or (II-c),

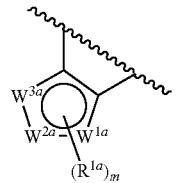

II-a

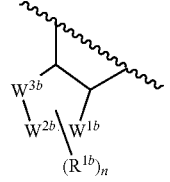

II-b

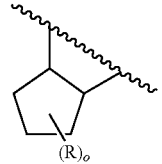

II-c wherein m, n and o are each independently 0, 1 or 2, R, $R^{1a}$ and $R^{1b}$ may be the same or different and each independently is a hydrogen atom, a halogen atom, provided that when o is 2, R may be =O $W^{1a}$, $W^{2a}$ and $W^{3a}$ are the same or different and each independently is —$CR^{1a}$=, or an oxygen atom, $W^{1b}$ and $W^{2b}$ are the same or different and each independently is —$CHR^{1b}$—, $C(R^{1b}$ —$)_2$ or an oxygen atom, $W^{3b}$ is —$CHR^{1b}$—, or an oxygen atom and when $W^{1a}$, $W^{2a}$ and $W^{3a}$, or $W^{1b}$, $W^{2b}$ and $W^{3b}$ are oxygen atoms, then the atoms are not sequentially bonded, and X is =$CH_2$ or an oxygen atom, or a pharmaceutically acceptable salt thereof.

2. The condensed tetrahydroquinoline compound of claim 1, wherein $R^1$ is the formula (III-a)

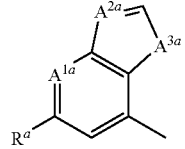

III-a wherein $R^a$ is $C_1$-$C_6$ alkyl or a halogen atom, $A^{1a}$ and $A^{2a}$ are the same or different and each independently is —N= or —CH=, and $A^{3a}$ is —NH— or —O—, the formula (III-b)

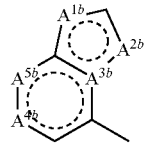

III-b wherein $A^{1b}$ and $A^{2b}$ are the same or different and each independently is —NH—, —N= or —CH=, $A^{3b}$ is a nitrogen atom or a carbon atom, $A^{4b}$ and $A^{5b}$ are the same or different and each independently is a nitrogen atom or —CR$^b$═, and R$^b$ is a hydrogen atom, C$_1$-C$_6$ alkyl or a halogen atom, provided that at least two of A$^{1b}$, A$^{2b}$, A$^{3b}$, A$^{4b}$ and A$^{5b}$ are a carbon atom, —CH═ or —CR$^b$═, the formula (III-c)

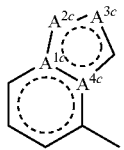

III-c wherein A$^{1c}$ and A$^{4c}$ are the same or different and each independently is a nitrogen atom or a carbon atom, A$^{2c}$ is —NH—, —N═ or —CH═, and A$^{3c}$ is —N═ or —CH═, provided that A$^{1c}$ and A$^{4c}$ are not simultaneously nitrogen atoms,
the formula (III-d)

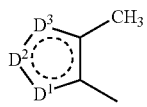

III-d wherein D$^1$ is —S—, —C(R$^{d1}$)═ or —N(R$^{d2}$)—, D$^2$ is —S—, —C(R$^{d2}$)═ or —N═, D$^3$ is —O—, —S—, —C(R$^{d2}$)═ or —N═, R$^{d1}$ is a hydrogen atom, C$_1$-C$_6$ alkyl, C$_1$-C$_6$ alkoxy, amino, C$_1$-C$_6$ alkylamino, di(C$_1$-C$_6$ alkyl)amino, cyano or hydroxyiminomethyl, and R$^{d2}$ is a hydrogen atom, cyano or C$_1$-C$_6$ alkyl, provided that when any of D$^1$, D$^2$ and D$^3$ is —S— or —O—, the other two are not —O— and —S—,
the formula (III-e)

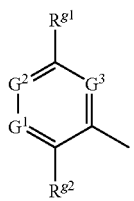

III-e wherein G$^1$ is —N═ or —C(R$^{g3}$)═, G$^2$ and G$^3$ are the same or different and each independently is —N═ or —CH═, R$^{g1}$ is a hydrogen atom, a halogen atom or C$_1$-C$_6$ alkyl, R$^{g2}$ is a halogen atom, C$_1$-C$_6$ alkyl or C$_1$-C$_6$ alkoxy, and R$^{g3}$ is a hydrogen atom or a halogen atom, wherein one of G$^1$-G$^3$ is —N═, and the other two are —C(R$^{g3}$)═ or —CH═, naphthyridine, thienopyridine, phthalazine, quinoline, benzoxazole, dioxoindoline, hydroxynaphthalene, 3,5-dimethylpyrazole, or phenyl optionally substituted by 1 or 2 groups selected from the group consisting of a hydroxyl group, a halogen atom, C$_1$-C$_6$ alkyl and C$_1$-C$_6$ alkoxy,
or a pharmaceutically acceptable salt thereof.

3. The condensed tetrahydroquinoline compound of claim 1, wherein R$^1$ is the formula (III-d), naphthyridine, thienopyridine or phthalazine, and ring Q is the formula (II-b), or a pharmaceutically acceptable salt thereof.

4. The condensed tetrahydroquinoline compound of claim 1, which is 6-(2-chloro-4-hydroxyphenyl)-2,2,4,4-tetramethyl-2,3,4,7,8,9-hexahydro-1H-cyclopenta[h]quinolin-3-one,
6-(3,5-dimethylisoxazol-4-yl)-2,2,4,4-tetramethyl-2,3,4,7,8,9,-hexahydro-1H-cyclopenta[h]quinolin-3-one,
6-(3,5-dimethyl-3H-imidazol-4-yl)-2,2,4,4-tetramethyl-2,3,4,7,8,9-hexahydro-1H-cyclopenta[h]quinolin-3-one,
6-(3,5-dimethyl-3H-[1,2,3]triazol-4-yl)-2,2,4,4-tetramethyl-2,3,4,7,8,9-hexahydro-1H-cyclopenta[h]quinolin-3-one,
6-(2-cyano-3-methylthiophen-4-yl)-2,2,4,4-tetramethyl-2,3,4,7,8,9-hexahydro-1H-cyclopenta[h]quinolin-3-one,
2,2,4,4-tetramethyl-6-(3-methylpyridin-4-yl)-2,3,4,7,8,9-hexahydro-1H-cyclopenta[h]quinolin-3-one,
6-(2-chloropyridin-3-yl)-2,2,4,4-tetramethyl-2,3,4,7,8,9-hexahydro-1H-cyclopenta[h]quinolin-3-one,
6-(5-fluoro-2-methoxypyridin-3-yl)-2,2,4,4-tetramethyl-2,3,4,7,8,9-hexahydro-1H-cyclopenta[h]quinolin-3-one,
6-(2,5-dimethylpyridin-4-yl)-2,2,4,4-tetramethyl-2,3,4,7,8,9-hexahydro-1H-cyclopenta[h]quinolin-3-one,
6-(1H-indol-7-yl)-2,2,4,4-tetramethyl-2,3,4,7,8,9-hexahydro-1H-cyclopenta[h]quinolin-3-one,
6-(5-fluoro-1H-indol-7-yl)-2,2,4,4-tetramethyl-2,3,4,7,8,9-hexahydro-1H-cyclopenta[h]quinolin-3-one,
6-(1H-benzimidazol-4-yl)-2,2,4,4-tetramethyl-2,3,4,7,8,9-hexahydro-1H-cyclopenta[h]quinolin-3-one,
2,2,4,4-tetramethyl-6-(1H-pyrrolo[3,2-b]pyridin-7-yl)-2,3,4,7,8,9-hexahydro-1H-cyclopenta[h]quinolin-3-one,
6-(imidazo[1,2-a]pyridin-5-yl)-2,2,4,4-tetramethyl-2,3,4,7,8,9-hexahydro-1H-cyclopenta[h]quinolin-3-one,
6-(1H-indazol-4-yl)-2,2,4,4-tetramethyl-2,3,4,7,8,9-hexahydro-1H-cyclopenta[h]quinolin-3-one,
2,2,4,4-tetramethyl-6-(pyrazolo[1,5-a]pyridin-4-yl)-2,3,4,7,8,9-hexahydro-1H-cyclopenta[h]quinolin-3-one,
2,2,4,4-tetramethyl-6-([1,2,4]triazolo[4,3-a]pyridin-5-yl)-2,3,4,7,8,9-hexahydro-1H-cyclopenta[h]quinolin-3-one,
6-(imidazo[1,2-a]pyrazin-5-yl)-2,2,4,4-tetramethyl-2,3,4,7,8,9-hexahydro-1H-cyclopenta[h]quinolin-3-one,
2,2,4,4-tetramethyl-6-(thieno[2,3-b]pyridin-3-yl)-2,3,4,7,8,9-hexahydro-1H-cyclopenta[h]quinolin-3-one,
2,2,4,4-tetramethyl-6-(quinolin-5-yl)-2,3,4,7,8,9-hexahydro-1H-cyclopenta[h]quinolin-3-one,
2,2,4,4-tetramethyl-6-([1,8]naphthyridin-4-yl)-2,3,4,7,8,9-hexahydro-1H-cyclopenta[h]quinolin-3-one,
2,2,4,4-tetramethyl-6-(phthalazin-5-yl)-2,3,4,7,8,9-hexahydro-1H-cyclopenta[h]quinolin-3-one,
6-(3,5-dimethylisoxazol-4-yl)-2,2,4,4-tetramethyl-3-methylene-2,3,4,7,8,9-hexahydro-1H-cyclopenta[h]quinoline,
6-(imidazo[1,2-a]pyridin-5-yl)-2,2,4,4-tetramethyl-3-methylene-2,3,4,7,8,9-hexahydro-1H-cyclopenta[h]quinoline,
2,2,4,4-tetramethyl-3-methylene-6-([1,8]naphthyridin-4-yl)-2,3,4,7,8,9-hexahydro-1H-cyclopenta[h]quinoline,
2,2,4,4-tetramethyl-3-methylene-6-([1,2,4]triazolo[4,3-a]pyridin-5-yl)-2,3,4,7,8,9-hexahydro-1H-cyclopenta[h]quinoline,
6-(imidazo[1,2-a]pyrazin-5-yl)-2,2,4,4-tetramethyl-3-methylene-2,3,4,7,8,9-hexahydro-1H-cyclopenta[h]quinoline,
6-(3,5-dimethyl-3H-[1,2,3]triazol-4-yl)-2,2,4,4-tetramethyl-3-methylene-2,3,4,7,8,9-hexahydro-1H-cyclopenta[h]quinoline, 6-(3,5-dimethyl-3H-imidazol-4-yl)-2,2,4,4-tetramethyl-3-methylene-2,3,4,7,8,9-hexahydro-1H-cyclopenta[h]quinoline,
2,2,4,4-tetramethyl-6-([1,8]naphthyridin-4-yl)-1,2,3,4,8,9-hexahydro-furo[2,3-h]quinolin-3-one or
2,2,4,4-tetramethyl-6-([1,8]naphthyridin-4-yl)-1,2,3,4-tetrahydro-furo[2,3-h]quinolin-3-one,
or a pharmaceutically acceptable salt thereof.

5. The condensed tetrahydroquinoline compound of claim 1, which is
6-(3,5-dimethylisoxazol-4-yl)-2,2,4,4-tetramethyl-2,3,4,7,8,9,-hexahydro-1H-cyclopenta[h]quinolin-3-one,
6-(3,5-dimethyl-3H-[1,2,3]triazol-4-yl)-2,2,4,4-tetramethyl-2,3,4,7,8,9-hexahydro-1H-cyclopenta[h]quinolin-3-one,
2,2,4,4-tetramethyl-6-(3-methylpyridin-4-yl)-2,3,4,7,8,9-hexahydro-1H-cyclopenta[h]quinolin-3-one,
6-(5-fluoro-2-methoxypyridin-3-yl)-2,2,4,4-tetramethyl-2,3,4,7,8,9-hexahydro-1H-cyclopenta[h]quinolin-3-one,
6-(2,5-dimethylpyridin-4-yl)-2,2,4,4-tetramethyl-2,3,4,7,8,9-hexahydro-1H-cyclopenta[h]quinolin-3-one,
6-(1H-indol-7-yl)-2,2,4,4-tetramethyl-2,3,4,7,8,9-hexahydro-1H-cyclopenta[h]quinolin-3-one,
2,2,4,4-tetramethyl-6-(1H-pyrrolo[3,2-b]pyridin-7-yl)-2,3,4,7,8,9-hexahydro-1H-cyclopenta[h]quinolin-3-one,
6-(imidazo[1,2-a]pyridin-5-yl)-2,2,4,4-tetramethyl-2,3,4,7,8,9-hexahydro-1H-cyclopenta[h]quinolin-3-one,
6-(1H-indazol-4-yl)-2,2,4,4-tetramethyl-2,3,4,7,8,9-hexahydro-1H-cyclopenta[h]quinolin-3-one,
2,2,4,4-tetramethyl-6-(pyrazolo[1,5-a]pyridin-4-yl)-2,3,4,7,8,9-hexahydro-1H-cyclopenta[h]quinolin-3-one,
2,2,4,4-tetramethyl-6-([1,2,4]triazolo[4,3-a]pyridin-5-yl)-2,3,4,7,8,9-hexahydro-1H-cyclopenta[h]quinolin-3-one,
6-(imidazo[1,2-a]pyrazin-5-yl)-2,2,4,4-tetramethyl-2,3,4,7,8,9-hexahydro-1H-cyclopenta[h]quinolin-3-one,
2,2,4,4-tetramethyl-6-(thieno[2,3-b]pyridin-3-yl)-2,3,4,7,8,9-hexahydro-1H-cyclopenta[h]quinolin-3-one,
2,2,4,4-tetramethyl-6-(quinolin-5-yl)-2,3,4,7,8,9-hexahydro-1H-cyclopenta[h]quinolin-3-one,
2,2,4,4-tetramethyl-6-([1,8]naphthyridin-4-yl)-2,3,4,7,8,9-hexahydro-1H-cyclopenta[h]quinolin-3-one,
6-(3,5-dimethylisoxazol-4-yl)-2,2,4,4-tetramethyl-3-methylene-2,3,4,7,8,9-hexahydro-1H-cyclopenta[h]quinoline,
6-(imidazo[1,2-a]pyridin-5-yl)-2,2,4,4-tetramethyl-3-methylene-2,3,4,7,8,9-hexahydro-1H-cyclopenta[h]quinoline,
2,2,4,4-tetramethyl-3-methylene-6-([1,8]naphthyridin-4-yl)-2,3,4,7,8,9-hexahydro-1H-cyclopenta[h]quinoline,
2,2,4,4-tetramethyl-3-methylene-6-([1,2,4]triazolo[4,3-a]pyridin-5-yl)-2,3,4,7,8,9-hexahydro-1H-cyclopenta[h]quinoline,
6-(3,5-dimethyl-3H-imidazol-4-yl)-2,2,4,4-tetramethyl-3-methylene-2,3,4,7,8,9-hexahydro-1H-cyclopenta[h]quinoline,
2,2,4,4-tetramethyl-6-([1,8]naphthyridin-4-yl)-1,2,3,4,8,9-hexahydro-furo[2,3-h]quinolin-3-one or
2,2,4,4-tetramethyl-6-([1,8]naphthyridin-4-yl)-1,2,3,4-tetrahydro-furo[2,3-h]quinolin-3-one,
or a pharmaceutically acceptable salt thereof.

6. A condensed tetrahydroquinoline compound represented by the following formula (I)

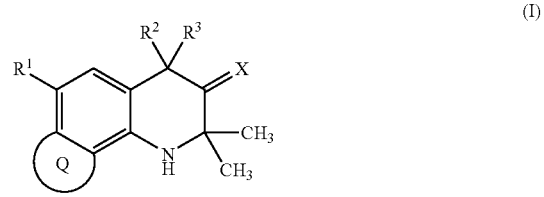

(I)

wherein $R^1$ is optionally substituted $C_6$-$C_{10}$ aryl, optionally substituted 5- or 6-membered heterocyclic aryl or optionally substituted bicyclic heteroaryl, $R^2$, and $R^3$ may be the same or different and each independently is a hydrogen atom or $C_1$-$C_6$ alkyl, ring Q is the following formula (II-a), (II-b) or (II-c),

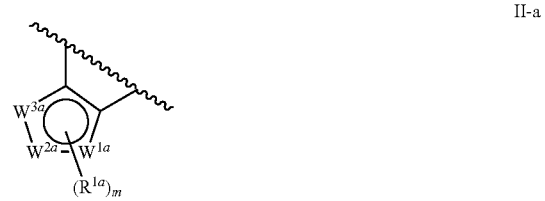

II-a

II-b

II-c wherein, m, n and o may be the same or different and each independently is 0 or 1, R, $R^{1a}$, and $R^{1b}$ is a hydrogen atom, $W^{1a}$, $W^{2a}$ and $W^{3a}$ are the same or different and each independently is —$CR^{1a}$—, or an oxygen atom, or an oxygen atom, $W^{1b}$ and $W^{2b}$ are the same or different and each independently is —$CHR^{1b}$—, —$C(R^{1b}-)_2$— or an oxygen atom, $W^{3b}$ is —$CHR^{1b}$—, or an oxygen atom, wherein at least one of $W^{1a}$, $W^{2a}$ and $W^{3a}$, or $W^{1b}$, $W^{2b}$ and $W^{3b}$ is —$CH_2$—, and X is =$CH_2$ or an oxygen atom, or a pharmaceutically acceptable salt thereof.

7. The condensed tetrahydroquinoline compound of claim 6, wherein $R^1$ is the formula (III-a)

III-a wherein $R^a$ is $C_1$-$C_6$ alkyl or a halogen atom, $A^{1a}$ and $A^{2a}$ are the same or different and each independently is —N= or —CH=, $A^{3a}$ is —NH— or —O—, the formula (III-b)

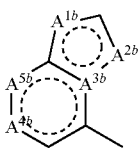

wherein $A^{1b}$ and $A^{1b}$ are the same or different and each independently is —NH—, —N= or —CH=, $A^{3b}$ is a nitrogen atom or a carbon atom, $A^{4b}$ and $A^{5b}$ are the same or different and each independently is a nitrogen atom or —$CR^b$=, $R^b$ is a hydrogen atom, $C_1$-$C_6$ alkyl or a halogen atom, wherein at least two of $A^{1b}$, $A^{2b}$, $A^{3b}$, $A^{4b}$ and $A^{5b}$ are a carbon atom, —CH= or —$CR^b$=, the formula (III-c)

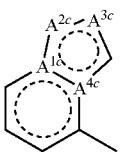

wherein $A^{1c}$ and $A^{4c}$ are the same or different and each independently is a nitrogen atom or a carbon atom, $A^{2c}$ is —NH—, —N= or —CH=, $A^{3c}$ is —N= or —CH=, wherein $A^{1c}$ and $A^{4c}$ are not simultaneously nitrogen atoms, the formula (III-d)

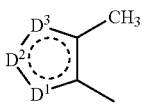

wherein $D^1$ is —S—, —C($R^{d1}$)= or —N($R^{d2}$)—, $D^2$ is —S—, —C($R^{d2}$)= or —N=, $D^3$ is —O—, —S—, —C($R^{d2}$)= or —N=, $R^{d1}$ is a hydrogen atom or $C_1$-$C_6$ alkoxy, $R^{d2}$ is a hydrogen atom, cyano or $C_1$-$C_6$ alkyl, provided that when any of $D^1$, $D^2$ and $D^3$ is —S— or —O—, the other two are not —O— or —S—, the formula (III-e)

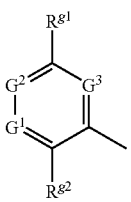

wherein $G^1$ is —N= or —C($R^{g3}$)=, $G^2$ and $G^3$ are the same or different and each independently is —N= or —CH=, $R^{g1}$ is a hydrogen atom, a halogen atom or $C_1$-$C_6$ alkyl, $R^{g2}$ is a halogen atom, $C_1$-$C_6$ alkyl or $C_1$-$C_6$ alkoxy, $R^{g3}$ is a hydrogen atom or a halogen atom, wherein two of $G^1$-$G^3$ are —C($R^{g3}$)=, naphthyridine, thienopyridine, phthalazine, or phenyl optionally substituted by 1 or 2 groups selected from the group consisting of a hydroxyl group, a halogen atom, $C_1$-$C_6$ alkyl and $C_1$-$C_6$ alkoxy, or a pharmaceutically acceptable salt thereof.

8. The condensed tetrahydroquinoline compound of claim 6, wherein $R^1$ is the formula (III-d), naphthyridine, thienopyridine or phthalazine, and ring Q is the formula (II-b), or a pharmaceutically acceptable salt thereof.

9. The condensed tetrahydroquinoline compound of claim 6, which is 6-(2-chloro-4-hydroxyphenyl)-2,2,4,4-tetramethyl-2,3,4,7,8,9-hexahydro-1H-cyclopenta[h]quinolin-3-one, 6-(3,5-dimethylisoxazol-4-yl)-2,2,4,4-tetramethyl-2,3,4,7,8,9,-hexahydro-1H-cyclopenta[h]quinolin-3-one, 6-(3,5-dimethyl-3H-imidazol-4-yl)-2,2,4,4-tetramethyl-2,3,4,7,8,9-hexahydro-1H-cyclopenta[h]quinolin-3-one, 6-(3,5-dimethyl-3H-[1,2,3]triazol-4-yl)-2,2,4,4-tetramethyl-2,3,4,7,8,9-hexahydro-1H-cyclopenta[h]quinolin-3-one, 6-(2-cyano-3-methylthiophen-4-yl)-2,2,4,4-tetramethyl-2,3,4,7,8,9-hexahydro-1H-cyclopenta[h]quinolin-3-one, 2,2,4,4-tetramethyl-6-(3-methylpyridin-4-yl)-2,3,4,7,8,9-hexahydro-1H-cyclopenta[h]quinolin-3-one, 6-(2-chloropyridin-3-yl)-2,2,4,4-tetramethyl-2,3,4,7,8,9-hexahydro-1H-cyclopenta[h]quinolin-3-one, 6-(5-fluoro-2-methoxypyridin-3-yl)-2,2,4,4-tetramethyl-2,3,4,7,8,9-hexahydro-1H-cyclopenta[h]quinolin-3-one, 6-(2,5-dimethylpyridin-4-yl)-2,2,4,4-tetramethyl-2,3,4,7,8,9-hexahydro-1H-cyclopenta[h]quinolin-3-one, 6-(1H-indol-7-yl)-2,2,4,4-tetramethyl-2,3,4,7,8,9-hexahydro-1H-cyclopenta[h]quinolin-3-one, 6-(5-fluoro-1H-indol-7-yl)-2,2,4,4-tetramethyl-2,3,4,7,8,9-hexahydro-1H-cyclopenta[h]quinolin-3-one, 6-(1H-benzimidazol-4-yl)-2,2,4,4-tetramethyl-2,3,4,7,8,9-hexahydro-1H-cyclopenta[h]quinolin-3-one, 2,2,4,4-tetramethyl-6-(1H-pyrrolo[3,2-b]pyridin-7-yl)-2,3,4,7,8,9-hexahydro-1H-cyclopenta[h]quinolin-3-one, 6-(imidazo[1,2-a]pyridin-5-yl)-2,2,4,4-tetramethyl-2,3,4,7,8,9-hexahydro-1H-cyclopenta[h]quinolin-3-one, 6-(1H-indazol-4-yl)-2,2,4,4-tetramethyl-2,3,4,7,8,9-hexahydro-1H-cyclopenta[h]quinolin-3-one, 2,2,4,4-tetramethyl-6-(pyrazolo[1,5-a]pyridin-4-yl)-2,3,4,7,8,9-hexahydro-1H-cyclopenta[h]quinolin-3-one, 2,2,4,4-tetramethyl-6-([1,2,4]triazolo[4,3-a]pyridin-5-yl)-2,3,4,7,8,9-hexahydro-1H-cyclopenta[h]quinolin-3-one, 6-(imidazo[1,2-a]pyrazin-5-yl)-2,2,4,4-tetramethyl-2,3,4,7,8,9-hexahydro-1H-cyclopenta[h]quinolin-3-one, 2,2,4,4-tetramethyl-6-(thieno[2,3-b]pyridin-3-yl)-2,3,4,7,8,9-hexahydro-1H-cyclopenta[h]quinolin-3-one, 2,2,4,4-tetramethyl-6-(quinolin-5-yl)-2,3,4,7,8,9-hexahydro-1H-cyclopenta[h]quinolin-3-one, 2,2,4,4-tetramethyl-6-([1,8]naphthyridin-4-yl)-2,3,4,7,8,9-hexahydro-1H-cyclopenta[h]quinolin-3-one, 2,2,4,4-tetramethyl-6-(phthalazin-5-yl)-2,3,4,7,8,9-hexahydro-1H-cyclopenta[h]quinolin-3-one, 6-(3,5-dimethylisoxazol-4-yl)-2,2,4,4-tetramethyl-3-methylene-2,3,4,7,8,9-hexahydro-1H-cyclopenta[h]quinoline, 6-(imidazo[1,2-a]pyridin-5-yl)-2,2,4,4-tetramethyl-3-methylene-2,3,4,7,8,9-hexahydro-1H-cyclopenta[h]quinoline, 2,2,4,4-tetramethyl-3-methylene-6-([1,8]naphthyridin-4-yl)-2,3,4,7,8,9-hexahydro-1H-cyclopenta[h]quinoline, 2,2,4,4-tetramethyl-3-methylene-6-([1,2,4]triazolo[4,3-a]pyridin-5-yl)-2,3,4,7,8,9-hexahydro-1H-cyclopenta[h]quinoline, 6-(imidazo[1,2-a]pyrazin-5-yl)-2,2,4,4-tetramethyl-3-methylene-2,3,4,7,8,9-hexahydro-1H-cyclopenta[h]quinoline, 6-(3,5-dimethyl-3H-[1,2,3]triazol-4-yl)-2,2,4,4-tetramethyl-3-methylene-2,3,4,7,8,9-hexahydro-1H-cyclopenta[h]quinoline or 6-(3,5-dimethyl-3H-imidazol-4-yl)-2,2,4,4-tetramethyl-3-methylene-2,3,4,7,8,9-hexahydro-1H-cyclopenta[h]quinoline, or a pharmaceutically acceptable salt thereof.

10. The condensed tetrahydroquinoline compound of claim 6, which is 6-(3,5-dimethylisoxazol-4-yl)-2,2,4,4-tetramethyl-2,3,4,7,8,9,-hexahydro-1H-cyclopenta[h]quinolin-3-one, 6-(3,5-dimethyl-3H-[1,2,3]triazol-4-yl)-2,2,4,4-tetramethyl-2,3,4,7,8,9-hexahydro-1H-cyclopenta[h]quinolin-3-one, 2,2,4,4-tetramethyl-6-(3-methylpyridin-4-yl)-2,3,4,7,8,9-hexahydro-1H-cyclopenta[h]quinolin-3-one, 6-(5-fluoro-2-methoxypyridin-3-yl)-2,2,4,4-tetramethyl-2,3,4,7,8,9-hexahydro-1H-cyclopenta[h]quinolin-3-one, 6-(2,5-dimethylpyridin-4-yl)-2,2,4,4-tetramethyl-2,3,4,7,8,9-hexahydro-1H-cyclopenta[h]quinolin-3-one, 6-(1H-indol-7-yl)-2,2,4,4-tetramethyl-2,3,4,7,8,9-hexahydro-1H-cyclopenta[h]quinolin-3-one, 2,2,4,4-tetramethyl-6-(1H-pyrrolo[3,2-b]pyridin-7-yl)-2,3,4,7,8,9-hexahydro-1H-cyclopenta[h]quinolin-3-one, 6-(imidazo[1,2-a]pyridin-5-yl)-2,2,4,4-tetramethyl-2,3,4,7,8,9-hexahydro-1H-cyclopenta[h]quinolin-3-one, 6-(1H-indazol-4-yl)-2,2,4,4-tetramethyl-2,3,4,7,8,9-hexahydro-1H-cyclopenta[h]quinolin-3-one, 2,2,4,4-tetramethyl-6-(pyrazolo[1,5-a]pyridin-4-yl)-2,3,4,7,8,9-hexahydro-1H-cyclopenta[h]quinolin-3-one, 2,2,4,4-tetramethyl-6-([1,2,4]triazolo[4,3-a]pyridin-5-yl-2,3,4,7,8,9-hexahydro-1H-cyclopenta[h]quinolin-3-one, 6-(imidazo[1,2-a]pyrazin-5-yl)-2,2,4,4-tetramethyl-2,3,4,7,8,9-hexahydro-1H-cyclopenta[h]quinolin-3-one, 2,2,4,4-tetramethyl-6-(thieno[2,3-b]pyridin-3-yl)-2,3,4,7,8,9-hexahydro-1H-cyclopenta[h]quinolin-3-one, 2,2,4,4-tetramethyl-6-(quinolin-5-yl)-2,3,4,7,8,9-hexahydro-1H-cyclopenta[h]quinolin-3-one, 2,2,4,4-tetramethyl-6-([1,8]naphthyridin-4-yl)-2,3,4,7,8,9-hexahydro-1H-cyclopenta[h]quinolin-3-one, 6-(3,5-dimethylisoxazol-4-yl)-2,2,4,4-tetramethyl-3-methylene-2,3,4,7,8,9-hexahydro-1H-cyclopenta[h]quinoline, 6-(imidazo[1,2-a]pyridin-5-yl)-2,2,4,4-tetramethyl-3-methylene-2,3,4,7,8,9-hexahydro-1H-cyclopenta[h]quinoline, 2,2,4,4-tetramethyl-3-methylene-6-([1,8]naphthyridin-4-yl)-2,3,4,7,8,9-hexahydro-1H-cyclopenta[h]quinoline, 2,2,4,4-tetramethyl-3-methylene-6-([1,2,4]triazolo[4,3-a]pyridin-5-yl)-2,3,4,7,8,9-hexahydro-1H-cyclopenta[h]quinoline or 6-(3,5-dimethyl-3H-imidazol-4-yl)-2,2,4,4-tetramethyl-3-methylene-2,3,4,7,8,9-hexahydro-1H-cyclopenta[h]quinoline, or a pharmaceutically acceptable salt thereof.

11. A pharmaceutical composition comprising the condensed tetrahydroquinoline compound of claim 1 or a pharmaceutically acceptable salt thereof, and a pharmaceutically acceptable carrier.

12. A pharmaceutical composition comprising the condensed tetrahydroquinoline compound of claim 6 or a pharmaceutically acceptable salt thereof, and a pharmaceutically acceptable carrier.

\* \* \* \* \*

UNITED STATES PATENT AND TRADEMARK OFFICE
CERTIFICATE OF CORRECTION

PATENT NO. : 8,367,695 B2
APPLICATION NO. : 12/523031
DATED : February 5, 2013
INVENTOR(S) : Eda et al.

It is certified that error appears in the above-identified patent and that said Letters Patent is hereby corrected as shown below:

In the Claims:

Claim 1, column 92, lines 10-17, formula 11(b) should read:

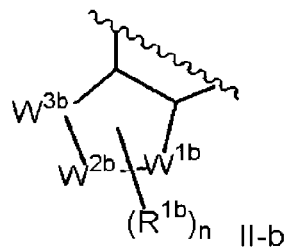

Claim 1, column 92, line 28:
"hydrogen atom, halogen atom" should read "hydrogen atom or a halogen atom"

Claim 1, column 92, line 29:
"R may be =O" should read "R may be =O,"

Claim 1, column 92, line 30:
"independently is -$CR^{1a}$=," should read "independently is -$CR^{1a}$="

Claim 1, column 92, line 32:
"independently is -$CHR^{1b}$-, -$C(R^{1b}-)_2$" should read "independently is -$CHR^{1b}$-, -$C(R^{1b})_2$-,"

Claim 1, column 92, line 34:
"atom and when" should read "atom, and when"

Signed and Sealed this
Twenty-seventh Day of August, 2013

Teresa Stanek Rea
*Acting Director of the United States Patent and Trademark Office*

Claim 1, column 92, line 35:

"are oxygen atoms" should read "are plural oxygen atoms"

Claim 6, column 96, lines 26-33, formula II(b), should read:

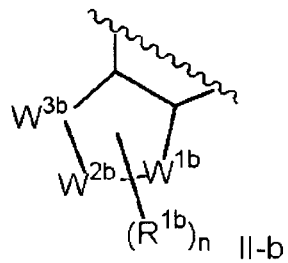

Claim 6, column 96, lines 45-46:

"each independently is -CR$^{1a}$-, or an oxygen atom, or an oxygen atom," should read "each independently is -CR$^{1a}$- or an oxygen atom,"

Claim 6, column 96, lines 47-48:

"and each independently is -CHR$^{1b}$-, -C(R$^{1b}$-)$_2$- or an oxygen atom, W$^{3b}$ is -CHR$^{1b}$-, or an oxygen" should read "each independently is -CHR$^{1b}$-, -C(R$^{1b}$)$_2$-, or an oxygen, W$^{3b}$ is -CHR$^{1b}$- or an oxygen"